(12) United States Patent
Hynes et al.

(10) Patent No.: US 11,395,743 B1
(45) Date of Patent: Jul. 26, 2022

(54) EXTERNALLY DRIVEN EXPANDABLE INTERBODY AND RELATED METHODS

(71) Applicant: Warsaw Orthopedic, Inc., Warsaw, IN (US)

(72) Inventors: Richard A. Hynes, Melbourne Beach, FL (US); Jonathan M. Dewey, Memphis, TN (US); Joshua A. Ruth, Edina, MN (US); Douglas H. Wentz, Seymour, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/307,578

(22) Filed: May 4, 2021

(51) Int. Cl.
*A61F 2/44* (2006.01)
*A61F 2/30* (2006.01)

(52) U.S. Cl.
CPC .. *A61F 2/4425* (2013.01); *A61F 2002/30301* (2013.01); *A61F 2002/30507* (2013.01); *A61F 2002/443* (2013.01)

(58) Field of Classification Search
CPC ............... A61F 2/447; A61F 2/4455
See application file for complete search history.

(56) References Cited

U.S. PATENT DOCUMENTS

| | | |
|---|---|---|
| 4,401,112 A | 8/1983 | Rezaian |
| 4,553,273 A | 11/1985 | Wu |
| 4,636,217 A | 1/1987 | Ogilvie et al. |
| 4,759,769 A | 7/1988 | Hedman et al. |
| 5,059,193 A | 10/1991 | Kuslich |
| 5,171,278 A | 12/1992 | Pisharodi |

(Continued)

FOREIGN PATENT DOCUMENTS

| | | |
|---|---|---|
| DE | 44 16 6 05 C1 | 6/1995 |
| EP | 0 880 950 A1 | 12/1998 |

(Continued)

OTHER PUBLICATIONS

International Search Report, and Written Opinion for Application. No. PCT/US2019/019067, dated Jun. 3, 2019.

(Continued)

*Primary Examiner* — Ellen C Hammond
(74) *Attorney, Agent, or Firm* — Fox Rothschild LLP; P. Marshall Ticer

(57) ABSTRACT

An expandable implant having superior and inferior endplates is disclosed. The superior endplate includes a first inside surface having a crossbar extending in the widthwise direction. The inferior endplate includes a second inside surface having a medial support structure, a threaded core, and a receiving cavity. A threaded locking screw may be disposed in the threaded core, and a proximal saddle may be disposed in the receiving cavity. In various embodiments, in a locked position, a relative position of the inferior endplate with respect to the superior endplate is fixed, and the threaded locking screw directly contacts, pushes, applies a force against, and/or compresses, the proximal saddle, the proximal saddle directly contacts, pushes, applies a force against, and/or compresses the crossbar, the crossbar directly contacts, pushes, applies a force against, and/or compresses the distal saddle, and the distal saddle directly contacts and is engaged against the second interior distal wall.

20 Claims, 39 Drawing Sheets

(56) References Cited

U.S. PATENT DOCUMENTS

| | | |
|---|---|---|
| 5,336,223 A | 8/1994 | Rogers |
| 5,390,683 A | 2/1995 | Pisharodi |
| 5,522,899 A | 6/1996 | Michelson |
| 5,554,191 A | 9/1996 | Lahille et al. |
| 5,575,790 A | 11/1996 | Chen et al. |
| 5,609,635 A | 3/1997 | Michelson |
| 5,653,762 A | 8/1997 | Pisharodi |
| 5,658,336 A | 8/1997 | Pisharodi |
| 5,665,122 A | 9/1997 | Kambin |
| 5,693,100 A | 12/1997 | Pisharodi |
| 5,697,977 A | 12/1997 | Pisharodi |
| 5,702,391 A | 12/1997 | Lin |
| 5,702,453 A | 12/1997 | Rabbe et al. |
| 5,702,455 A | 12/1997 | Saggar |
| 5,797,918 A | 8/1998 | McGuire et al. |
| 5,800,550 A | 9/1998 | Sertich |
| 5,865,848 A | 2/1999 | Baker |
| 5,893,890 A | 4/1999 | Pisharodi |
| 5,931,777 A | 8/1999 | Sava |
| 5,941,885 A | 8/1999 | Jackson |
| 5,971,987 A | 10/1999 | Huxel et al. |
| 5,980,522 A | 11/1999 | Koros et al. |
| 6,045,579 A | 4/2000 | Hochshuler et al. |
| 6,074,343 A | 6/2000 | Nathanson et al. |
| 6,080,193 A | 6/2000 | Hochshuler et al. |
| 6,099,531 A | 8/2000 | Bonutti |
| 6,102,949 A | 8/2000 | Biedermann et al. |
| 6,102,950 A | 8/2000 | Vaccaro |
| 6,106,557 A | 8/2000 | Robioneck et al. |
| 6,113,638 A | 9/2000 | Williams et al. |
| 6,117,174 A | 9/2000 | Nolan |
| 6,132,465 A | 10/2000 | Ray et al. |
| 6,159,211 A | 12/2000 | Boriani et al. |
| 6,159,244 A | 12/2000 | Suddaby |
| 6,176,882 B1 | 1/2001 | Biedermann et al. |
| 6,179,873 B1 | 1/2001 | Zientek |
| 6,190,414 B1 | 2/2001 | Young et al. |
| 6,193,757 B1 | 2/2001 | Foley et al. |
| 6,217,579 B1 | 4/2001 | Koros |
| 6,245,108 B1 | 6/2001 | Biscup |
| 6,309,421 B1 | 10/2001 | Pisharodi |
| 6,342,074 B1 | 1/2002 | Simpson |
| 6,371,989 B1 | 4/2002 | Chauvin et al. |
| 6,395,031 B1 | 5/2002 | Foley et al. |
| 6,423,063 B1 | 7/2002 | Bonutti |
| 6,432,106 B1 | 8/2002 | Fraser |
| 6,436,140 B1 | 8/2002 | Liu et al. |
| 6,443,989 B1 | 9/2002 | Jackson |
| 6,443,990 B1 | 9/2002 | Aebi et al. |
| 6,454,806 B1 | 9/2002 | Cohen et al. |
| 6,454,807 B1 | 9/2002 | Jackson |
| 6,461,359 B1 | 10/2002 | Tribus et al. |
| 6,491,724 B1 | 12/2002 | Ferree |
| 6,520,991 B2 | 2/2003 | Huene |
| 6,520,993 B2 | 2/2003 | James et al. |
| 6,527,803 B1 | 3/2003 | Crozet et al. |
| 6,562,074 B2 | 5/2003 | Gerbec et al. |
| 6,576,016 B1 | 6/2003 | Hochshuler et al. |
| 6,623,525 B2 | 9/2003 | Ralph et al. |
| 6,629,998 B1 | 10/2003 | Lin |
| 6,635,086 B2 | 10/2003 | Lin |
| 6,648,917 B2 | 11/2003 | Gerbec et al. |
| 6,676,703 B2 | 1/2004 | Biscup |
| 6,685,742 B1 | 2/2004 | Jackson |
| 6,723,126 B1 | 4/2004 | Berry |
| 6,770,096 B2 | 8/2004 | Bolger et al. |
| 6,773,460 B2 | 8/2004 | Jackson |
| 6,821,298 B1 | 11/2004 | Jackson |
| 6,835,206 B2 | 12/2004 | Jackson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,923,814 B1 | 8/2005 | Hildebrand et al. |
| 6,926,737 B2 | 8/2005 | Jackson |
| 6,953,477 B2 | 10/2005 | Berry |
| 6,964,687 B1 | 11/2005 | Bernard et al. |
| 6,974,480 B2 | 12/2005 | Messerli et al. |
| 6,984,234 B2 | 1/2006 | Bray |
| 7,112,222 B2 | 9/2006 | Fraser et al. |
| 7,135,043 B2 | 11/2006 | Nakahara et al. |
| 7,137,997 B2 | 11/2006 | Paul |
| 7,172,627 B2 | 2/2007 | Fiere et al. |
| 7,188,626 B2 | 3/2007 | Foley et al. |
| 7,204,853 B2 | 4/2007 | Gordon et al. |
| 7,232,464 B2 | 6/2007 | Mathieu et al. |
| 7,238,203 B2 | 7/2007 | Bagga et al. |
| 7,255,700 B2 | 8/2007 | Kaiser et al. |
| 7,316,532 B2 | 1/2008 | Matthys-Mark |
| 7,316,714 B2 | 1/2008 | Gordon et al. |
| 7,407,483 B2 | 8/2008 | Perez-Cruet et al. |
| 7,481,766 B2 | 1/2009 | Lee et al. |
| 7,491,168 B2 | 2/2009 | Raymond et al. |
| 7,537,565 B2 | 5/2009 | Bass |
| 7,618,456 B2 | 11/2009 | Mathieu et al. |
| 7,625,394 B2 | 12/2009 | Molz, IV et al. |
| 7,655,046 B2 | 2/2010 | Dryer et al. |
| 7,678,148 B2 | 3/2010 | Peterman |
| 7,703,727 B2 | 4/2010 | Selness |
| 7,708,778 B2 | 5/2010 | Gordon et al. |
| 7,708,779 B2 | 5/2010 | Edie et al. |
| 7,727,280 B2 | 6/2010 | McLuen |
| 7,753,958 B2 | 7/2010 | Gordon et al. |
| 7,780,594 B2 | 8/2010 | Hutton |
| 7,806,932 B2 | 10/2010 | Webb et al. |
| 7,815,682 B1 | 10/2010 | Peterson et al. |
| 7,819,801 B2 | 10/2010 | Miles et al. |
| 7,824,428 B2 | 11/2010 | Mikkonen et al. |
| 7,828,849 B2 | 11/2010 | Lim |
| 7,846,167 B2 | 12/2010 | Garcia et al. |
| 7,846,207 B2 | 12/2010 | Lechmann et al. |
| 7,850,731 B2 | 12/2010 | Brittan et al. |
| 7,850,733 B2 | 12/2010 | Baynham et al. |
| 7,862,616 B2 | 1/2011 | Lechmann et al. |
| 7,875,076 B2 | 1/2011 | Mathieu et al. |
| 7,892,173 B2 | 2/2011 | Miles et al. |
| 7,909,869 B2 | 3/2011 | Gordon et al. |
| 7,914,559 B2 | 3/2011 | Carls et al. |
| 7,967,821 B2 | 6/2011 | Sicvol et al. |
| 7,981,031 B2 | 7/2011 | Frasier et al. |
| 8,016,836 B2 | 9/2011 | Corrao et al. |
| 8,062,375 B2 | 11/2011 | Glerum et al. |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,182,539 B2 | 5/2012 | Tyber et al. |
| 8,257,442 B2 | 9/2012 | Edie et al. |
| 8,262,570 B2 | 9/2012 | White et al. |
| 8,262,662 B2 | 9/2012 | Beardsley et al. |
| 8,287,597 B1 | 10/2012 | Pimenta et al. |
| 8,303,498 B2 | 11/2012 | Miles et al. |
| 8,303,658 B2 | 11/2012 | Peterman |
| 8,303,663 B2 | 11/2012 | Jimenez et al. |
| 8,317,866 B2 | 11/2012 | Palmatier et al. |
| 8,323,185 B2 | 12/2012 | Perez-Cruet et al. |
| 8,328,872 B2 | 12/2012 | Duffield et al. |
| 8,343,048 B2 | 1/2013 | Warren, Jr. |
| 8,353,826 B2 | 1/2013 | Weiman |
| 8,355,780 B2 | 1/2013 | Miles et al. |
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,506,635 B2 | 8/2013 | Palmatier et al. |
| 8,517,935 B2 | 8/2013 | Marchek et al. |
| 8,518,120 B2 | 8/2013 | Glerum et al. |

(56) References Cited

U.S. PATENT DOCUMENTS

| | | |
|---|---|---|
| 8,535,380 B2 | 9/2013 | Greenhalgh et al. |
| 8,550,994 B2 | 10/2013 | Miles et al. |
| 8,556,808 B2 | 10/2013 | Miles et al. |
| 8,556,979 B2 | 10/2013 | Glerum et al. |
| 8,579,809 B2 | 11/2013 | Parker |
| 8,579,979 B2 | 11/2013 | Edie et al. |
| 8,579,981 B2 | 11/2013 | Lim et al. |
| 8,602,984 B2 | 12/2013 | Raymond et al. |
| 8,608,785 B2 | 12/2013 | Reed et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,419 B2 | 3/2014 | Hardt et al. |
| 8,668,715 B2 | 3/2014 | Sandhu |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,353 B2 | 5/2014 | Bagga et al. |
| 8,740,983 B1 | 6/2014 | Arnold et al. |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 | 9/2014 | Donahoe et al. |
| 8,845,731 B2 | 9/2014 | Weiman |
| 8,845,732 B2 | 9/2014 | Weiman |
| 8,845,734 B2 | 9/2014 | Weiman |
| 8,852,252 B2 | 10/2014 | Venturini et al. |
| 8,852,282 B2 | 10/2014 | Farley et al. |
| 8,864,833 B2 | 10/2014 | Glerum et al. |
| 8,882,813 B2 | 11/2014 | Jones et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,161,841 B2 | 10/2015 | Kana et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,343 B2 | 6/2016 | Duffield et al. |
| 9,370,434 B2 | 6/2016 | Weiman |
| 9,370,435 B2 | 6/2016 | Walkenhorst et al. |
| 9,381,008 B2 | 7/2016 | Thornburg |
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Amin |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,468,405 B2 | 10/2016 | Miles et al. |
| 9,474,622 B2 | 10/2016 | McLaughlin et al. |
| 9,474,625 B2 | 10/2016 | Weiman |
| 9,480,573 B2 | 11/2016 | Perloff et al. |
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |
| 9,510,954 B2 | 12/2016 | Glerum et al. |
| 9,517,098 B2 | 12/2016 | Anderson |
| 9,522,070 B2 | 12/2016 | Flower et al. |
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |

(56) References Cited

U.S. PATENT DOCUMENTS

| | | |
|---|---|---|
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |
| 9,585,767 B2 | 3/2017 | Robinson |
| 9,592,129 B2 | 3/2017 | Slivka et al. |
| 9,597,195 B2 | 3/2017 | Cain |
| 9,603,643 B2 | 3/2017 | Reed et al. |
| 9,603,713 B2 | 3/2017 | Moskowitz et al. |
| 9,603,717 B2 | 3/2017 | Ibarra et al. |
| 9,615,818 B2 | 4/2017 | Baudouin et al. |
| 9,615,936 B2 | 4/2017 | Duffield et al. |
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,763,722 B2 | 9/2017 | Roybal |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Arnin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,907,671 B2 | 3/2018 | Fessler |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,943,342 B2 | 4/2018 | Tanaka et al. |
| 9,943,418 B2 | 4/2018 | Davenport et al. |
| 9,949,775 B2 | 4/2018 | Reed et al. |
| 9,949,841 B2 | 4/2018 | Glerum et al. |
| 9,956,087 B2 | 5/2018 | Seifert et al. |
| 9,962,202 B2 | 5/2018 | Anderson |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,016,282 B2 | 7/2018 | Seifert et al. |
| 10,016,284 B2 | 7/2018 | Moskowitz et al. |
| 10,022,239 B1 | 7/2018 | Lentner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,771 B2 | 7/2018 | Capote et al. |
| 10,034,772 B2 | 7/2018 | Glerum et al. |
| 10,034,773 B2 | 7/2018 | McLaughlin et al. |
| 10,039,539 B2 | 8/2018 | Friedrich et al. |
| 10,039,650 B2 | 8/2018 | Lamborne et al. |
| 10,052,214 B2 | 8/2018 | Jimenez et al. |
| 10,058,431 B2 | 8/2018 | Tyber et al. |
| 10,060,469 B2 | 8/2018 | Jimenez et al. |
| 10,070,852 B2 | 9/2018 | Mast et al. |
| 10,076,320 B2 | 9/2018 | Mast et al. |
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |
| 10,111,758 B2 | 10/2018 | Robinson |
| 10,117,754 B2 | 11/2018 | Davenport et al. |
| 10,117,755 B2 | 11/2018 | Emerick et al. |
| 10,137,002 B2 | 11/2018 | Padovani et al. |
| 10,137,006 B2 | 11/2018 | Dewey et al. |
| 10,137,007 B2 | 11/2018 | Dewey et al. |
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,515 B2 | 1/2019 | Lee et al. |
| 10,172,652 B2 | 1/2019 | Woolley et al. |
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |
| 10,238,375 B2 | 3/2019 | O'Connell et al. |
| 10,238,383 B2 | 3/2019 | Moskowitz et al. |

(56) References Cited

U.S. PATENT DOCUMENTS

| | | |
|---|---|---|
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,622 B2 | 6/2019 | Brumfield et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |
| 10,327,912 B1 | 6/2019 | Suddaby |
| 10,327,917 B2 | 6/2019 | Glerum et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,633 B2 | 10/2019 | Moskowitz et al. |
| 10,426,634 B1 | 10/2019 | Al-Jazaeri et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,889 B2 | 3/2020 | Roybal |
| 10,575,960 B2 | 3/2020 | Duffield et al. |
| 10,582,959 B2 | 3/2020 | Langer et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,163 B2 | 5/2020 | Fyber et al. |
| 10,639,166 B2 | 5/2020 | Weiman et al. |
| 10,653,458 B2 | 5/2020 | Tanaka et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Weiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 | 11/2020 | Weiman et al. |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,447 B2 | 12/2020 | Tanaka et al. |
| 10,874,522 B2 | 12/2020 | Weiman |
| 10,874,523 B2 | 12/2020 | Weiman et al. |
| 10,874,524 B2 | 12/2020 | Bjork |
| 10,881,524 B2 | 1/2021 | Eisen et al. |
| 10,881,531 B2 | 1/2021 | Berry |
| 10,888,431 B1 | 1/2021 | Robinson |
| 10,898,344 B2 | 1/2021 | Alheidt et al. |
| 10,898,346 B1 | 1/2021 | Suddaby |
| 10,925,656 B2 | 2/2021 | Cole et al. |
| 10,925,750 B2 | 2/2021 | Zappacosta et al. |
| 10,925,752 B2 | 2/2021 | Weiman |
| 10,932,920 B2 | 3/2021 | Dewey et al. |
| 10,940,014 B2 | 3/2021 | Greenhalgh |
| 10,945,858 B2 | 3/2021 | Bechtel et al. |
| 10,952,866 B2 | 3/2021 | Warren et al. |
| 10,959,855 B2 | 3/2021 | Miller et al. |
| 10,959,856 B2 | 3/2021 | Seifert et al. |
| 10,973,649 B2 | 4/2021 | Weiman et al. |
| 10,973,650 B2 | 4/2021 | Stein |
| 10,980,642 B2 | 4/2021 | Glerum et al. |
| 10,980,644 B2 | 4/2021 | Purcell et al. |
| 10,993,814 B2 | 5/2021 | Wolters |
| 11,007,067 B2 | 5/2021 | Masson et al. |
| 11,013,617 B2 | 5/2021 | Weiman et al. |
| 11,020,238 B2 | 6/2021 | Nichols et al. |
| 11,020,239 B2 | 6/2021 | Miller et al. |
| 11,026,804 B2 | 6/2021 | Jimenez et al. |
| 11,026,812 B2 | 6/2021 | Daffinson et al. |
| 11,033,401 B2 | 6/2021 | Shoshtaev |
| 11,033,402 B2 | 6/2021 | Melkent et al. |
| 11,033,404 B2 | 6/2021 | Faulhaber |
| 11,039,935 B2 | 6/2021 | McAfee |
| 11,045,326 B2 | 6/2021 | Seifert et al. |
| 11,045,327 B2 | 6/2021 | Nichols et al. |
| 11,051,949 B2 | 7/2021 | Walker et al. |
| 11,051,951 B2 | 7/2021 | Robinson et al. |
| 11,058,469 B2 | 7/2021 | Mahajan et al. |
| 11,065,127 B1 | 7/2021 | Lentner et al. |
| 11,065,129 B2 | 7/2021 | Sandul |
| 11,065,130 B2 | 7/2021 | Branch et al. |
| 11,076,966 B2 | 8/2021 | Faulhaber |
| 11,083,584 B2 | 8/2021 | Lauf et al. |
| 11,083,595 B2 | 8/2021 | Robinson |
| 11,090,167 B2 | 8/2021 | Emerick et al. |
| 11,096,795 B2 | 8/2021 | Padovani et al. |
| 11,096,797 B2 | 8/2021 | Moskowitz et al. |
| 11,103,366 B2 | 8/2021 | Glerum et al. |
| RE48,719 E | 9/2021 | Suddaby et al. |
| 11,109,980 B2 | 9/2021 | Seifert et al. |
| 11,116,644 B2 | 9/2021 | Marrocco et al. |

(56) References Cited

U.S. PATENT DOCUMENTS

| | | |
|---|---|---|
| 11,123,198 B2 | 9/2021 | Black et al. |
| 11,123,200 B2 | 9/2021 | Faulhaber |
| 11,129,731 B2 | 9/2021 | Miller et al. |
| 11,135,071 B2 | 10/2021 | Dewey et al. |
| 11,147,680 B2 | 10/2021 | Tyber et al. |
| 11,154,404 B2 | 10/2021 | Freedman et al. |
| 11,160,666 B2 | 11/2021 | Burkhardt et al. |
| 11,160,669 B2 | 11/2021 | Rogers et al. |
| 11,166,826 B2 | 11/2021 | Huang |
| 11,173,044 B1 | 11/2021 | Jones et al. |
| 11,179,234 B2 | 11/2021 | Dacosta et al. |
| 2002/0045943 A1 | 4/2002 | Uk |
| 2002/0045945 A1 | 4/2002 | Liu et al. |
| 2002/0116066 A1 | 8/2002 | Chauvin et al. |
| 2002/0128713 A1 | 9/2002 | Ferree |
| 2002/0151976 A1 | 10/2002 | Foley et al. |
| 2003/0050701 A1 | 3/2003 | Michelson |
| 2003/0130739 A1 | 7/2003 | Gerbec et al. |
| 2004/0172134 A1 | 9/2004 | Berry |
| 2004/0186570 A1 | 9/2004 | Rapp |
| 2004/0193158 A1 | 9/2004 | Lim et al. |
| 2004/0249461 A1 | 12/2004 | Ferree |
| 2004/0254643 A1 | 12/2004 | Jackson |
| 2004/0254644 A1 | 12/2004 | Taylor |
| 2005/0015149 A1 | 1/2005 | Michelson |
| 2005/0033429 A1 | 2/2005 | Kuo |
| 2005/0033439 A1 | 2/2005 | Gordon et al. |
| 2006/0122701 A1 | 6/2006 | Kiester |
| 2006/0129244 A1 | 6/2006 | Ensign |
| 2007/0218750 A1 | 9/2007 | Corrao et al. |
| 2007/0270859 A1 | 11/2007 | Companioni et al. |
| 2008/0132959 A1 | 6/2008 | Mikkonen et al. |
| 2008/0140207 A1 | 6/2008 | Olmos et al. |
| 2009/0024158 A1 | 1/2009 | Viker |
| 2009/0292361 A1 | 11/2009 | Lopez |
| 2010/0082109 A1 | 4/2010 | Greenhalgh et al. |
| 2010/0191336 A1 | 7/2010 | Greenhalgh |
| 2010/0211176 A1 | 8/2010 | Greenhalgh |
| 2010/0286777 A1 | 11/2010 | Errico et al. |
| 2011/0118843 A1 | 5/2011 | Mathieu et al. |
| 2011/0130838 A1 | 6/2011 | Morgenstern Lopez |
| 2011/0153020 A1 | 6/2011 | Abdelgany et al. |
| 2011/0218572 A1 | 9/2011 | Lechmann et al. |
| 2012/0095515 A1 | 4/2012 | Hamilton |
| 2012/0101581 A1 | 4/2012 | Mathieu et al. |
| 2012/0109142 A1 | 5/2012 | Dayan |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0150237 A1 | 6/2012 | Combrowski |
| 2012/0197401 A1 | 8/2012 | Duncan et al. |
| 2012/0209385 A1 | 8/2012 | Aferzon |
| 2012/0215316 A1 | 8/2012 | Mohr et al. |
| 2013/0190876 A1 | 7/2013 | Drochner et al. |
| 2013/0211526 A1 | 8/2013 | Alheidt et al. |
| 2013/0226191 A1 | 8/2013 | Thoren et al. |
| 2013/0231747 A1 | 9/2013 | Olmos et al. |
| 2013/0304136 A1 | 11/2013 | Gourlaouen-Preissler et al. |
| 2013/0317312 A1 | 11/2013 | Eastlack et al. |
| 2014/0107790 A1 | 4/2014 | Combrowski |
| 2014/0114420 A1 | 4/2014 | Robinson |
| 2014/0163682 A1 | 6/2014 | Iott et al. |
| 2014/0180419 A1 | 6/2014 | Dmuschewsky |
| 2014/0194992 A1 | 7/2014 | Medina |
| 2014/0277500 A1 | 9/2014 | Logan et al. |
| 2014/0303674 A1 | 10/2014 | Sasing |
| 2015/0223945 A1 | 8/2015 | Weiman et al. |
| 2015/0230931 A1 | 8/2015 | Greenhalgh |
| 2015/0238236 A1 | 8/2015 | Sasing |
| 2016/0008924 A1 | 1/2016 | Canourgues et al. |
| 2016/0022434 A1 | 1/2016 | Robinson |
| 2016/0081681 A1 | 3/2016 | Waugh et al. |
| 2016/0089247 A1 | 3/2016 | Nichols et al. |
| 2016/0095710 A1 | 4/2016 | Juszczyk et al. |
| 2016/0242930 A1 | 8/2016 | Duffield et al. |
| 2016/0256291 A1 | 9/2016 | Miller |
| 2016/0278830 A1 | 9/2016 | Arrington |
| 2016/0296340 A1 | 10/2016 | Gordon et al. |
| 2016/0310291 A1 | 10/2016 | Greenhalgh |
| 2016/0345952 A1 | 12/2016 | Kucharzyk et al. |
| 2016/0367377 A1 | 12/2016 | Faulhaber |
| 2017/0010025 A1 | 1/2017 | Mayershofer |
| 2017/0029635 A1 | 2/2017 | Doll et al. |
| 2017/0035406 A1 | 2/2017 | Abidin et al. |
| 2017/0049651 A1 | 2/2017 | Lim et al. |
| 2017/0049653 A1 | 2/2017 | Lim et al. |
| 2017/0095345 A1 | 4/2017 | Davenport et al. |
| 2017/0100255 A1 | 4/2017 | Hleihil et al. |
| 2017/0100257 A1 | 4/2017 | Weiman et al. |
| 2017/0105844 A1* | 4/2017 | Kuyler ............... A61F 2/4601 |
| 2017/0151065 A1 | 6/2017 | Warren et al. |
| 2017/0156882 A1 | 6/2017 | Rathbun et al. |
| 2017/0156884 A1 | 6/2017 | Rathbun et al. |
| 2017/0189204 A1 | 7/2017 | Riemhofer et al. |
| 2017/0202678 A1 | 7/2017 | Duffield et al. |
| 2017/0215856 A1 | 8/2017 | Martinelli et al. |
| 2017/0224502 A1 | 8/2017 | Wolters et al. |
| 2017/0224504 A1 | 8/2017 | Butler et al. |
| 2017/0231675 A1 | 8/2017 | Combrowski |
| 2017/0246006 A1 | 8/2017 | Carnes et al. |
| 2017/0290677 A1 | 10/2017 | Olmos et al. |
| 2017/0296352 A1 | 10/2017 | Richerme et al. |
| 2017/0367842 A1 | 12/2017 | Predick et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0000606 A1 | 1/2018 | Hessler et al. |
| 2018/0030362 A1 | 2/2018 | Kosler et al. |
| 2018/0031810 A1 | 2/2018 | Hsu et al. |
| 2018/0036136 A1 | 2/2018 | Duffield et al. |
| 2018/0036138 A1 | 2/2018 | Robinson |
| 2018/0104066 A1 | 4/2018 | Bae et al. |
| 2018/0116891 A1 | 5/2018 | Beale et al. |
| 2018/0193160 A1 | 7/2018 | Hsu et al. |
| 2018/0193164 A1 | 7/2018 | Shoshtaev |
| 2018/0206999 A1 | 7/2018 | Suddaby |
| 2018/0256356 A1 | 9/2018 | Robinson et al. |
| 2018/0256359 A1 | 9/2018 | Greenhalgh |
| 2018/0256360 A1 | 9/2018 | Cain |
| 2018/0256362 A1 | 9/2018 | Slivka et al. |
| 2018/0263784 A1 | 9/2018 | Bechtel et al. |
| 2018/0280142 A1 | 10/2018 | Schultz et al. |
| 2018/0303473 A1 | 10/2018 | Spann et al. |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1 | 11/2018 | Engstrom |
| 2018/0318102 A1 | 11/2018 | Seifert et al. |
| 2018/0338838 A1 | 11/2018 | Cryder et al. |
| 2018/0338841 A1 | 11/2018 | Miller et al. |
| 2018/0344307 A1 | 12/2018 | Hynes et al. |
| 2018/0360616 A1 | 12/2018 | Luu |
| 2019/0000640 A1 | 1/2019 | Weiman |
| 2019/0000702 A1 | 1/2019 | Lim et al. |
| 2019/0000707 A1 | 1/2019 | Lim et al. |
| 2019/0020121 A1 | 1/2019 | Paulotto et al. |
| 2019/0021716 A1 | 1/2019 | Waugh et al. |
| 2019/0021873 A1 | 1/2019 | Dmuschewsky |
| 2019/0046329 A1 | 2/2019 | Padovani et al. |
| 2019/0046381 A1 | 2/2019 | Lim et al. |
| 2019/0046383 A1 | 2/2019 | Lim et al. |
| 2019/0060083 A1 | 2/2019 | Weiman et al. |
| 2019/0082949 A1 | 3/2019 | Weiman |
| 2019/0083081 A1 | 3/2019 | Ortiz et al. |
| 2019/0091033 A1 | 3/2019 | Dewey et al. |
| 2019/0105175 A1 | 4/2019 | Zappacosta et al. |
| 2019/0125328 A1 | 5/2019 | Blain |
| 2019/0133434 A1 | 5/2019 | Lee et al. |
| 2019/0133645 A1 | 5/2019 | Gordon et al. |
| 2019/0133780 A1 | 5/2019 | Matthews et al. |
| 2019/0133784 A1 | 5/2019 | Gunn et al. |
| 2019/0133788 A1 | 5/2019 | Weiman et al. |

(56) References Cited

U.S. PATENT DOCUMENTS

| | | |
|---|---|---|
| 2019/0142480 A1 | 5/2019 | Woolley et al. |
| 2019/0151115 A1 | 5/2019 | Nichols et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0209155 A1 | 7/2019 | Mast et al. |
| 2019/0216453 A1 | 7/2019 | Predick et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0247098 A1 | 8/2019 | Brumfield et al. |
| 2019/0254650 A1 | 8/2019 | Martinelli et al. |
| 2019/0254838 A1 | 8/2019 | Miller et al. |
| 2019/0254839 A1 | 8/2019 | Nichols et al. |
| 2019/0262139 A1 | 8/2019 | Wolters |
| 2019/0269521 A1 | 9/2019 | Shoshtaev |
| 2019/0274670 A1 | 9/2019 | O'Connell et al. |
| 2019/0274671 A1 | 9/2019 | Lauf et al. |
| 2019/0274836 A1 | 9/2019 | Eisen et al. |
| 2019/0282373 A1 | 9/2019 | Alheidt |
| 2019/0290446 A1 | 9/2019 | Masson et al. |
| 2019/0290447 A1 | 9/2019 | Stein |
| 2019/0298416 A1 | 10/2019 | Rezach |
| 2019/0298524 A1 | 10/2019 | Lauf et al. |
| 2019/0298540 A1 | 10/2019 | Aghayev et al. |
| 2019/0321022 A1 | 10/2019 | Karpowicz et al. |
| 2019/0321190 A1 | 10/2019 | Wagner et al. |
| 2019/0328540 A1 | 10/2019 | Seifert et al. |
| 2019/0336301 A1 | 11/2019 | Engstrom |
| 2019/0336304 A1 | 11/2019 | Burkhardt et al. |
| 2019/0350573 A1 | 11/2019 | Vogel et al. |
| 2019/0358049 A1 | 11/2019 | Faulhaber |
| 2019/0358050 A1 | 11/2019 | Fessler |
| 2019/0358051 A1 | 11/2019 | Flower et al. |
| 2019/0380840 A1 | 12/2019 | Tyber et al. |
| 2019/0388232 A1 | 12/2019 | Purcell et al. |
| 2020/0008951 A1 | 1/2020 | McClintock et al. |
| 2020/0030114 A1 | 1/2020 | Cain |
| 2020/0030116 A1 | 1/2020 | Jimenez et al. |
| 2020/0038200 A1 | 2/2020 | Foley et al. |
| 2020/0054461 A1 | 2/2020 | Marrocco et al. |
| 2020/0060844 A1 | 2/2020 | Mathieu et al. |
| 2020/0078190 A1 | 3/2020 | Rogers et al. |
| 2020/0093526 A1 | 3/2020 | Daly et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0129306 A1 | 4/2020 | Miller et al. |
| 2020/0129307 A1 | 4/2020 | Hunziker et al. |
| 2020/0138591 A1 | 5/2020 | Moskowitz et al. |
| 2020/0138593 A1 | 5/2020 | Martynova et al. |
| 2020/0146840 A1 | 5/2020 | Black et al. |
| 2020/0179120 A1 | 6/2020 | Bielenstein et al. |
| 2020/0205993 A1 | 7/2020 | Davenport et al. |
| 2020/0222202 A1 | 7/2020 | Kuyler et al. |
| 2020/0229944 A1 | 7/2020 | Suh et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0289287 A1 | 9/2020 | Emerick et al. |
| 2020/0297507 A1 | 9/2020 | Iott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390565 A1 | 12/2020 | Jimenez et al. |
| 2020/0397593 A1 | 12/2020 | Davenport et al. |
| 2020/0405497 A1 | 12/2020 | Olmos et al. |
| 2020/0405498 A1 | 12/2020 | Gray et al. |
| 2020/0405499 A1 | 12/2020 | Gerbec et al. |
| 2020/0405500 A1 | 12/2020 | Cain |
| 2021/0007860 A1 | 1/2021 | Glerum et al. |
| 2021/0015626 A1 | 1/2021 | Suddaby |
| 2021/0030555 A1 | 2/2021 | Weiman et al. |
| 2021/0030561 A1* | 2/2021 | Gleason ................ A61F 2/4455 |
| 2021/0045891 A1 | 2/2021 | Rogers et al. |
| 2021/0045892 A1 | 2/2021 | Rogers et al. |
| 2021/0052395 A1 | 2/2021 | Iott et al. |
| 2021/0068959 A1 | 3/2021 | McLuen et al. |
| 2021/0068974 A1 | 3/2021 | Cowan et al. |
| 2021/0068982 A1 | 3/2021 | Carnes et al. |
| 2021/0077272 A1 | 3/2021 | Eisen et al. |
| 2021/0085479 A1 | 3/2021 | Weiman et al. |
| 2021/0093462 A1 | 4/2021 | Lucasiewicz et al. |
| 2021/0106434 A1 | 4/2021 | Alheidt et al. |
| 2021/0113349 A1 | 4/2021 | Weiman et al. |
| 2021/0121299 A1 | 4/2021 | Hyder |
| 2021/0121300 A1 | 4/2021 | Weiman et al. |
| 2021/0137697 A1 | 5/2021 | Weiman |
| 2021/0137699 A1 | 5/2021 | Jang et al. |
| 2021/0137701 A1 | 5/2021 | Miller et al. |
| 2021/0154811 A1 | 5/2021 | Spreiter et al. |
| 2021/0161678 A1 | 6/2021 | Dewey et al. |
| 2021/0177618 A1 | 6/2021 | Branch et al. |
| 2021/0186706 A1 | 6/2021 | Spitler et al. |
| 2021/0186709 A1 | 6/2021 | Weiman et al. |
| 2021/0196470 A1 | 7/2021 | Shoshtaev |
| 2021/0205092 A1 | 7/2021 | Glerum et al. |
| 2021/0205094 A1 | 7/2021 | Weiman et al. |
| 2021/0220145 A1 | 7/2021 | Stein |
| 2021/0220147 A1 | 7/2021 | Berry |
| 2021/0236298 A1 | 8/2021 | Weiman et al. |
| 2021/0251770 A1 | 8/2021 | Purcell et al. |
| 2021/0251776 A1 | 8/2021 | Daffinson et al. |
| 2021/0259848 A1 | 8/2021 | Kang et al. |
| 2021/0259849 A1 | 8/2021 | Robinson et al. |
| 2021/0259850 A1 | 8/2021 | Eisen et al. |
| 2021/0267767 A1 | 9/2021 | Stein |
| 2021/0275317 A1 | 9/2021 | Spetzger |
| 2021/0275318 A1 | 9/2021 | Reimels |
| 2021/0275319 A1 | 9/2021 | Reimels |
| 2021/0275321 A1 | 9/2021 | Seifert et al. |
| 2021/0282938 A1 | 9/2021 | Nichols et al. |
| 2021/0298915 A1 | 9/2021 | Faulhaber |
| 2021/0298916 A1 | 9/2021 | Melkent et al. |
| 2021/0307920 A1 | 10/2021 | Walker et al. |
| 2021/0315705 A1 | 10/2021 | Altarac et al. |
| 2021/0322179 A1 | 10/2021 | Miller et al. |
| 2021/0322181 A1 | 10/2021 | Predick |
| 2021/0322182 A1 | 10/2021 | Faulhaber |
| 2021/0330472 A1 | 10/2021 | Shoshtaev |
| 2021/0346174 A1 | 11/2021 | Flint et al. |
| 2022/0015924 A1 | 1/2022 | Freedman et al. |

FOREIGN PATENT DOCUMENTS

| | | |
|---|---|---|
| EP | 0 767 636 B1 | 1/1999 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| EP | 3213720 A1 | 9/2017 |
| FR | 2781998 A1 | 2/2000 |
| FR | 3082115 A1 | 12/2019 |
| GB | 2 377 387 A | 1/2003 |
| WO | 92/14423 A1 | 9/1992 |
| WO | 97/ 00054 A1 | 1/1997 |
| WO | 99/ 26562 A1 | 6/1999 |
| WO | 99/66867 A1 | 12/1999 |
| WO | 00/12033 A1 | 3/2000 |
| WO | 00/25706 A1 | 5/2000 |
| WO | 00/ 49977 A1 | 8/2000 |
| WO | 02/19952 A1 | 3/2002 |
| WO | 03/105673 A2 | 12/2003 |

(56) References Cited

FOREIGN PATENT DOCUMENTS

| WO | 2014/133755 A1 | 9/2014 |
| WO | 2016057940 A1 | 4/2016 |
| WO | 2017/168208 A1 | 10/2017 |
| WO | 2018049227 A1 | 3/2018 |
| WO | 2021055323 A1 | 3/2021 |

OTHER PUBLICATIONS

International Search Report and Written Opinion for Application No. PCT/US2019/019060, dated Jun. 5, 2019.
International Search Report and Written Opinion, PCT/IB2020/000932, dated Jul. 29, 2021.
International Search Report and Written Opinion, PCT/IB2020/000942, dated Aug. 10, 2021.

* cited by examiner

EXTERNALLY DRIVEN EXPANDABLE INTERBODY AND RELATED METHODS

FIELD

The present technology is generally related to an externally driven expandable interbody implant for use in a medical procedure related to the spine and related methods of use and instrumentation. In some embodiments, disclosed implants may be used in an anterior cervical discectomy and fusion (ACDF) procedure although other uses in other areas of the spine or for other orthopedic applications are also contemplated.

BACKGROUND

Mechanically operated interbody implants may be used to align and/or realign a patient's spine during a medical procedure. Conventional implants designed for the Thoracic and Lumbar region of the spine often include top and bottom endplates and a mechanical means to separate the top and bottom endplates. The mechanical mechanisms to separate the top and bottom endplates are often cumbersome and require a large footprint that is often unsuitable for ACDF type surgeries of the cervical portion of the spine.

SUMMARY

The techniques of this disclosure generally relate to an expandable interbody implant including a superior endplate and an inferior endplate. The superior and inferior endplates may be moved and/or locked in a multitude of expanded configurations via an internal locking mechanism that may also allow for some lateral bending.

In one aspect, the present disclosure provides an expandable implant movable between a contracted position and an expanded position, including an expandable body extending from a proximal end to a distal end in a proximal-to-distal direction, extending from a first lateral side to a second lateral side in a widthwise direction, and extending from a superior end to an inferior end in a vertical direction, the expandable body being defined by a superior endplate and an inferior endplate opposite the superior endplate, for example. In various embodiments, the superior endplate includes a first inside surface extending in the proximal-to-distal direction between a first inside proximal wall and a first inside distal wall, and a crossbar extending in the widthwise direction proximate the first inside distal wall, for example. In various embodiments, the inferior endplate includes a second inside surface extending in the proximal-to-distal direction between a second inside proximal wall and a second inside distal wall, a medial support structure, a threaded core extending in the proximal-to-distal direction between the second inside proximal wall and the medial support structure, and a receiving cavity disposed between the medial support structure and the second inside distal wall, in various embodiments the crossbar of the superior endplate is disposed within the receiving cavity, for example. Additionally, a threaded locking screw disposed in the threaded core and movable in the proximal-to-distal direction between the interior proximal wall and the medial support structure, and a proximal saddle disposed in the receiving cavity, the proximal saddle having a proximal end portion facing the threaded locking screw and a distal end portion facing a proximal end of the crossbar, may be provided, for example. In various embodiments, a distal saddle may be disposed in the receiving cavity, the distal saddle including a proximal surface facing a distal end of the crossbar and a distal surface facing the second inside distal wall, for example. In various embodiments, in a locked position, a relative position of the inferior endplate with respect to the superior endplate is fixed, the threaded locking screw directly contacts the proximal saddle, the proximal saddle directly contacts the crossbar, the crossbar directly contacts the distal saddle, and the distal saddle directly contacts the second interior distal wall, for example.

In another aspect, a system for installing, expanding, and locking an expandable implant is disclosed. The expandable implant may be movable between a contracted position and an expanded position, including an expandable body extending from a proximal end to a distal end in a proximal-to-distal direction, extending from a first lateral side to a second lateral side in a widthwise direction, and extending from a superior end to an inferior end in a vertical direction, the expandable body being defined by a superior endplate and an inferior endplate opposite the superior endplate, for example. In various embodiments, the superior endplate includes a first inside surface extending in the proximal-to-distal direction between a first inside proximal wall and a first inside distal wall, and a crossbar extending in the widthwise direction proximate the first inside distal wall, for example. In various embodiments, the inferior endplate includes a second inside surface extending in the proximal-to-distal direction between a second inside proximal wall and a second inside distal wall, a medial support structure, a threaded core extending in the proximal-to-distal direction between the second inside proximal wall and the medial support structure, and a receiving cavity disposed between the medial support structure and the second inside distal wall, in various embodiments the crossbar of the superior endplate is disposed within the receiving cavity, for example. Additionally, a threaded locking screw disposed in the threaded core and movable in the proximal-to-distal direction between the interior proximal wall and the medial support structure, and a proximal saddle disposed in the receiving cavity, the proximal saddle having a proximal end portion facing the threaded locking screw and a distal end portion facing a proximal end of the crossbar, may be provided, for example. In various embodiments, a distal saddle may be disposed in the receiving cavity, the distal saddle including a proximal surface facing a distal end of the crossbar and a distal surface facing the second inside distal wall, for example. In various embodiments, in a locked position, a relative position of the inferior endplate with respect to the superior endplate is fixed, the threaded locking screw directly contacts the proximal saddle, the proximal saddle directly contacts the crossbar, the crossbar directly contacts the distal saddle, and the distal saddle directly contacts the second interior distal wall. In various embodiments the proximal end of the implant includes an adjustment aperture providing access to the locking screw, and a first engagement channel and a second engagement channel are disposed on opposite sides of the adjustment aperture, respectively, for example Additionally, a first surgical tool extending from a proximal end to a distal end, including a first engagement prong and a second engagement prong disposed at the distal end for coupling to the first engagement channel and second engagement channel, respectively, for example. In various embodiments, a superior handle coupled to an inferior handle at a pivot point, may be provided, for example Additionally, a second surgical tool extending longitudinally from a handle to a drive portion, the drive portion having an outside circumferential surface corresponding in size and shape to an inside circumferential surface of the locking screw, for example.

In another aspect, an expandable implant, is disclosed. The expandable implant may include an expandable body movable between a first expanded position and a second expanded position, the expandable body extending from a proximal end to a distal end in a proximal-to-distal direction, extending from a first lateral side to a second lateral side in a widthwise direction, and extending from a superior end to an inferior end in a vertical direction, the expandable body being defined by a superior endplate and an inferior endplate opposite the superior endplate, for example. In various embodiments, the superior endplate includes a first inside surface extending in the proximal-to-distal direction between a first inside proximal wall and a first inside distal wall and extending in the widthwise direction between a first inside lateral wall and a second inside lateral wall, and a crossbar extending in the widthwise direction between the first inside lateral wall and the second inside lateral wall proximate the first inside distal wall, for example. In various embodiments, the inferior endplate may include a second inside surface extending in the proximal-to-distal direction between a second inside proximal wall and a second inside distal wall, and extending in the widthwise direction between a third inside lateral wall and a fourth inside lateral wall, and a threaded core defining a rotation axis extending in the proximal-to-distal direction, for example. Furthermore, in some embodiments, a threaded locking screw disposed in the threaded core and rotatable about the rotation axis, the threaded locking screw being movable forward and backward along the rotation axis upon rotation of the threaded locking screw about the rotation axis between an unlocked position and a locked position, for example. In various embodiments, in the unlocked position, a relative position of the inferior endplate with respect to the inferior endplate is adjustable between the first expanded position and the second expanded position, and in the first expanded position, a top surface of the superior endplate and a bottom surface of the inferior endplate extend in a substantially parallel direction, respectively, with respect to the rotation axis, for example. In various embodiments, in the second expanded position, the top surface of the superior endplate is inclined with respect to the bottom surface of the inferior endplate, and in the locked position, a relative position of the inferior endplate with respect to the inferior endplate is fixed and the threaded locking screw directly contacts and may further compress or otherwise apply a force against the crossbar which may further apply a force against the second interior distal wall, for example.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 36 is a reference drawing showing the human spine of which various disclosed implant embodiments may be installed in.

FIG. 37 is a reference drawing showing various planes and reference directions of which the various disclosed implant embodiments may move in or act in.

DETAILED DESCRIPTION

Figure 1:
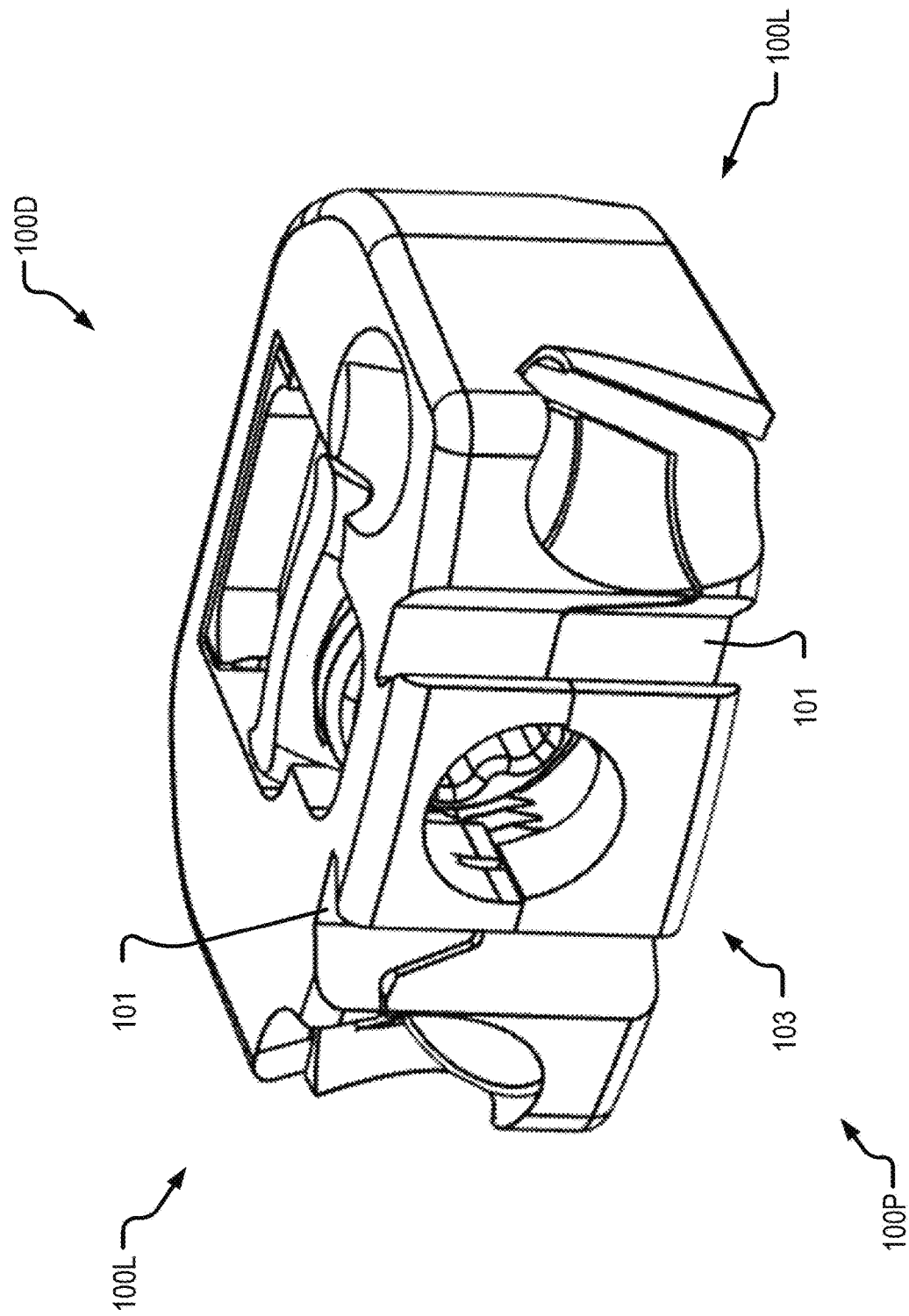
FIG. 1 is a perspective view of an expandable implant in a collapsed position.

Embodiments of the present disclosure relate generally, for example, to spinal stabilization systems, and more particularly, to an externally driven expandable interbody implant and corresponding surgical instruments for use with disclosed interbody implants. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Figure 35:
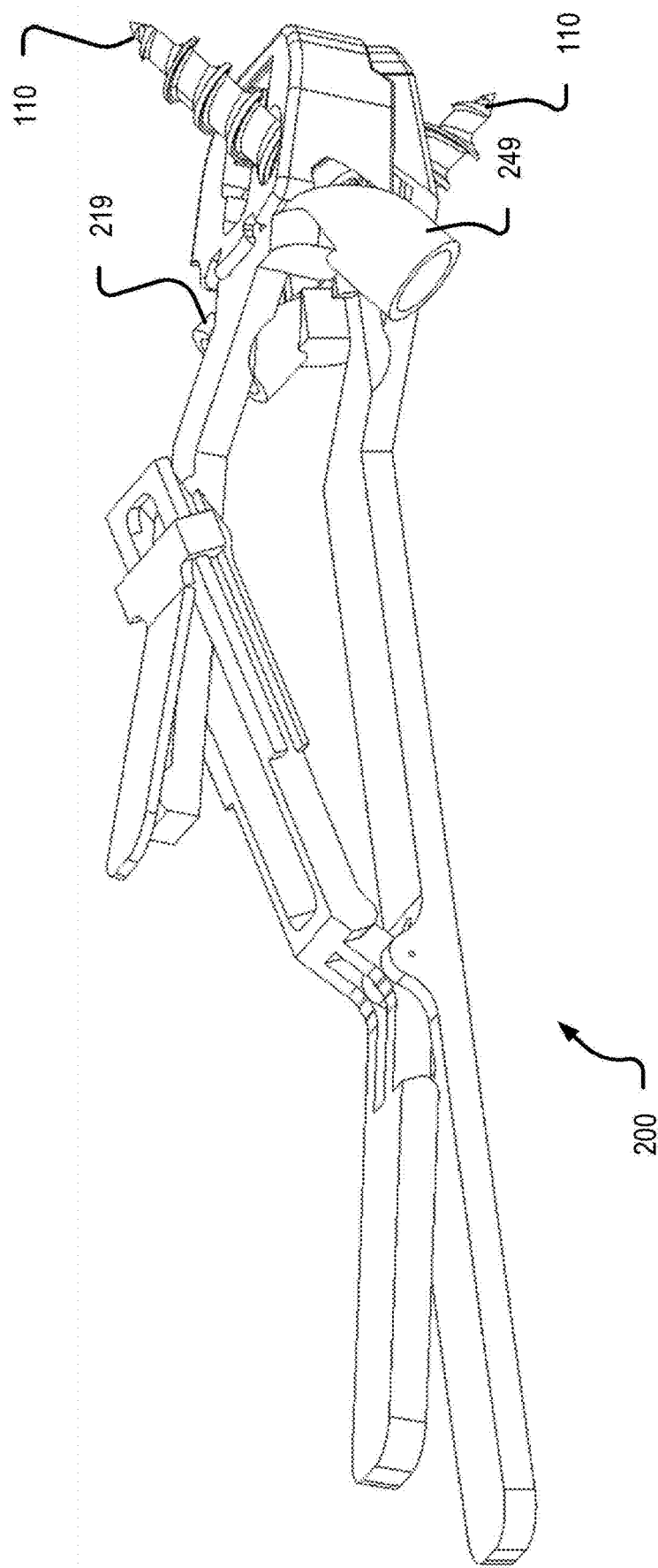
FIG. 35 is a perspective view of a first surgical tool in an expanded position having a pair of bone screw guides.
Figure 36:
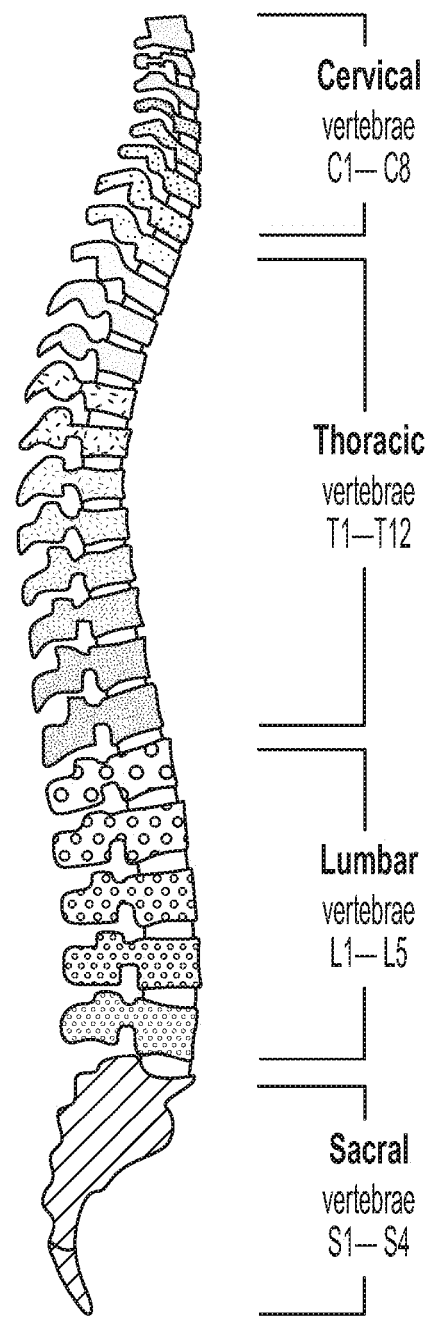
Figure 37:
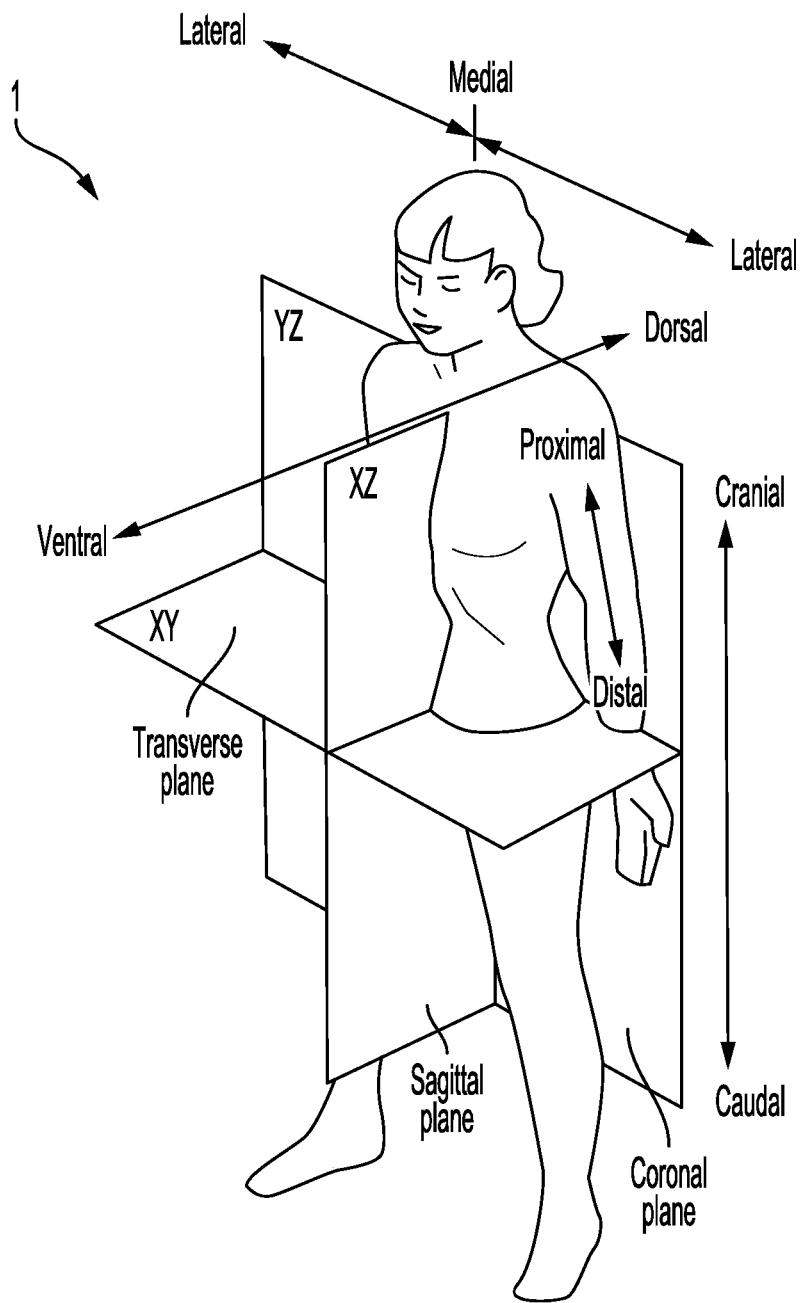

Referring generally to FIGS. 1-23 a various embodiments of an expandable implant 100 are disclosed. Referring generally to FIGS. 24-35 various embodiments of a first surgical tool 200 for inserting example expandable implants 100 and a third surgical tool 300 for locking the superior endplate 10 with respect to the inferior endplate 20 is disclosed. FIGS. 36-37 are reference drawings showing the human spine and various medical terminology as it relates to planes and directions of which the disclosed implants 100 and surgical tools 200, 300 may act in.

Figure 2:
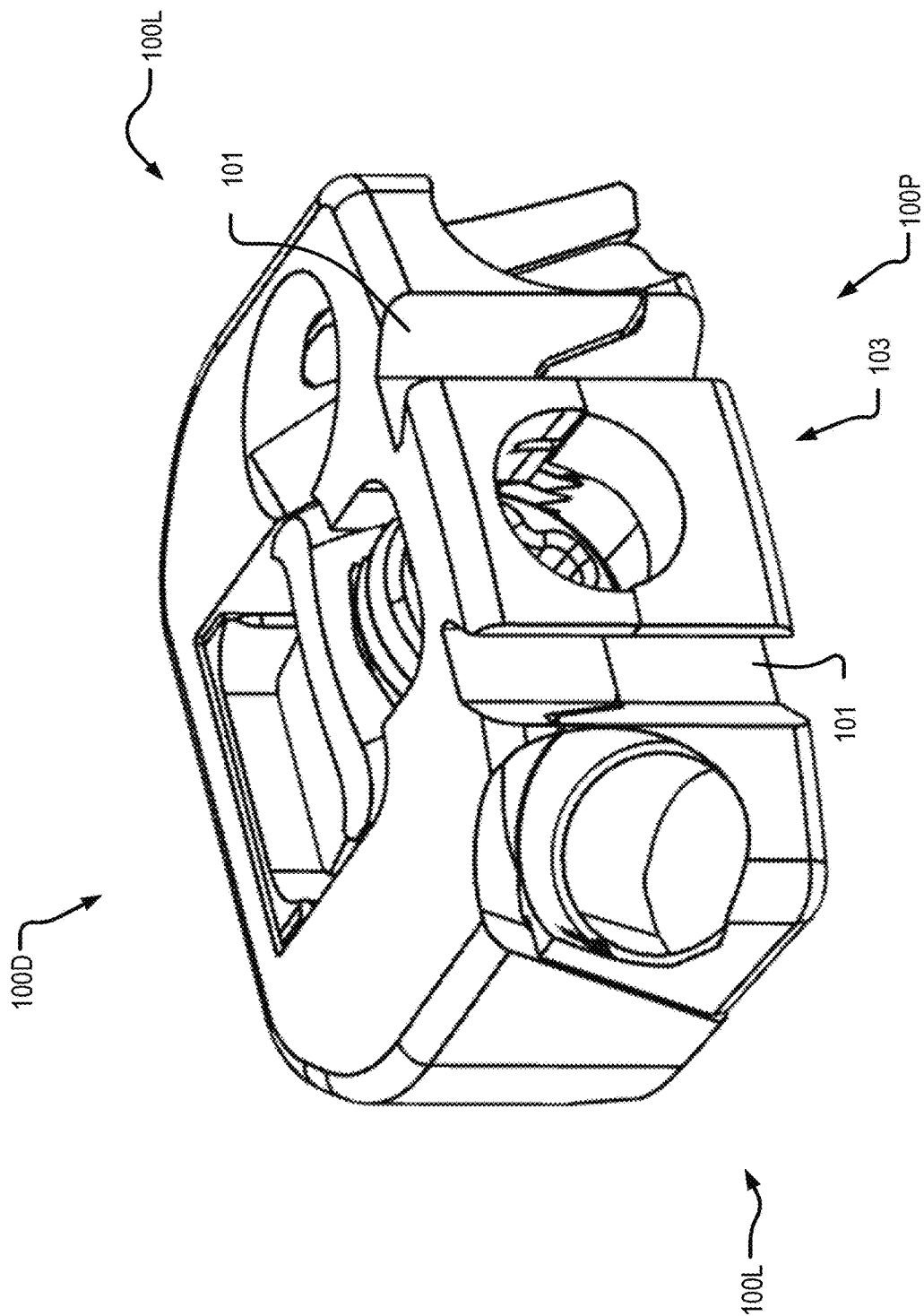
FIG. 2 is an alternate perspective view of an expandable implant in a collapsed position.
Figure 3:
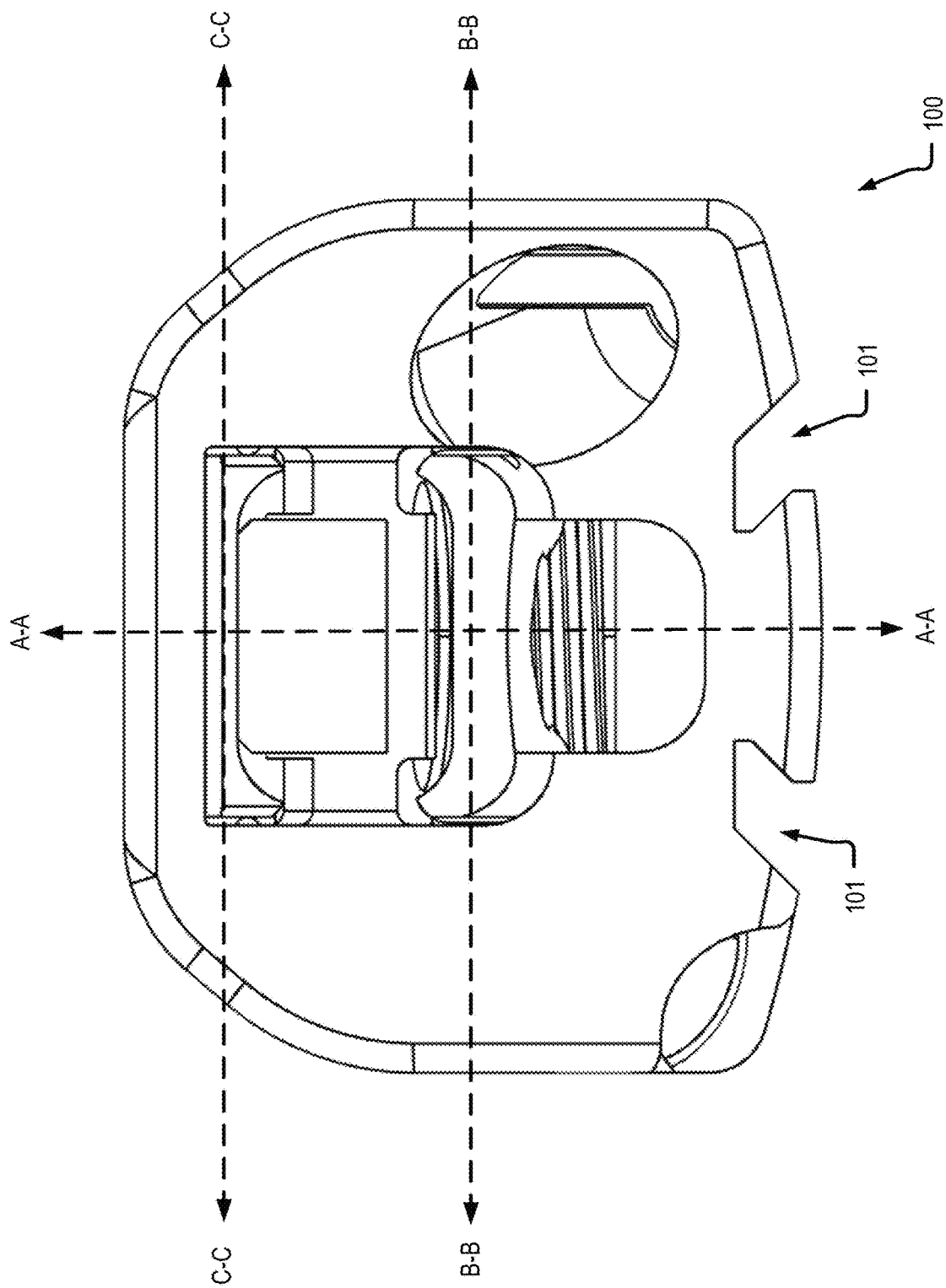
FIG. 3 is a top down view of an expandable implant.

FIGS. 1-2 illustrate example perspective views of an expandable implant 100 in a collapsed position and FIG. 3 is a top down view of an expandable implant 100. As illustrated, expandable implant 100 may include a proximal end 100p, a distal end 100d, and first and second lateral sides 100l. The proximal end 100p may include a screw guide aperture 103 and a pair of gripping channels 101 on opposite sides of the screw guide aperture 103, for example. As illustrated in FIG. 3, implant 100 may extend in a proximal-to-distal direction from the proximal end 100p to the distal end 100d though a longitudinal axis A-A through the center of the implant 100, for example. Implant 100 may extend in a widthwise direction from the first lateral side 100l to the second lateral side 100l through a widthwise axis B-B through the center of the implant 100, for example. The longitudinal axis A-A may be perpendicular and/or substantially perpendicular to the widthwise axis B-B. Various example sections through longitudinal axis A-A are illustrated in FIGS. 16-17B and 23. An example section C-C of FIG. 3 is illustrated in FIGS. 18A-18B.

Figure 4:
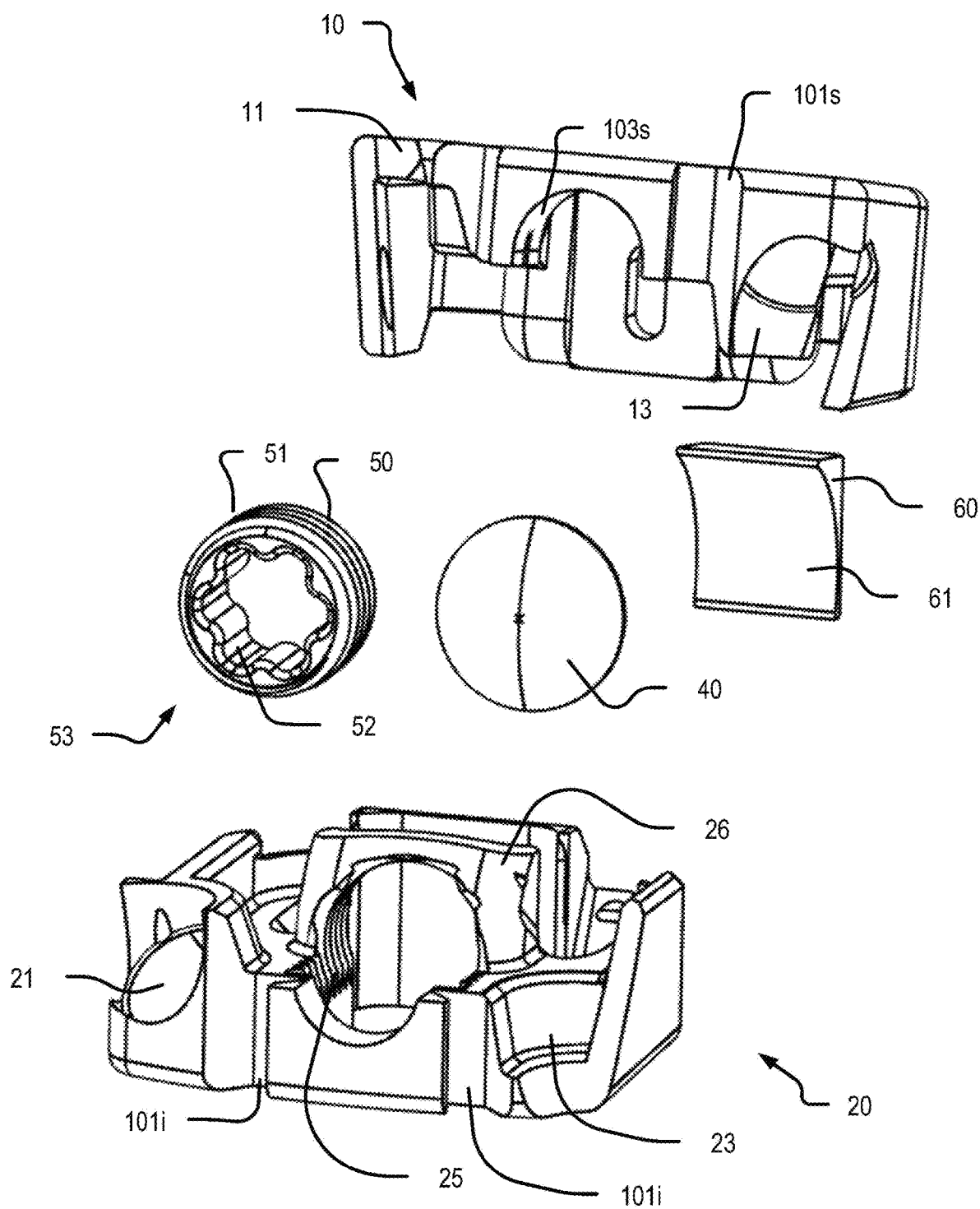
FIG. 4 is a perspective view exploded parts illustration of an expandable implant.
Figure 5:
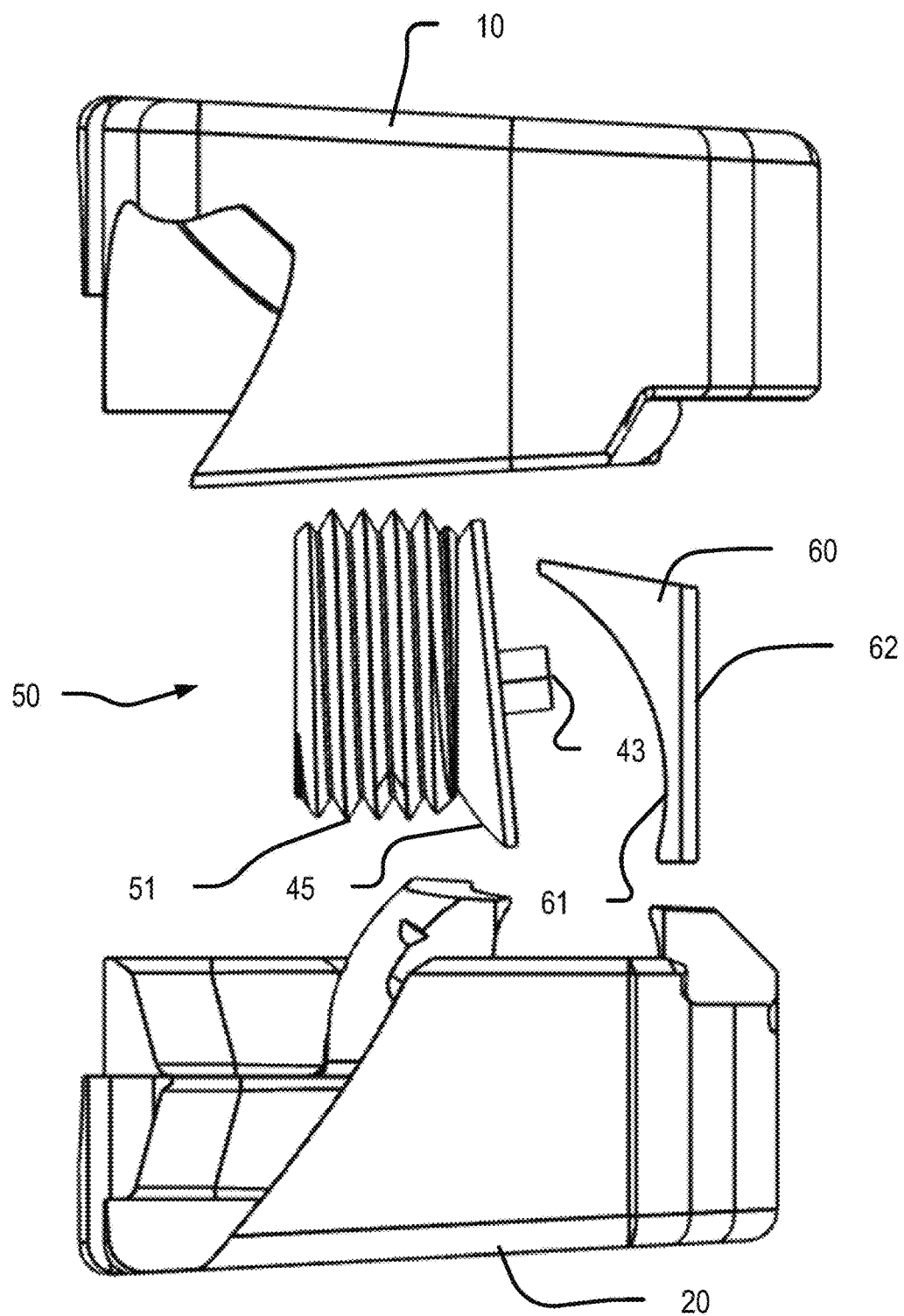
FIG. 5 is a side view exploded parts illustration of an expandable implant.

FIGS. 4-5 illustrate example exploded parts views of an expandable implant 100. Implant 100 may include a superior endplate 10 and an inferior endplate 20, for example. The superior and inferior endplates 10, 20 may be adjustable with respect to one another in the vertical direction and inclinable with respect to one another, i.e., capable of distraction and lordosis. Additionally, in some embodiments, superior and inferior endplates 10, 20 may also be able to tilt side to side and provide lateral stability and/or sagittal balance.

The superior endplate 10 may include a first bone screw aperture 13 extending through the upper surface of superior endplate 10 for engaging with a superior vertebrae, for example. In the example illustration, the first bone screw aperture 13 extends from the proximal end 100p of superior endplate 10 and inferior endplate 20 includes a bone screw cutout 23 to accommodate the angle of attack, and/or bone screw trajectory, of bone screw aperture 13, for example. Superior endplate 10 may include and/or define a superior portion of gripping channel 101. For example, superior gripping channels 101s. Similarly, superior endplate 10 may include a superior portion of bone screw guide aperture. For example, superior bone screw guide aperture 103s.

The inferior endplate 20 may include a second bone screw aperture 21 extending through the lower surface of inferior endplate 20 for engaging with an inferior vertebrae, for example. In the example illustration, the second bone screw aperture 21 extends from the proximal end 100p of inferior endplate 20 and superior endplate 10 may include a bone screw cutout 11, at least in some embodiments. Inferior endplate 20 may include and/or define an inferior portion of gripping channel 101. For example, inferior gripping channels 101i. Similarly, inferior endplate 20 may include an inferior portion of screw guide aperture 103. For example, inferior bone screw guide aperture 103i. The interior of inferior endplate 20 may include a threaded core 25 extending from an interior proximal wall to a medial support structure 26, for example. In various embodiments, the interior of medial support structure 26 may also be threaded and define the distal end of threaded core 25, for example.

The interior components of implant 100 may include a locking mechanism for fixing the relative position of the superior and inferior endplates 10, 20, for example. The locking mechanism may include a threaded set screw 50 having an outside circumferential surface including a thread pattern 51. Set screw 50 may be disposed in threaded core 25 and move forward and backward in the proximal/distal directions upon rotation of the set screw 50. For example, set screw 50 may include an internal circumferential surface 52 having any suitable size and shape for engaging with a driver to rotate set screw 50. For example, a hexolobular shape, a torx shape, a hex shape, polygonal, etc. In various embodiments, the set screw 50 may include a central aperture 53 extending therethrough; although, in some embodiments a distal end of set screw 50 may be closed. In at least one embodiment, a distal end of set screw 50 is closed and an outside distal surface of set screw 50 may have a hemispherical and/or cup like shape that is indented or outdented.

The locking mechanism may include a proximal saddle 40 and a distal saddle 60, for example.

As shown best in FIG. 5, proximal saddle 40 may include a spherical end cap 45 on the proximal end of implant for nesting within the central aperture 53 of set screw 50. This geometry allows proximal saddle 40 to freely incline and decline vertically and move side to side laterally while remaining frictionally engaged and in direct contact with a distal end of set screw 50, for example Additionally, this connection may allow for set screw 50 rotate and tighten while remaining engaged with the proximal saddle 40 regardless of the orientation of proximal saddle 40. Proximal saddle 40 may include a post 43 extending from the distal end of proximal saddle 40 towards the distal end 100d of implant 100, for example. Post 43 may be symmetrically disposed in a center of the distal end of proximal saddle 40 and include any suitable shape, e.g., a circular post, a square post, hexaganol post, etc. Post 43 may nest within crossbar 15 of superior endplate 10 (see FIG. 10) as will be explained in further detail below. Distal saddle 60 may include a ramp 61 and/or curved surface at the proximal end thereof. For example, an arcuate surface arcing in the proximal-to-distal direction from the distal end 100d towards the proximal end 100p. The distal surface 62 of distal saddle 60 may be substantially planar, for example. However, in some embodiments, the distal surface of distal saddle 60 may include surface texturing for increasing a coefficient of friction and facilitating a locked and or fixed engagement with an adjoining surface. For that matter, any of the various disclosed components of the locking mechanism may selectively include high friction surfaces and/or low friction surfaces.

Figure 6:
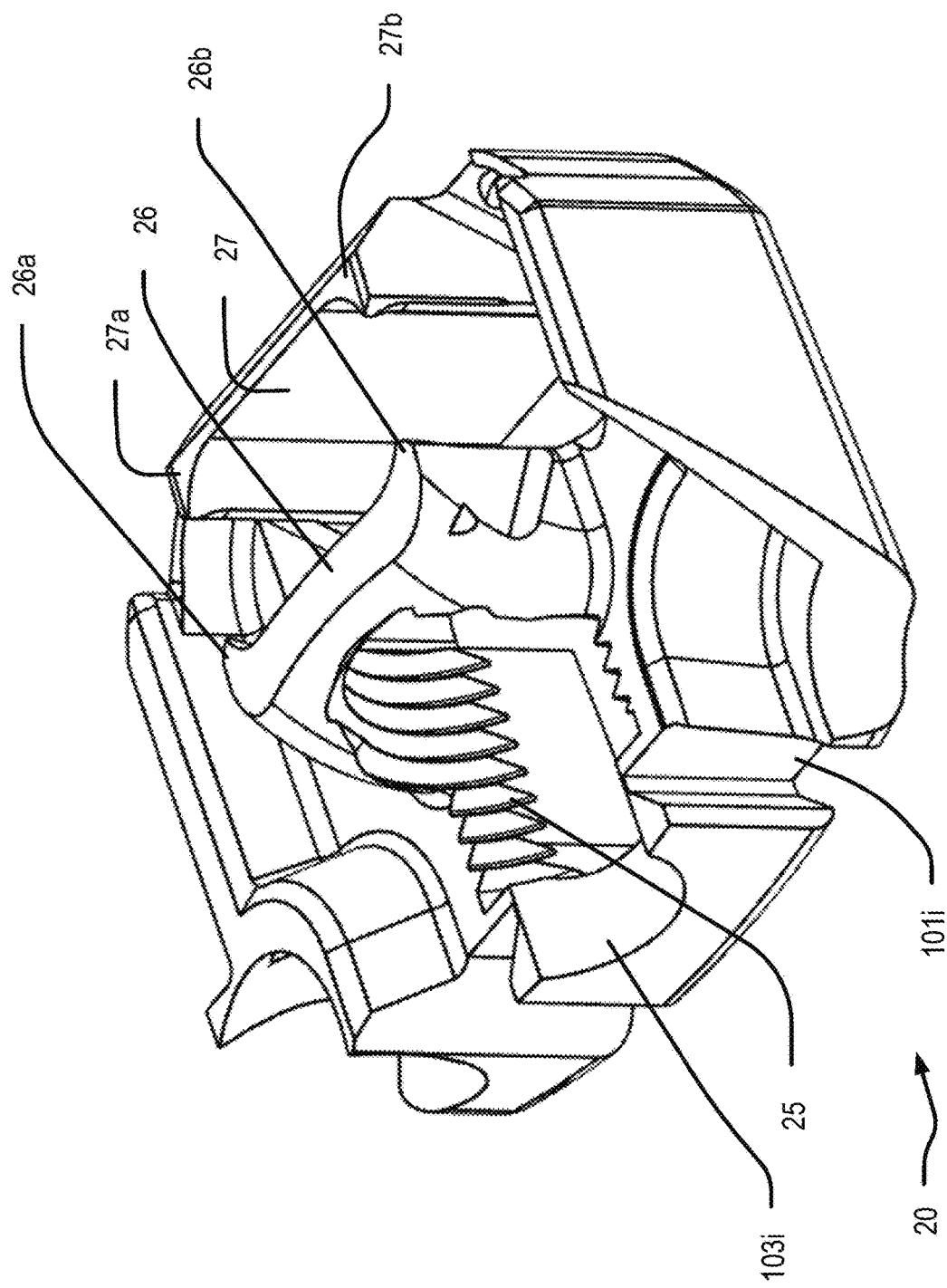
FIG. 6 is a perspective view of the inside of an inferior endplate.
Figure 7:
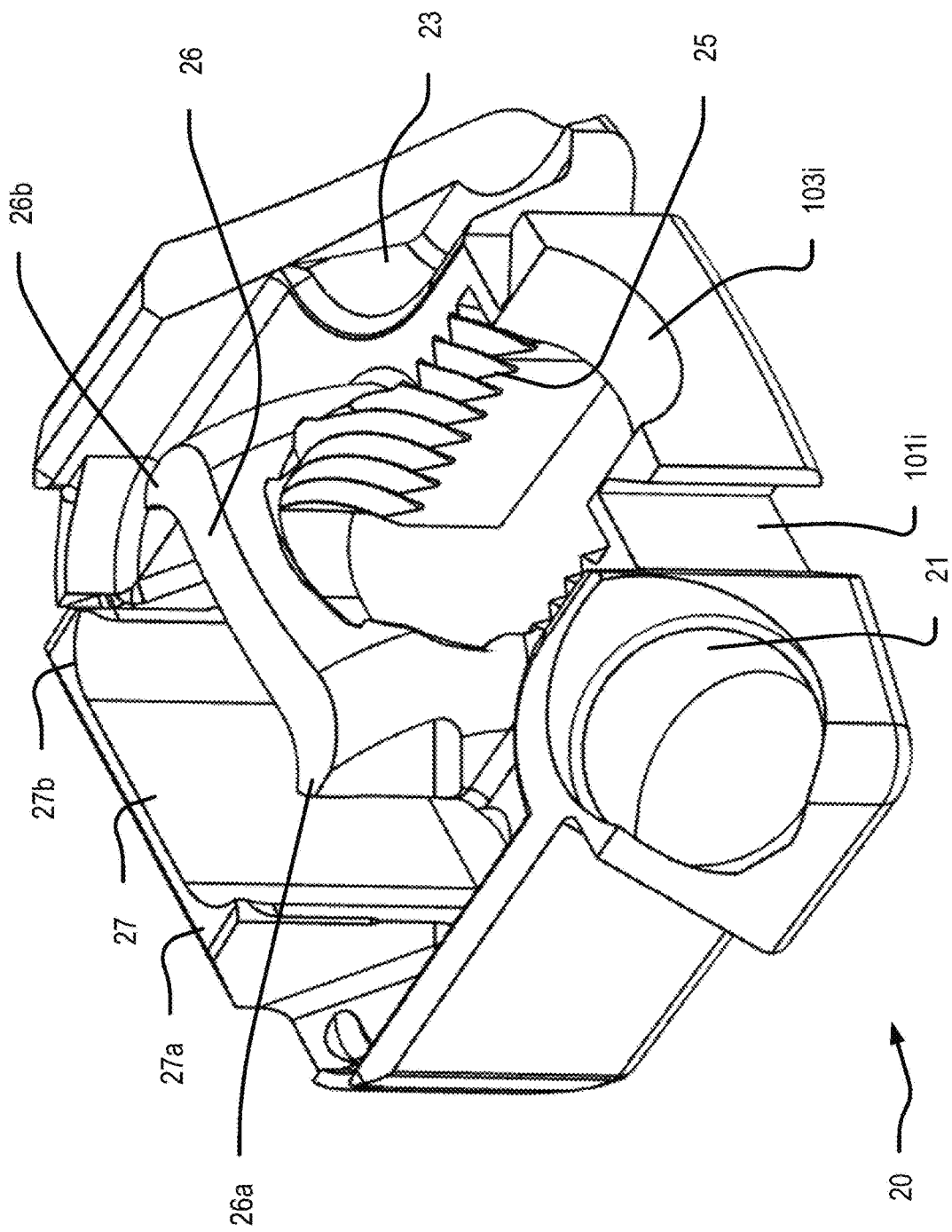
FIG. 7 is an alternate perspective view of the inside of an inferior endplate.
Figure 8:
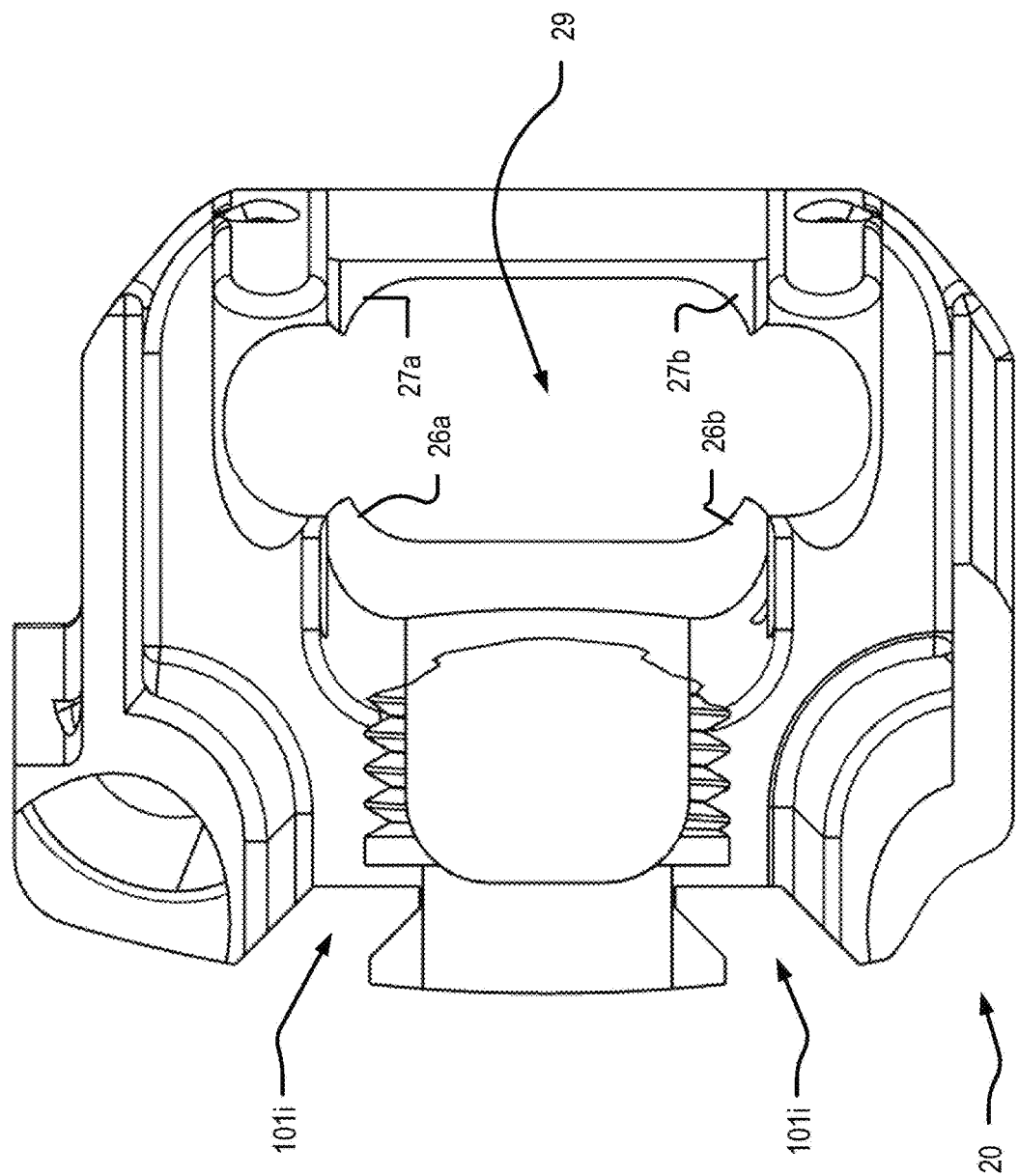
FIG. 8 is a top down view of the inside of an inferior endplate.

FIGS. 6-8 are various views of the inside of an inferior endplate 20. As illustrated, the inside of inferior endplate 20 may include a threaded core 25 extending in a proximal-to-distal direction between an inside proximal face of the inferior endplate 20 to a medial support structure 26, for example. The medial support structure 26 may be disposed in a medial position relative to the proximal end 100p and distal end 100d although the term "medial" does not imply and/or require an absolute centered location. The medial support structure may be shaped like an arch or the like and include a substantially planar top surface, a first tang 26a and a second tang 26b (left and right tang) on the lateral sides of the medial support structure 26, for example. Similarly, the inside distal surface 27 of inferior endplate 20 may include a third tang 27a and a fourth tang 27b (left and right tang). Tangs 26a and 26b may face the distal surface 27 and curve inward with respect to the longitudinal axis A-A, for example. Tangs 27a and 27b may face the proximal end 100p of implant 100 and curve inward with respect to the longitudinal axis A-A, for example. The inwardly curving tangs may facilitate the retention and alignment of components therein, some of which may include corresponding curved surfaces and/or be freely floating, for example. The space between the medial support structure 26 and distal surface 27 may be referred to as a receiving cavity 29 for receiving various members of the locking mechanism and the crossbar 15 of superior endplate 10. In some embodiments, a beam may extend between medial support structure 26 and the inside distal surface 27 in the posterior-to-distal direction. For example, a beam extending from the top portion of medial support structure 26 to the inside distal surface 27 for increasing the rigidity of implant 100.

Figure 9:
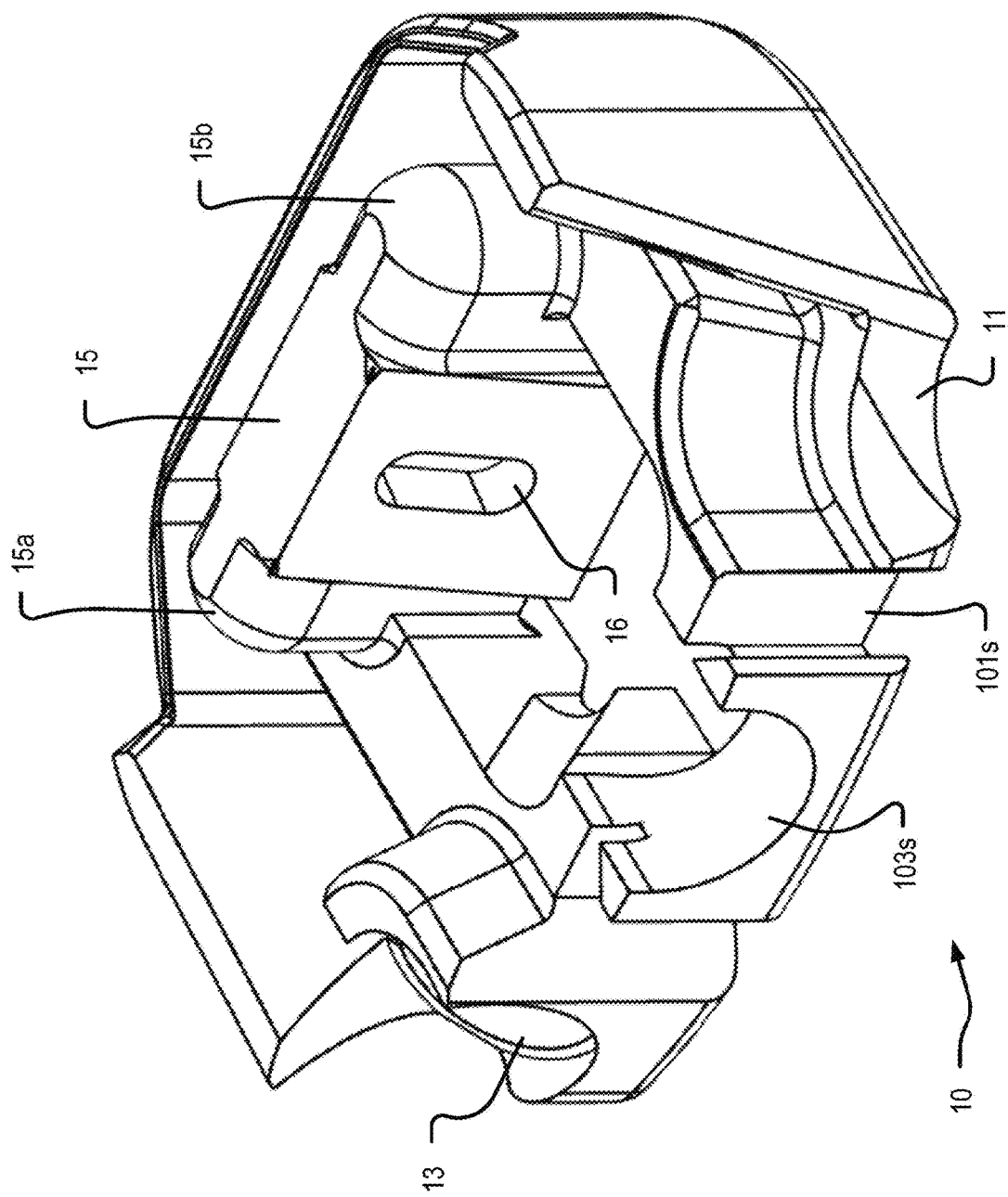
FIG. 9 is a perspective view of the inside of a superior endplate.
Figure 10:
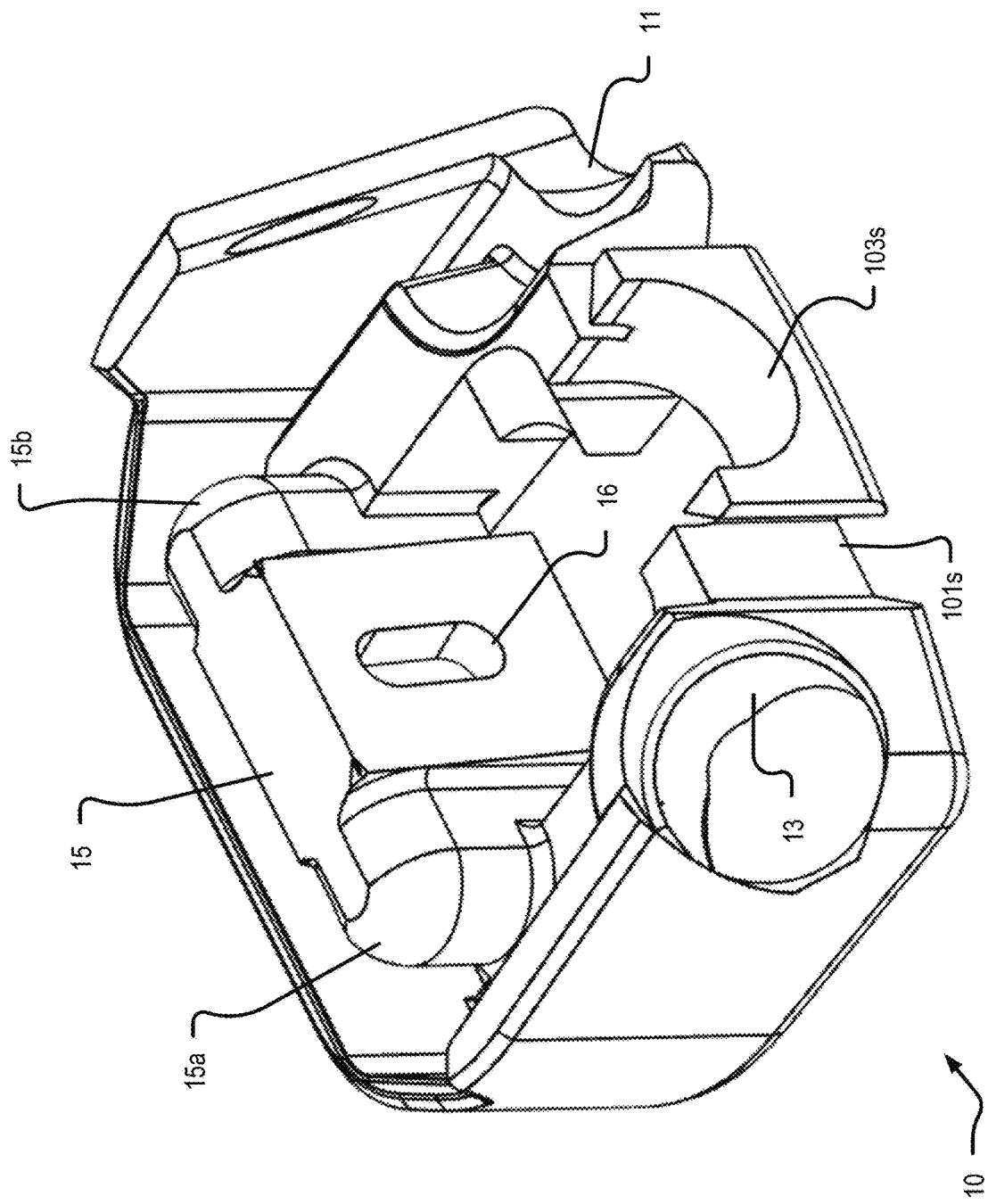
FIG. 10 is an alternate perspective view of the inside of a superior endplate.
Figure 11:
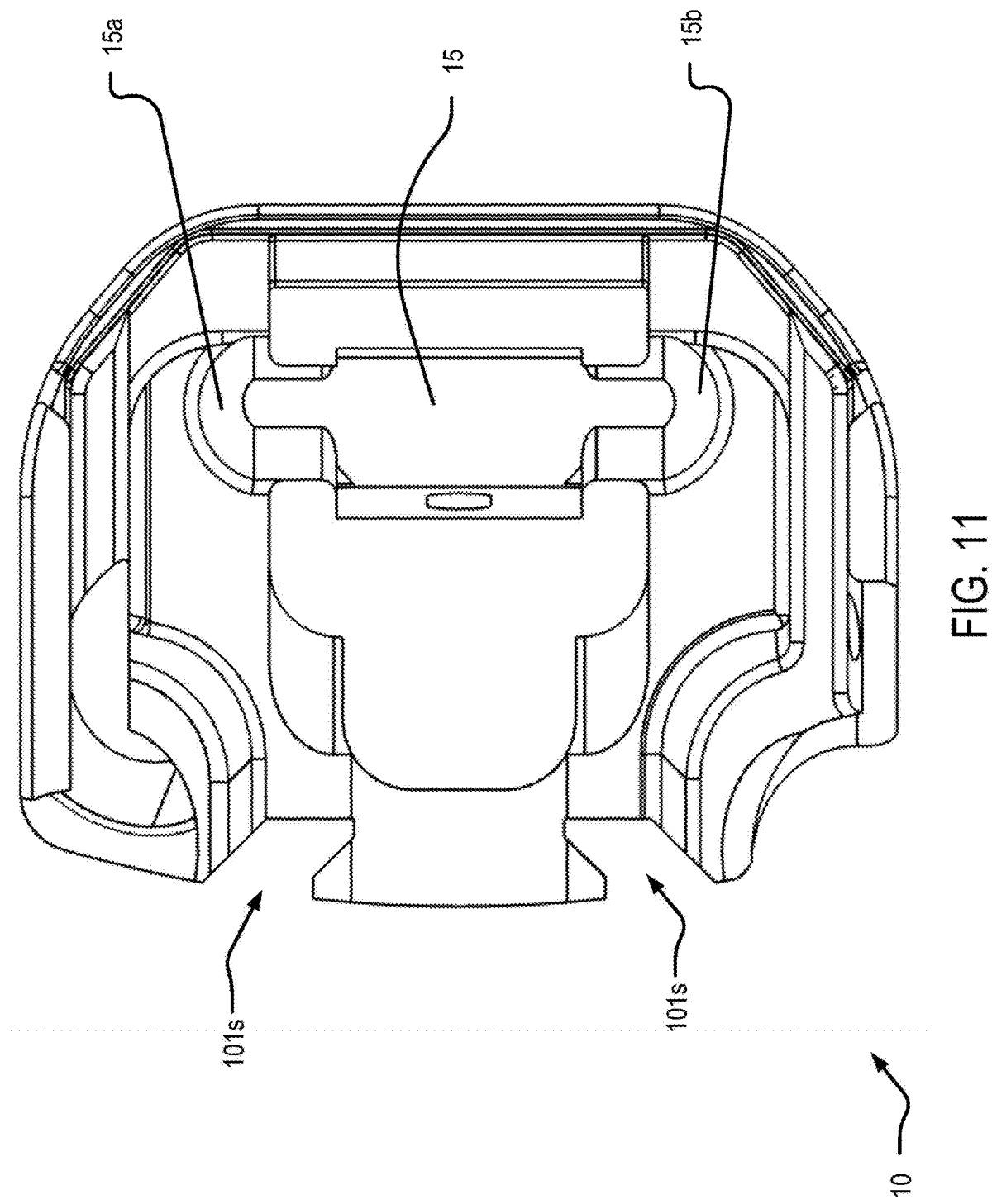
FIG. 11 is a top down view of the inside of a superior endplate.

FIGS. 9-11 are various view of the inside of a superior endplate 10. Superior endplate 10 may include a crossbar 15 extending in the widthwise direction that is disposed between inside lateral side surfaces of superior endplate 10 proximate a distal end of superior endplate 10, for example. In various embodiments, a bottom surface of crossbar 15 may be substantially planar and first lateral side 15a and second lateral side 15b may have an arcuate curved shape, for example First and second lateral sides 15a, 15b may be shaped like a portion of a dome and/or a cylinder. The proximal end of crossbar 15 may include a planar surface having a slot 16 such as an aperture or indentation therein, for example. In various embodiments, slot 16 may have a width in the widthwise direction and a height in the vertical direction and the height of slot 16 may be greater than the width, for example. In various embodiments, the height of slot 16 may about 2-3 times (or greater) than the width of slot 16 and may include top and bottom chamfered surfaces. As explained above, crossbar 15 may be disposed within receiving cavity 29 and slot 16 may receive post 43 such that post 43 may slide up and down in the vertical direction within slot 16.

Figure 12:
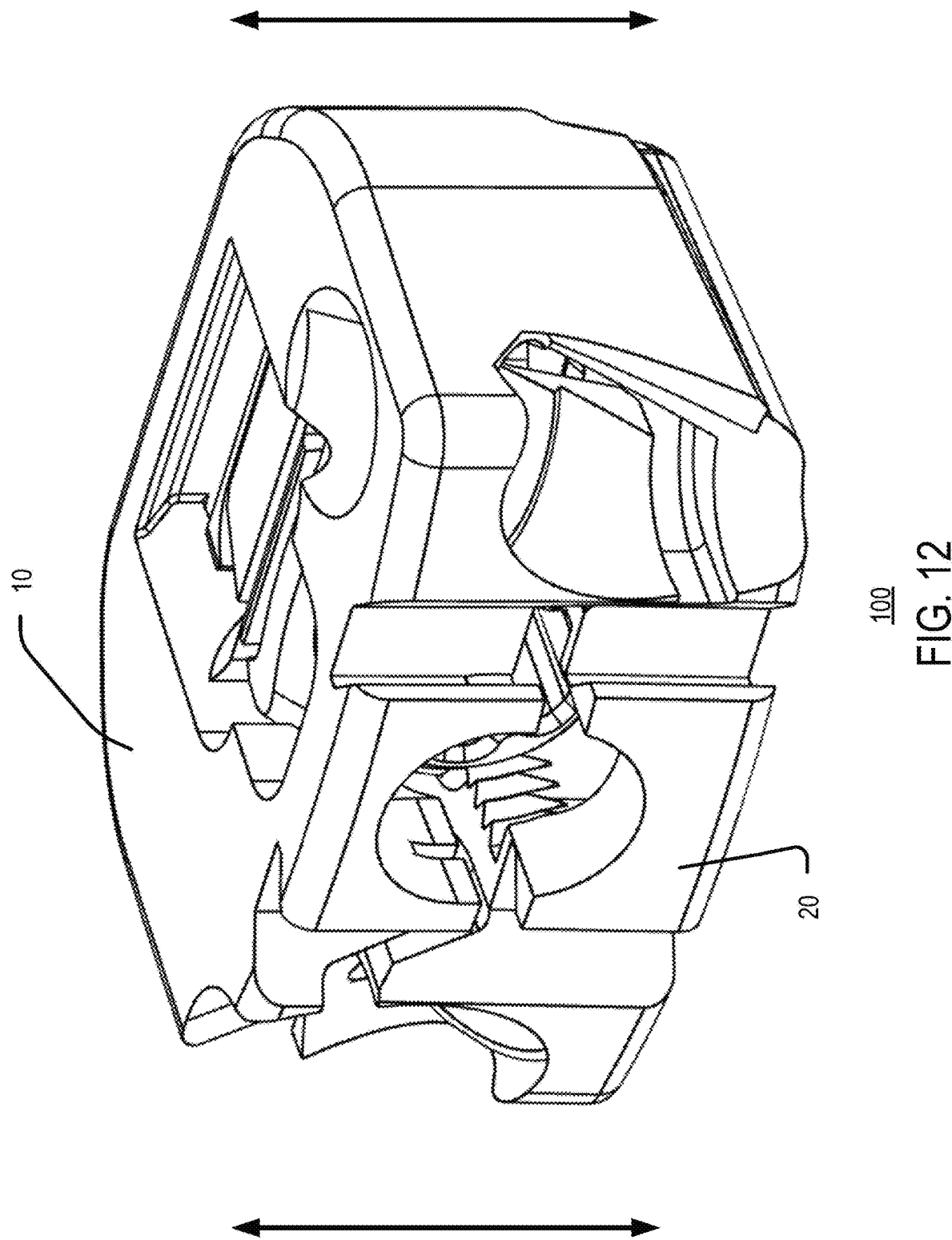
FIG. 12 is a perspective illustration of an expandable implant in a first expanded position.
Figure 13:
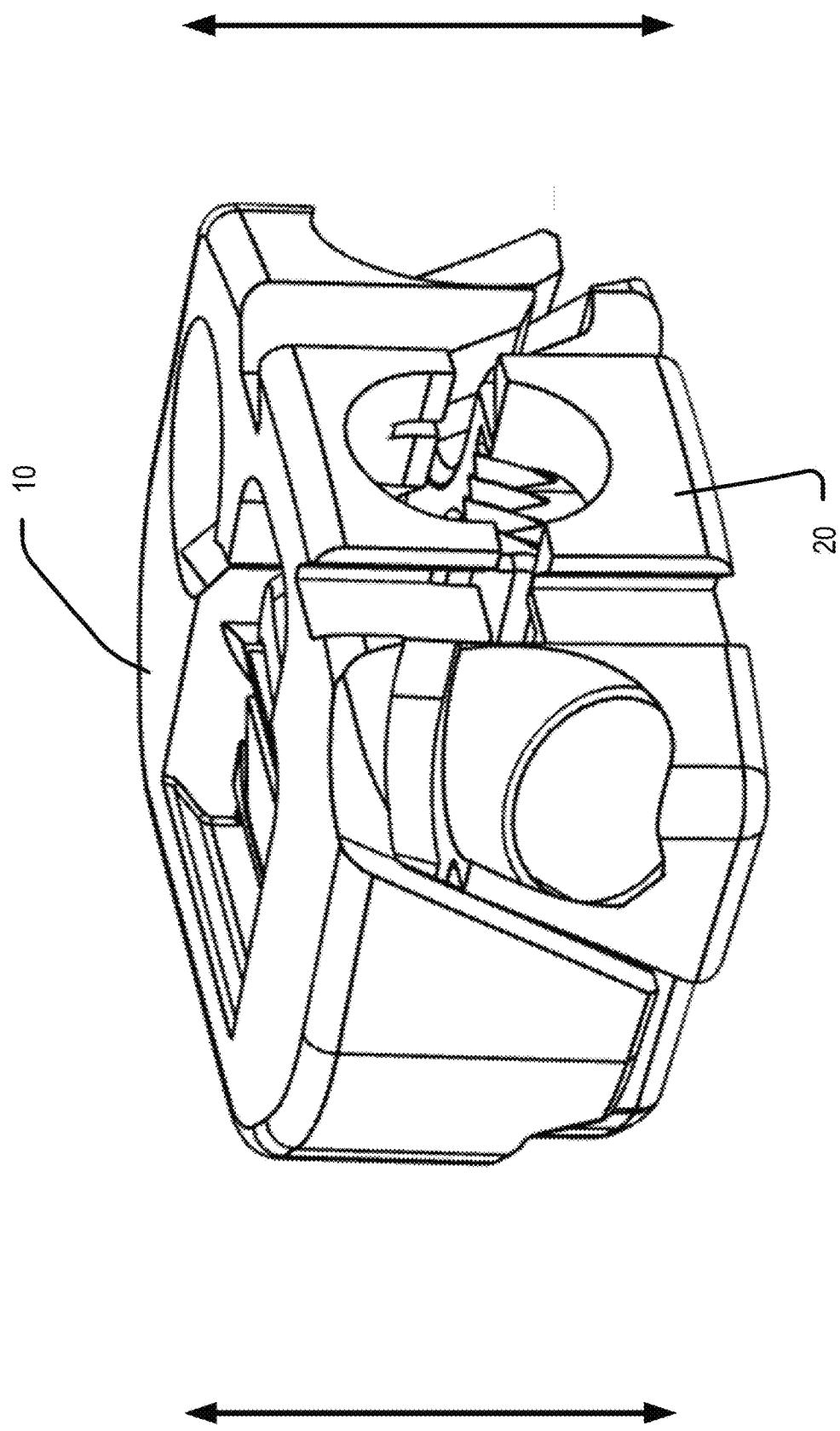
FIG. 13 is an alternate perspective illustration of an expandable implant in a first expanded position.

FIGS. 12-13 are perspective illustrations of expandable implant 100 in a first expanded position. In the first expanded position, the implant is distracted in a parallel manner such that the upper surface of the superior endplate 10 and the lower surface of the inferior endplate 20 are substantially planar. However, in other embodiments where the superior endplate 10 and inferior endplate 20 are convex the implant 100 may nonetheless expand to the first expanded position such that the superior endplate 10 is substantially vertically aligned with the inferior endplate 20, for example. For example, the proximal end 100p of implant defined by the superior endplate 10 and inferior endplate 20 is aligned even though the superior endplate 10 and or inferior endplate 20 are convex. Furthermore, an initial expansion of implant 100 may be any combination of distraction and lordosis. For example, the implant 100 may expand in a vertical direction and be inclined with respect to the vertical direction.

Figure 14:
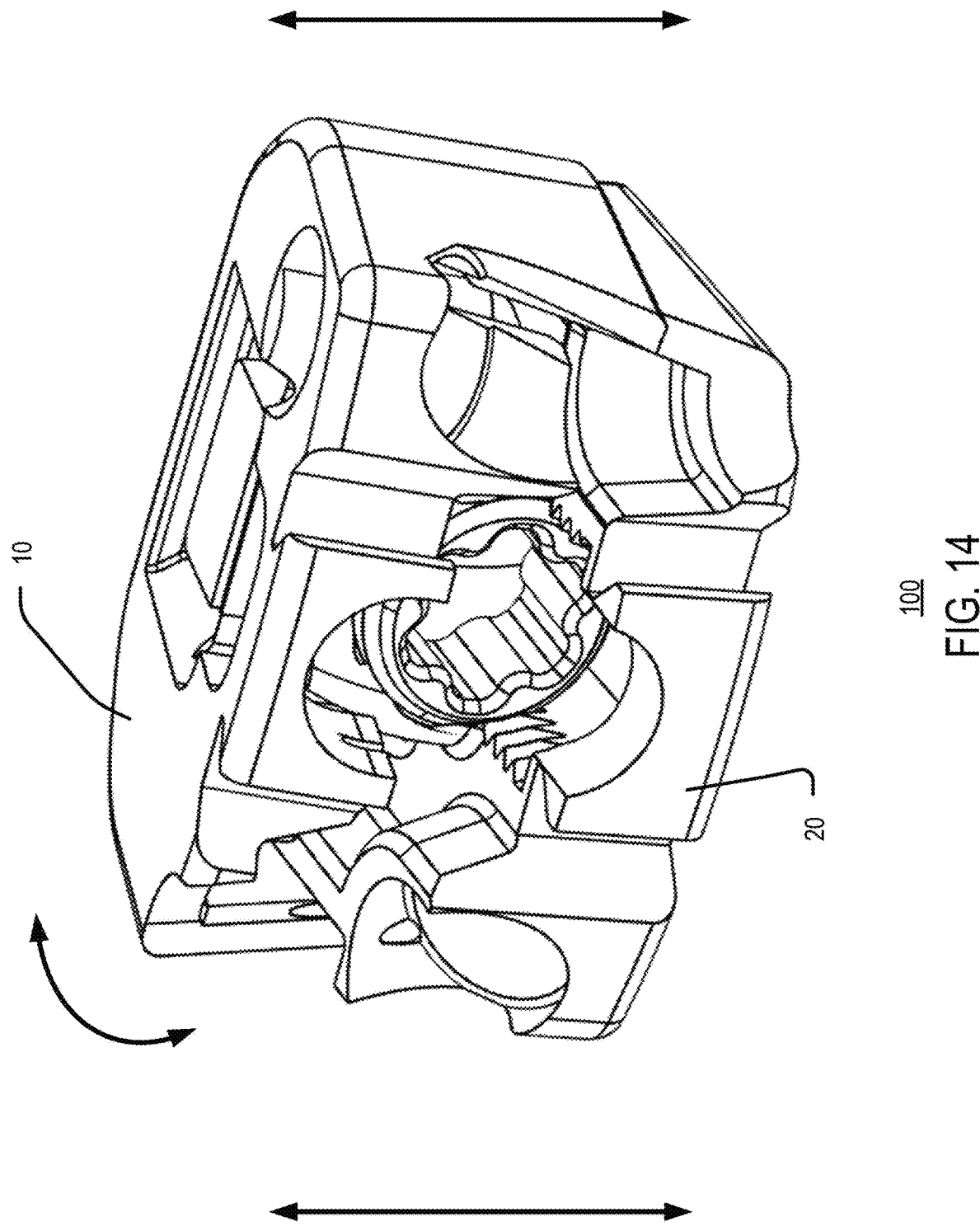
FIG. 14 is a perspective illustration of an expandable implant in a second expanded position.
Figure 15:
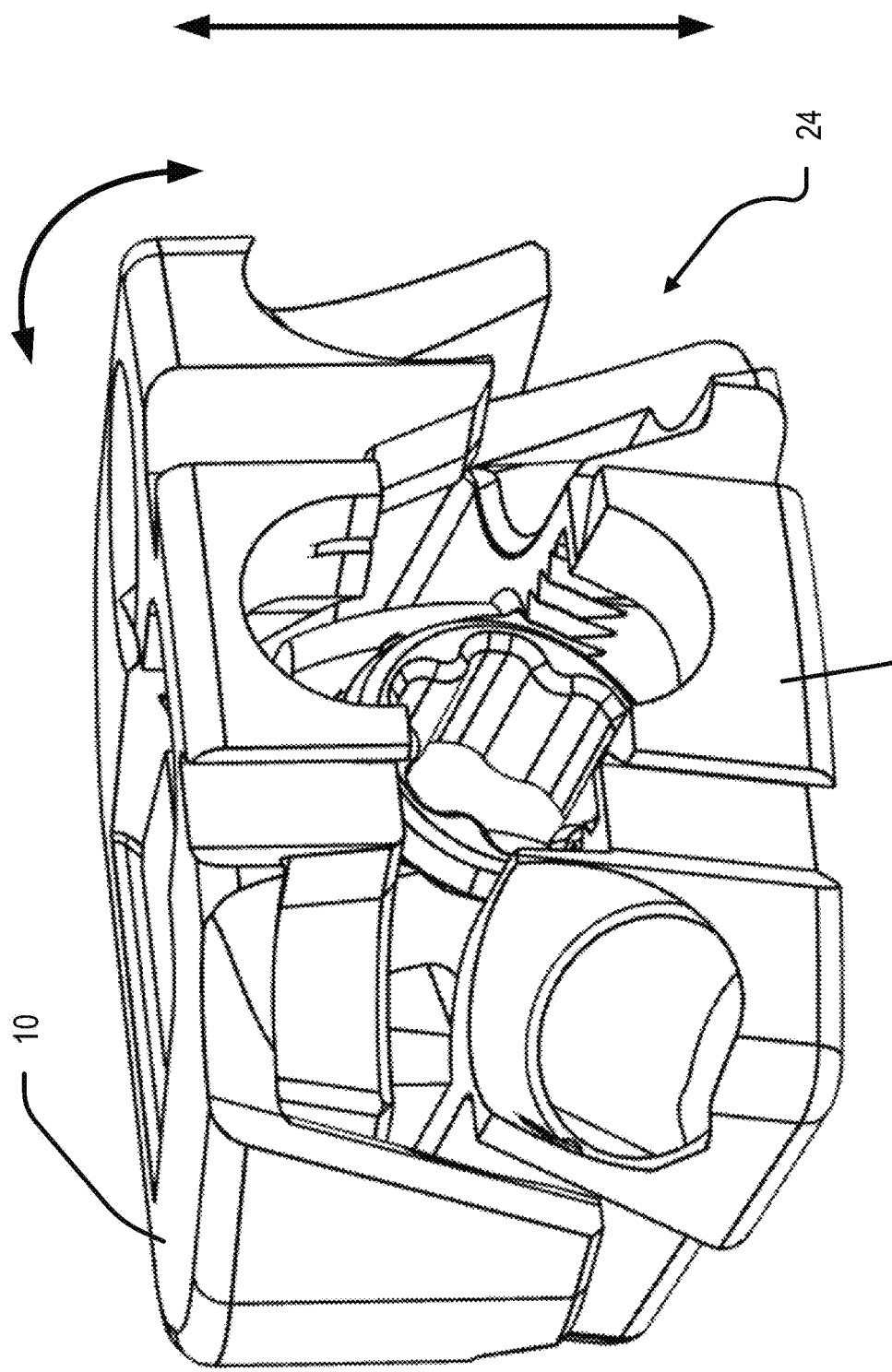
FIG. 15 is a perspective illustration of an expandable implant in a second expanded position.

FIGS. 14-15 are perspective illustrations of an expandable implant 100 in a second expanded position. In the second expanded position, the implant 100 is distracted and lordosed. For example, a relative height of the implant 100 between the top surface of superior endplate 10 and bottom surface of inferior endplate 20 is greater than in the contracted configuration (fully collapsed position). Additionally, the upper surface of the superior endplate 10 is inclined with respect to the lower surface of the inferior endplate 20, for example. In the second expanded configuration, a relative height and angle of inclination between the superior and inferior endplates 10, 20 is greater than a relative height and angle of inclination in the collapsed position. In some embodiments, the superior and inferior endplates 10, 20 may be inclined with respect to one another in the collapsed position, and the angle of inclination in the second expanded configuration will be greater than the original angle of inclination in the collapsed position.

Figure 16:
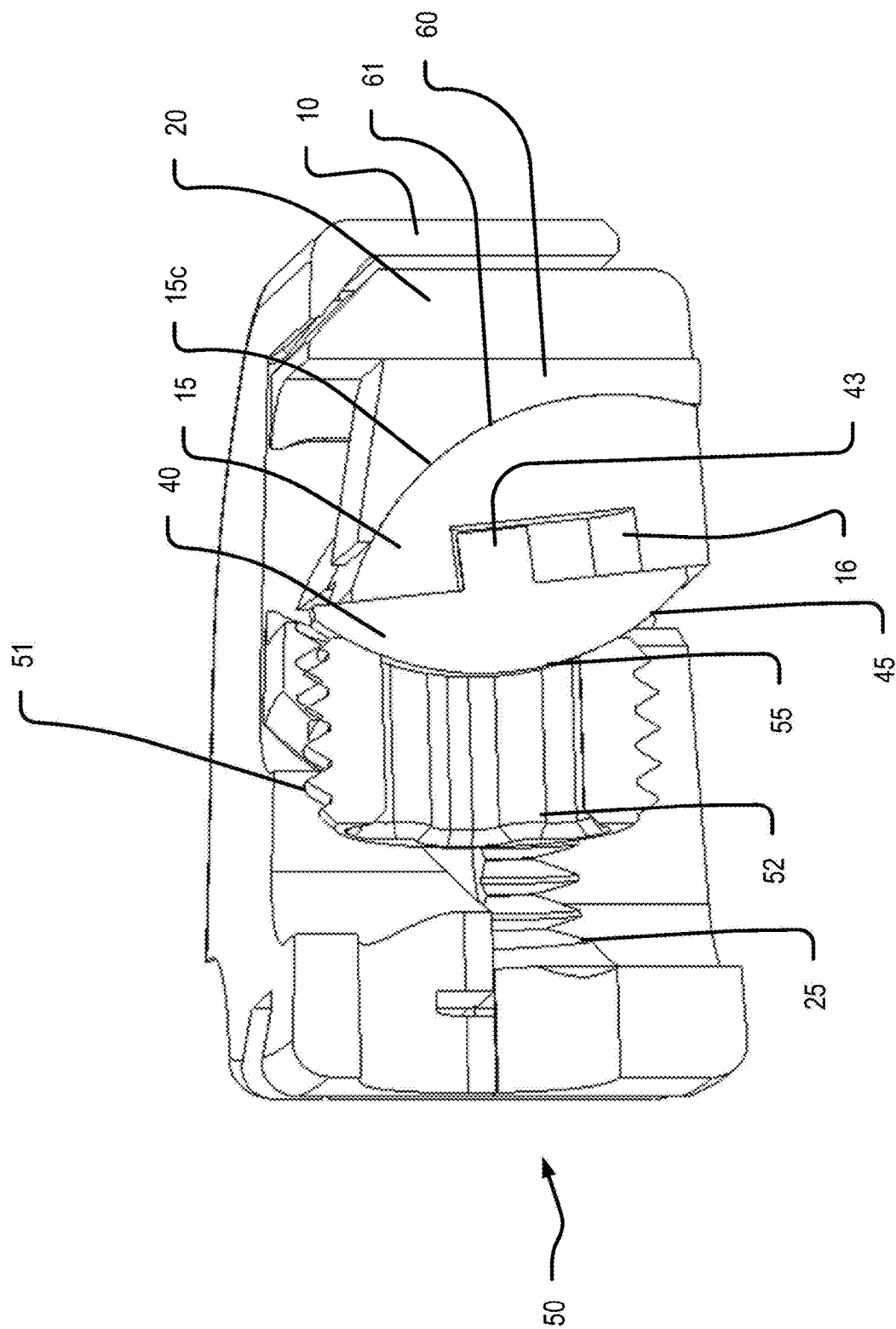
FIG. 16 is a cross section view of an expandable implant in a contracted position through line A-A of FIG. 3.

FIG. 16 is a cross section view of implant 100 in a contracted position through longitudinal axis A-A of FIG. 3. In the example illustration, it is shown that the set screw 50 is in a medial position within the threaded core 25. In this embodiment, the distal end of the set screw 50 includes a curved bearing surface 55 and a hollow core. The curved bearing surface 55 and hollow core allow the proximal saddle 40 to slide across bearing surface 55 in the vertical direction while being in direct contact, for example Set screw 50 may push and/or compress proximal saddle 40 towards the distal end 100d of implant 100 by directly contacting it. For example, set screw 50 pushes a free floating proximal saddle 40 towards crossbar 15 such that post 43 pushes into slot 16 and directly engages with an upper portion of the interior surface of slot 16. Additionally, in the example embodiment, the distal surface of proximal saddle 40 acts against the proximal surface of crossbar 15 by directly engaging with it. In turn, the crossbar 15 pushes against the curved proximal surface 61 of distal saddle 60 and pushes, applies a force against, and/or compresses distal saddle 60 against the distal interior surface of inferior endplate 20. For example, the distal saddle 60 may be a free floating element having a curved surface with a size and shape corresponding to the size and shape of the adjacent curved surface of crossbar 15. In this way, implant 100 is in a locked position where set screw 50 pushes, applies a force against, and/or compresses proximal saddle 40 into crossbar 15 which in turn pushes, applies a force against, and/or compresses distal saddle 60 against the interior distal surface of inferior endplate 20. In the locked position, a relative position of the superior endplate 10 and inferior endplate 20 may be fixed such that a relative height and inclination of the superior endplate 10 and inferior endplate 20 are fixed and/or immovable due to components 50, 40, 45, and 60, directly contacting one another in series with a sufficient compressive force that the superior endplate 10 is locked with respect to the inferior endplate 20.

Figure 17:
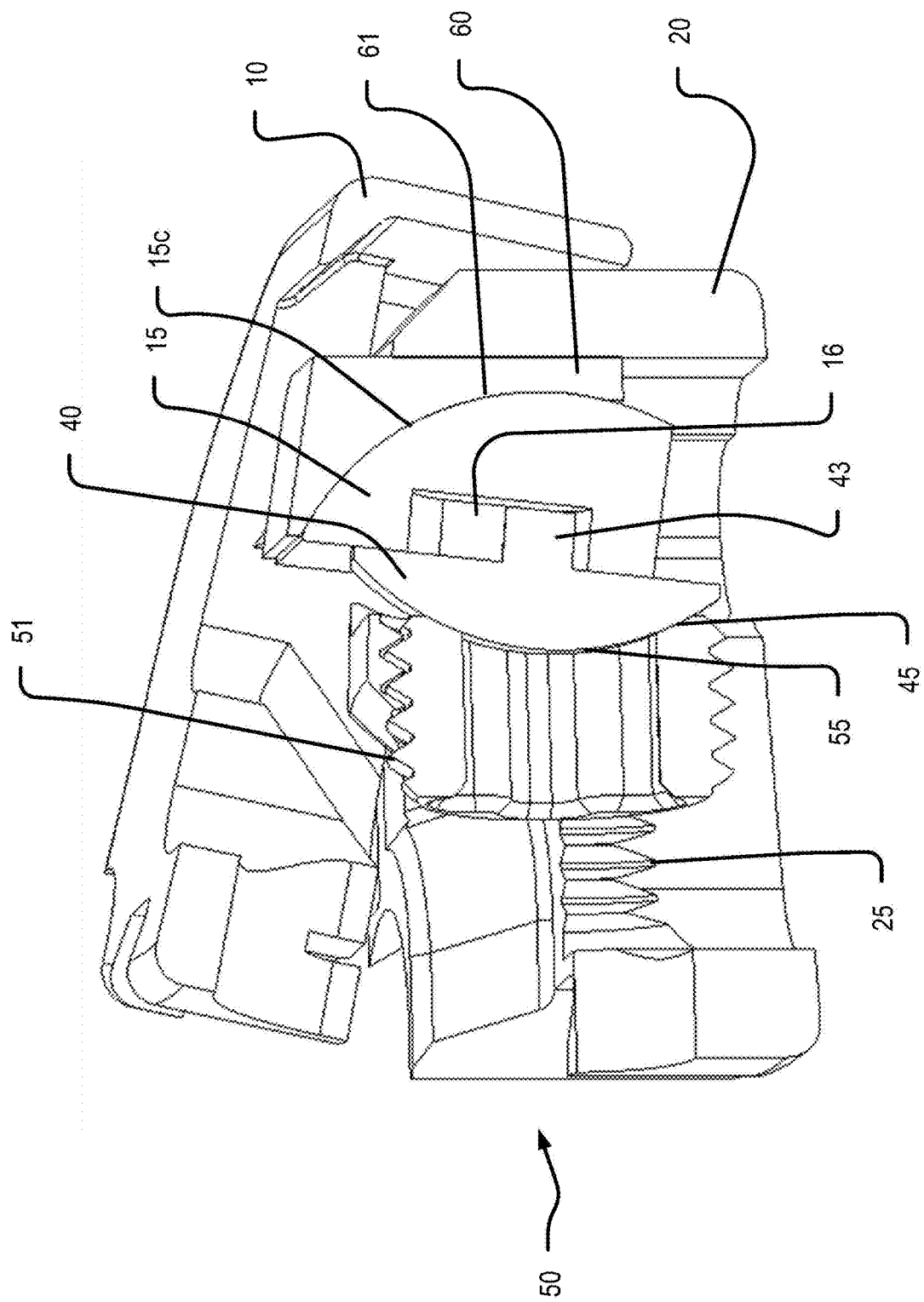
FIG. 17 is a cross section view of an expandable implant in an expanded position through line A-A of FIG. 3.
Figure 18A:
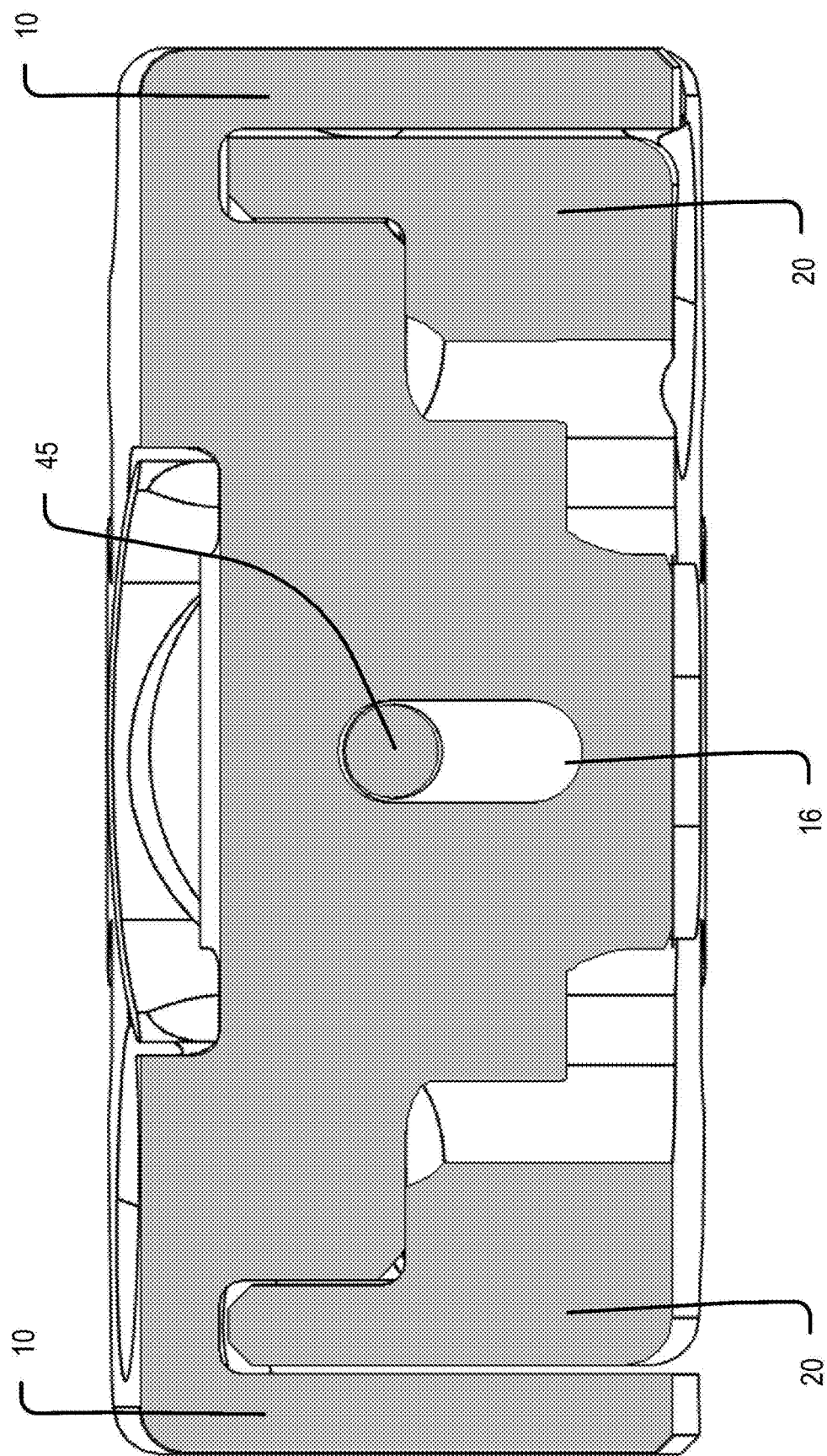
FIG. 18A is a cross section view of an expandable implant in a contracted position through line C-C of FIG. 3.
Figure 18B:
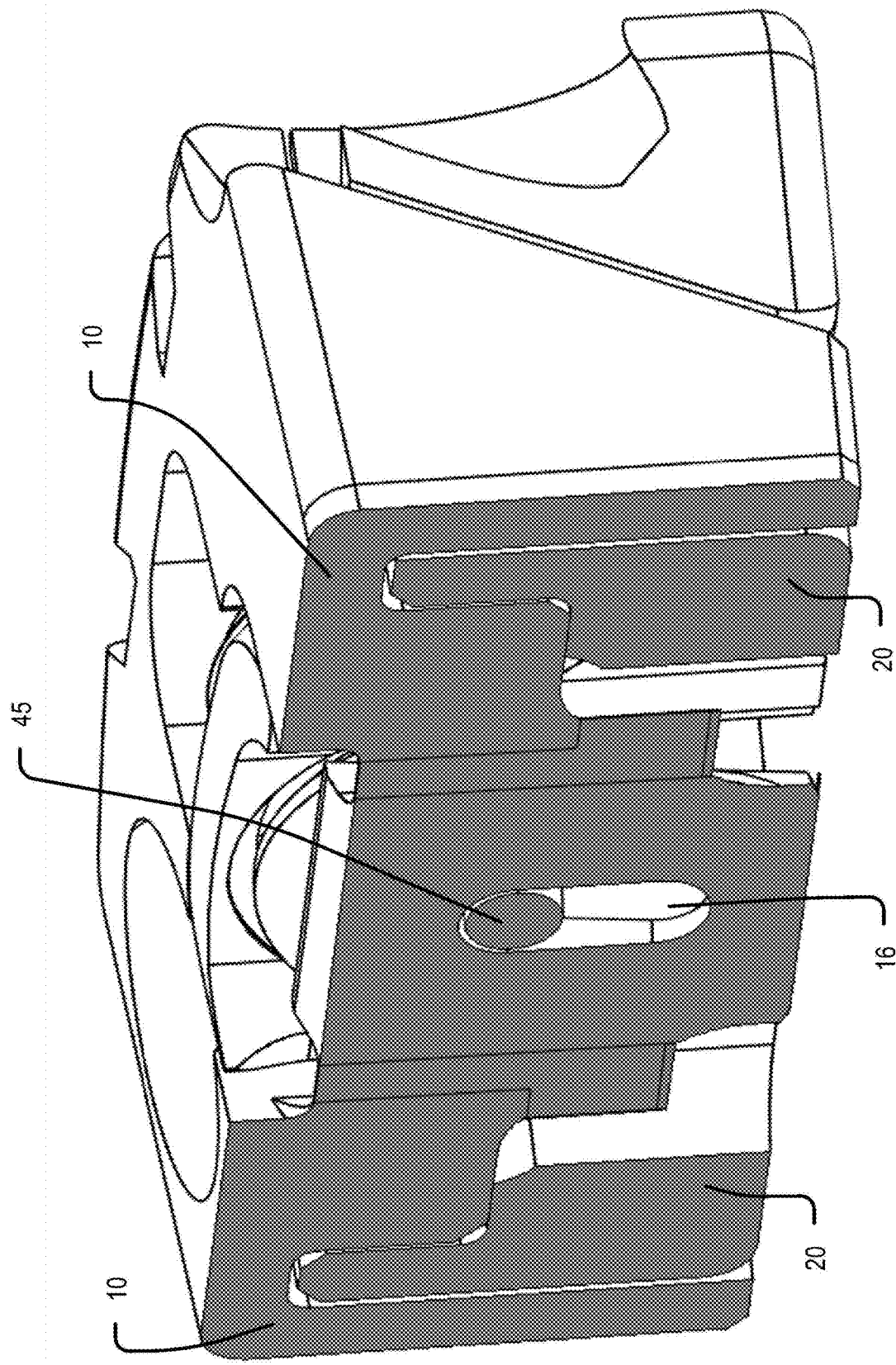
FIG. 18B is a perspective cross section view of an expandable implant in a contracted position through line C-C of FIG. 3

FIG. 17 is a cross section view of implant 100 in an expanded position through line A-A of FIG. 3 where implant 100 is expanded and inclined (distracted and lordosed). FIG. 17 illustrates a similar locked arrangement to FIG. 16 and fixes the relative position of the superior and inferior endplates 10, 20 similarly as explained above. However, in the example illustration the proximal saddle 40 and crossbar 15 have rotated towards the distal end 100d (relative to FIG. 16). The crossbar 15 has rotated in this way because the superior endplate 10 is inclined with respect to the inferior endplate 20. By inclining the superior endplate 10, the crossbar 15 urges the proximal saddle 40 to rotate and this rotation is facilitated by post 43 sliding within slot 16 from an upper position within slot 16 (FIG. 16) to a lower position within slot 16 (FIG. 17), for example Additionally, due to crossbar 15 rotating the distal saddle 60 is pushed upward in the vertical direction due to the interaction between the curved proximal surface 61 and the curved distal surface 15c of crossbar 15.

In some embodiments, as set screw 50 is tightened against proximal saddle 61 set screw 50 may urge proximal saddle 61 upwards vertically, at least partly, such that a superior surface of proximal saddle 61 pushed against the underside of superior endplate 10, for example. This may partly open implant 100 and/or provide a supporting force to superior endplate 10 preventing and/or suppressing the collapse from an expanded position to a contracted position, for example Additionally, and depending on the relative orientation of proximal saddle 61, an axis of rotation of saddle 61 may be lower than the rotation axis of set screw 50 and in those relative orientations tightening of the set screw 50 against proximal saddle 61 may push proximal saddle 61 upwards in the vertical direction. In some embodiments, a spring or biasing mechanism may be provided that initially pushes the locking mechanism together (not illustrated) such that when the implant 100 is initially opened it retains its shape, at least to some extent, in the expanded configuration until such a time that the set screw 50 may be fully tightened. Other relative motion of these components may not be described herein because it is immediately apparent to those with skill in the art.

FIGS. 18A and 18B are cross section views of an expandable implant 100 in a contracted position through line C-C of FIG. 3, which passes through crossbar 15. In the example illustration, it is shown that the post 43 is seated within an upper portion of the slot 16 and the crossbar 15 is integrally formed as a portion of superior endplate 10. Additionally, the superior endplate 10 and inferior endplate 20 may be in a nested relationship. For example, the outside side surfaces of the inferior endplate 20 are nested within the inside side surfaces of superior endplate 10. This nested relationship may be beneficial for lateral stability of implant 100. In some embodiments, a gap may exist in the nested relationship such that some lateral bending is allowed, e.g., about 1-5 degrees. Furthermore, in various embodiments the superior endplate 10 and inferior endplate 20 may not be coupled together by an actuator and/or hinge such that superior endplate 10 may separate from the inferior endplate 20 in the vertical direction. For example, in various embodiments a relative position of the superior endplate 10 and inferior endplate 20 may only be fixed and/or secured due to tightening the set screw 50 against the proximal saddle 40, crossbar 15, distal saddle 60, and distal interior surface of inferior endplate 20. This arrangement may be advantageous because it reduces the number and size of internal components within implant 100 which increases the relative amount of internal space for bone grafts, bone growth promoting materials (BGM), and the like. Additionally, this nested relationship may be beneficial for providing walls to retain a BGM like material in the interior of implant 100.

Figure 19:
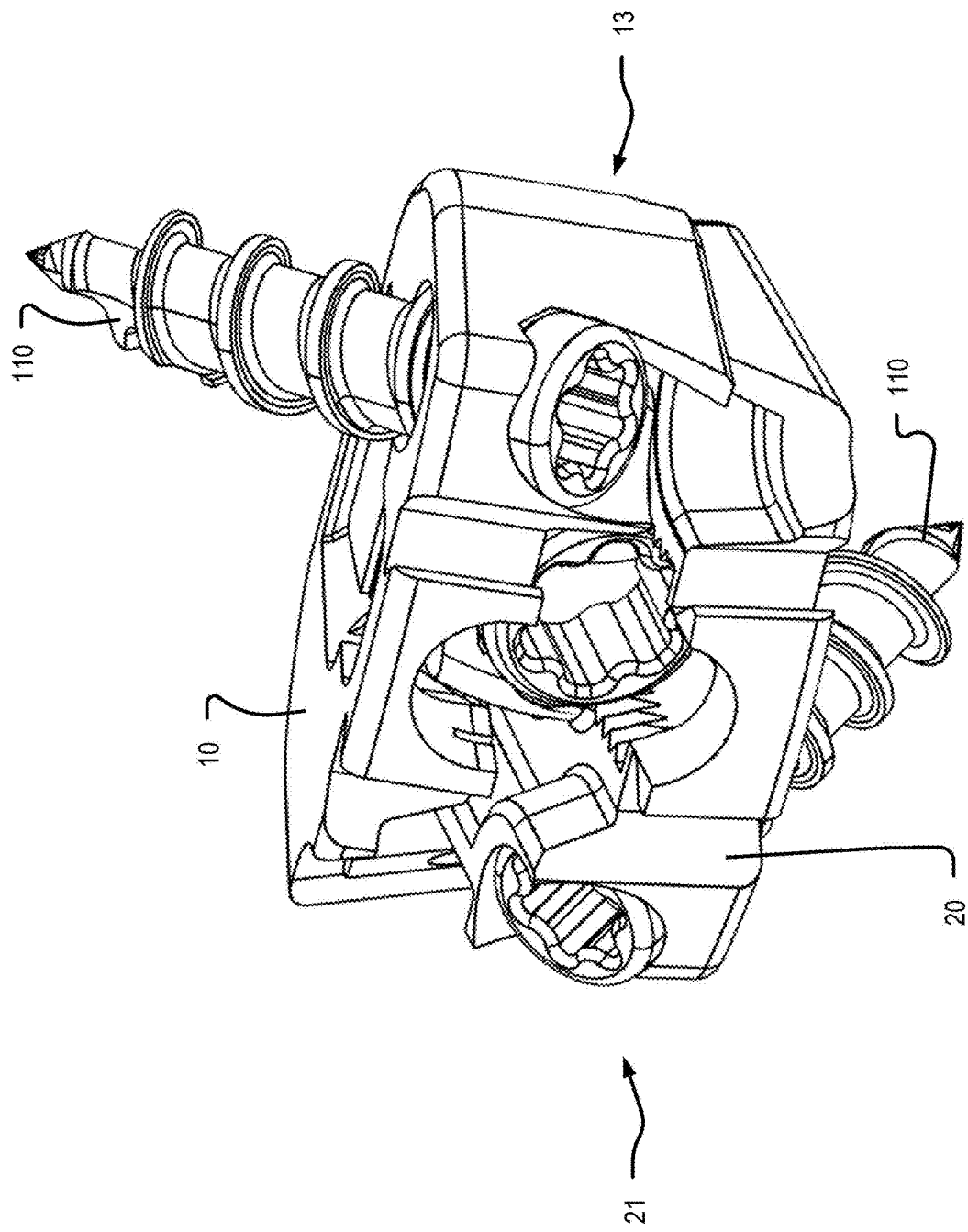
FIG. 19 is a perspective view of an expandable implant with bone screws.
Figure 20:
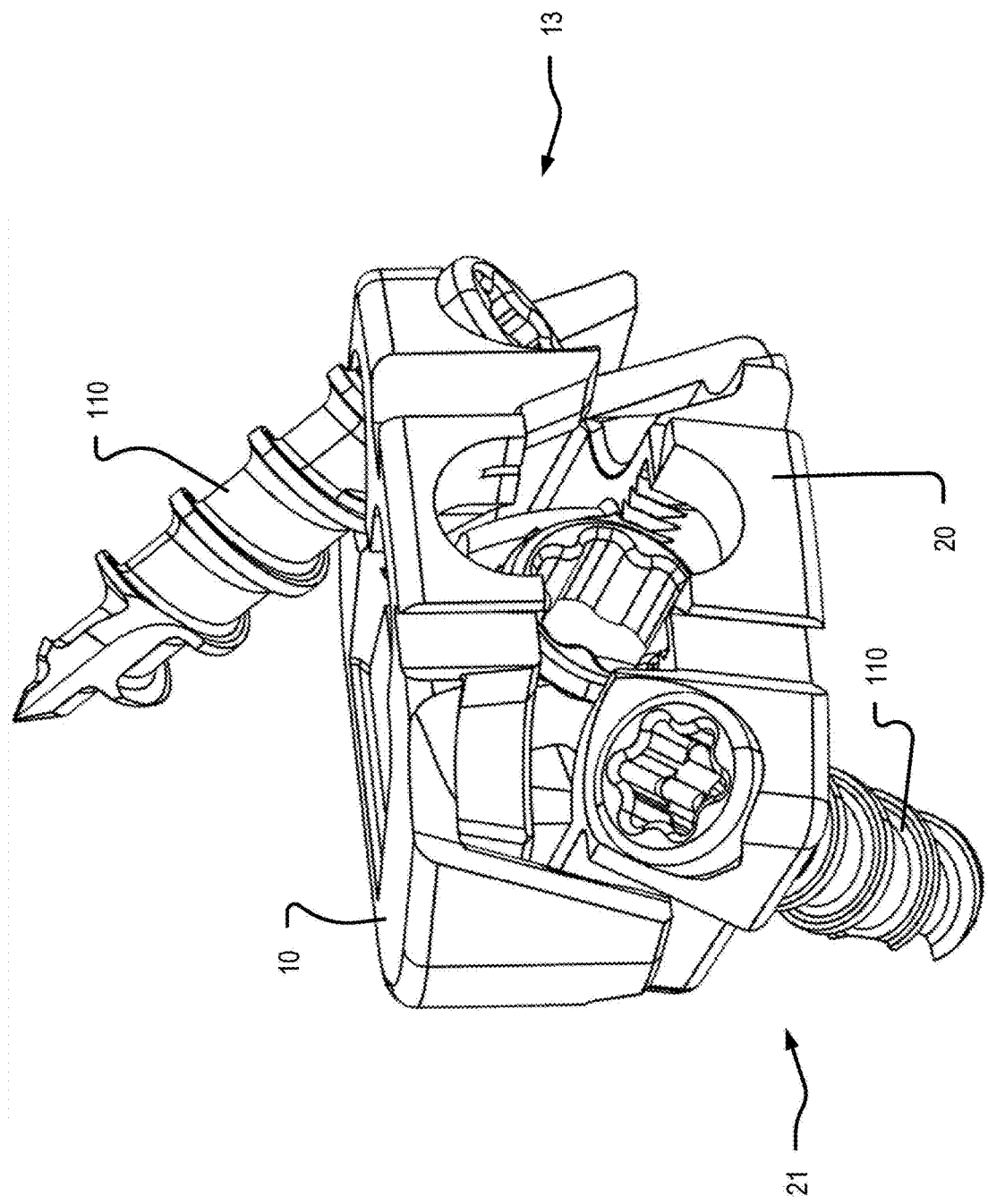
FIG. 20 is an alternate perspective view of an expandable implant with bone screws.

FIGS. 19-20 are various views of an expandable implant 100 with bone screws 110. In the example embodiment, bone screws 110 extend through bone screw apertures 13, 21 of the superior endplate 10 and inferior endplate 20, respectively. For example, bone screw aperture 13 aligns bone screw 110 in a target trajectory such that it extends through an upper surface of superior endplate 10 from a proximal end 100p towards a distal end 100d. Additionally, bone screw aperture 13 may align bone screw 110 in a target trajectory such that it also extends from a lateral side surface towards the center of the implant, i.e., bone screw 110 converges towards the longitudinal axis. Similarly, bone screw aperture 21 aligns bone screw 110 in a target trajectory such that it extends through a lower surface of inferior endplate 20 from a proximal end 100p towards a distal end 100d. Additionally, bone screw aperture 21 may align bone screw 110 in a target trajectory such that it also extends from a lateral side surface towards the center of the implant, i.e., bone screw 110 converges towards the longitudinal axis A-A. This arrangement may be advantageous for securing implant between a superior vertebrae and an inferior vertebrae such that bone screws 110 are installed in a converging pattern within the vertebrae. In some embodiments, the target trajectory and length of bone screws may be chosen such that they only penetrate the cortical bone, for example. It shall be understood that various embodiments may include additional bone screw apertures that converge or even diverge from the longitudinal axis. Some embodiments may not include bone screws and/or bone screw apertures and rely on a textured engagement surface and/or other protruding engagement elements on the upper and lower surfaces of the superior and inferior endplates 10, 20, respectively. Such engagement surfaces may engage with adjacent vertebrae while a fusion process occurs over time.

Figure 21:
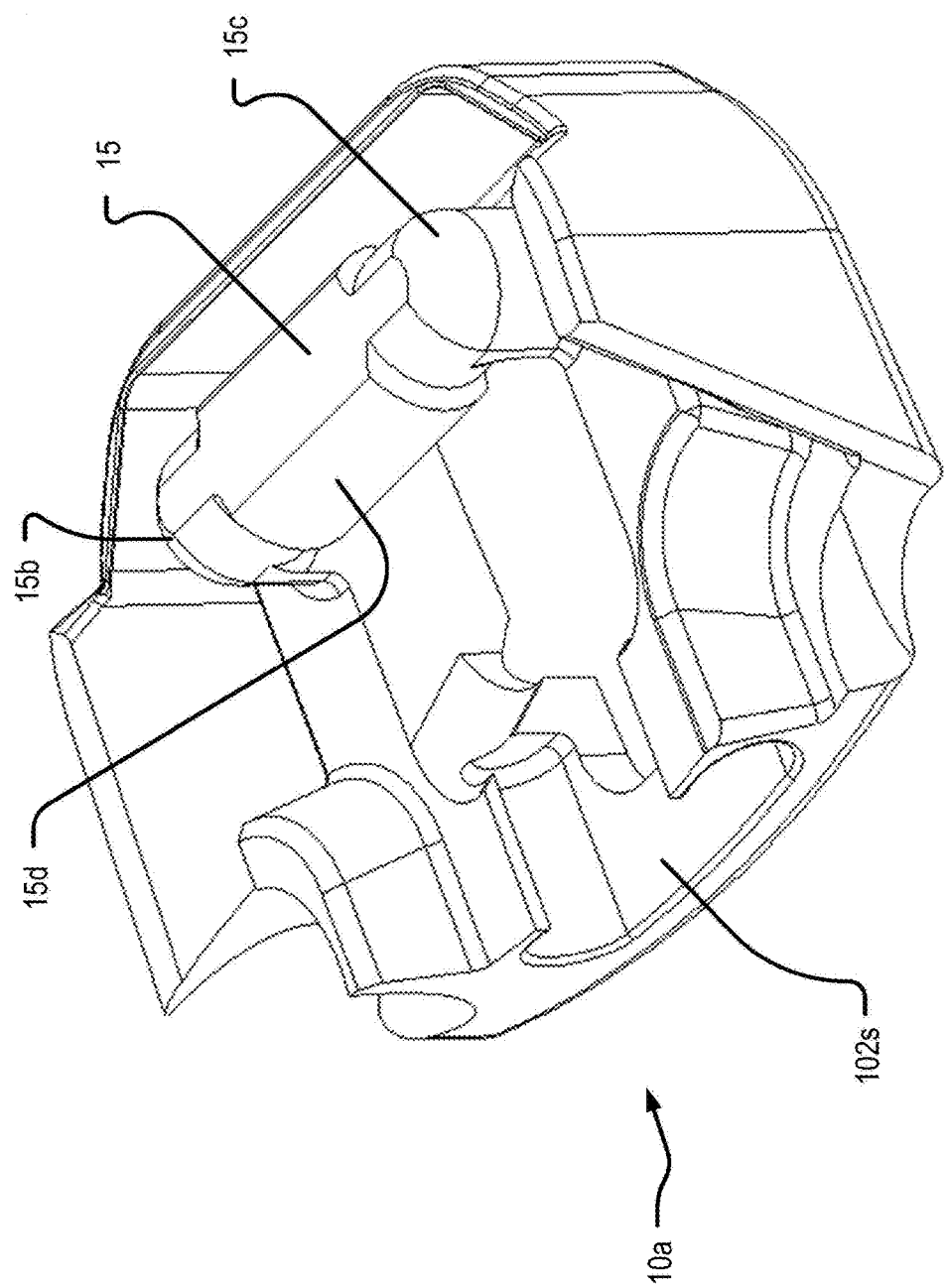
FIG. 21 is a perspective view of a superior endplate including a curved crossbar.

FIG. 21 is a perspective view of an alternate superior endplate 10a. Alternate superior endplate 10a may include the same, substantially the same, and or similar attributes as explained above with respect to superior endplate 10. For example, alternate superior endplate 10a may include a curved crossbar 15 and have a planar bottom surface and curved ends 15a, 15b as explained above. Crossbar 15 may include a distal curved surface 15c and a proximal curved surface 15d, for example. Additionally, alternate superior endplate 10a may include an alternately shaped gripping channel 102s extending horizontally on the proximal surface of alternate superior endplate 10a. For example, an indented horizontal channel with chamfered and/or rounded ends.

Figure 22:
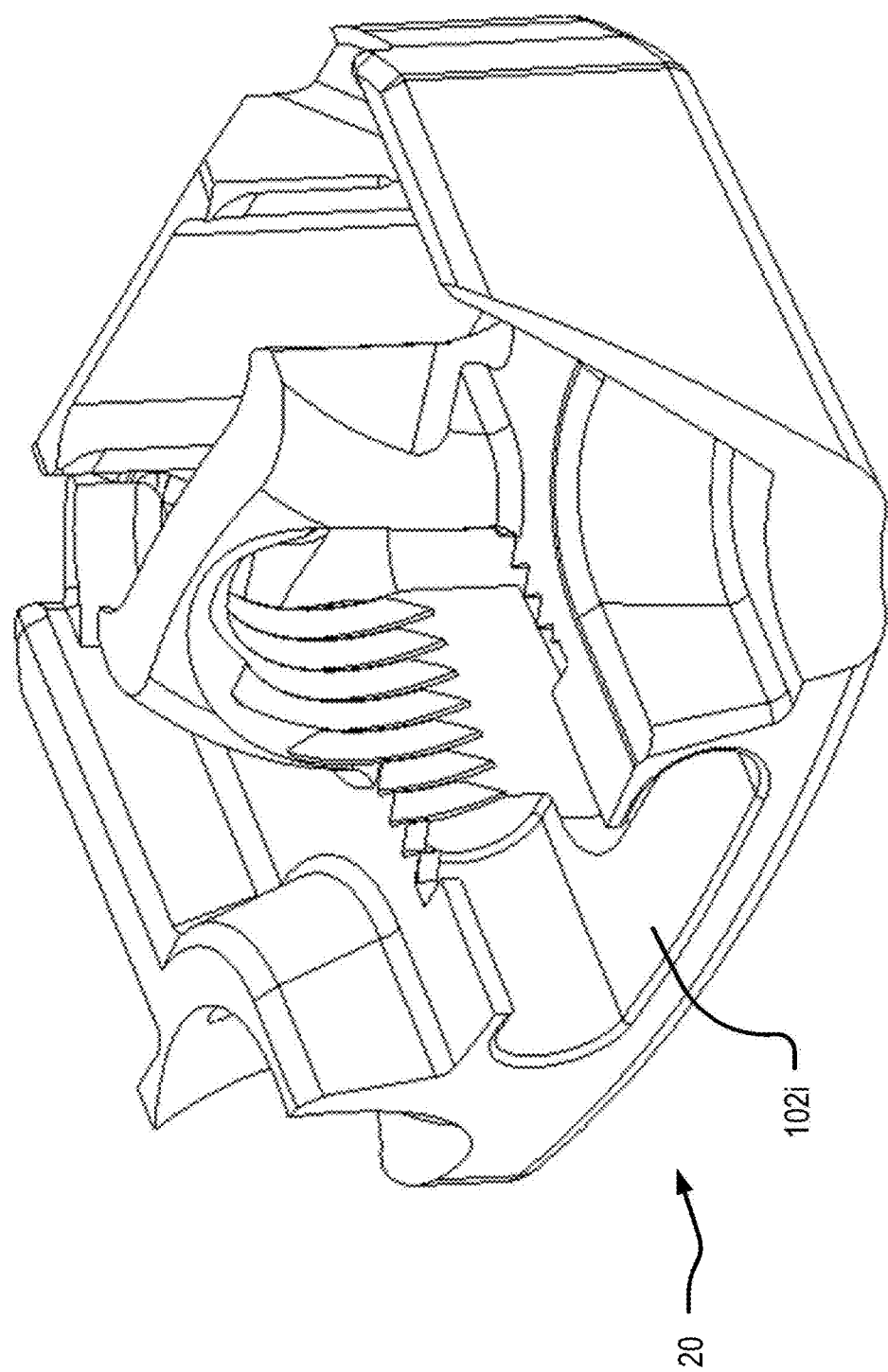
FIG. 22 is perspective view of an inferior endplate.

FIG. 22 is perspective view of an alternate inferior endplate 20a. Inferior endplate 20a may include the same, substantially the same, and/or similar attributes as explained above with respect to inferior endplate 20. Additionally, alternate inferior endplate 20a may include an alternately shaped gripping channel 102i extending horizontally on the proximal surface of inferior endplate 20a. For example, an indented horizontal channel with chamfered and/or rounded ends.

Figure 23:
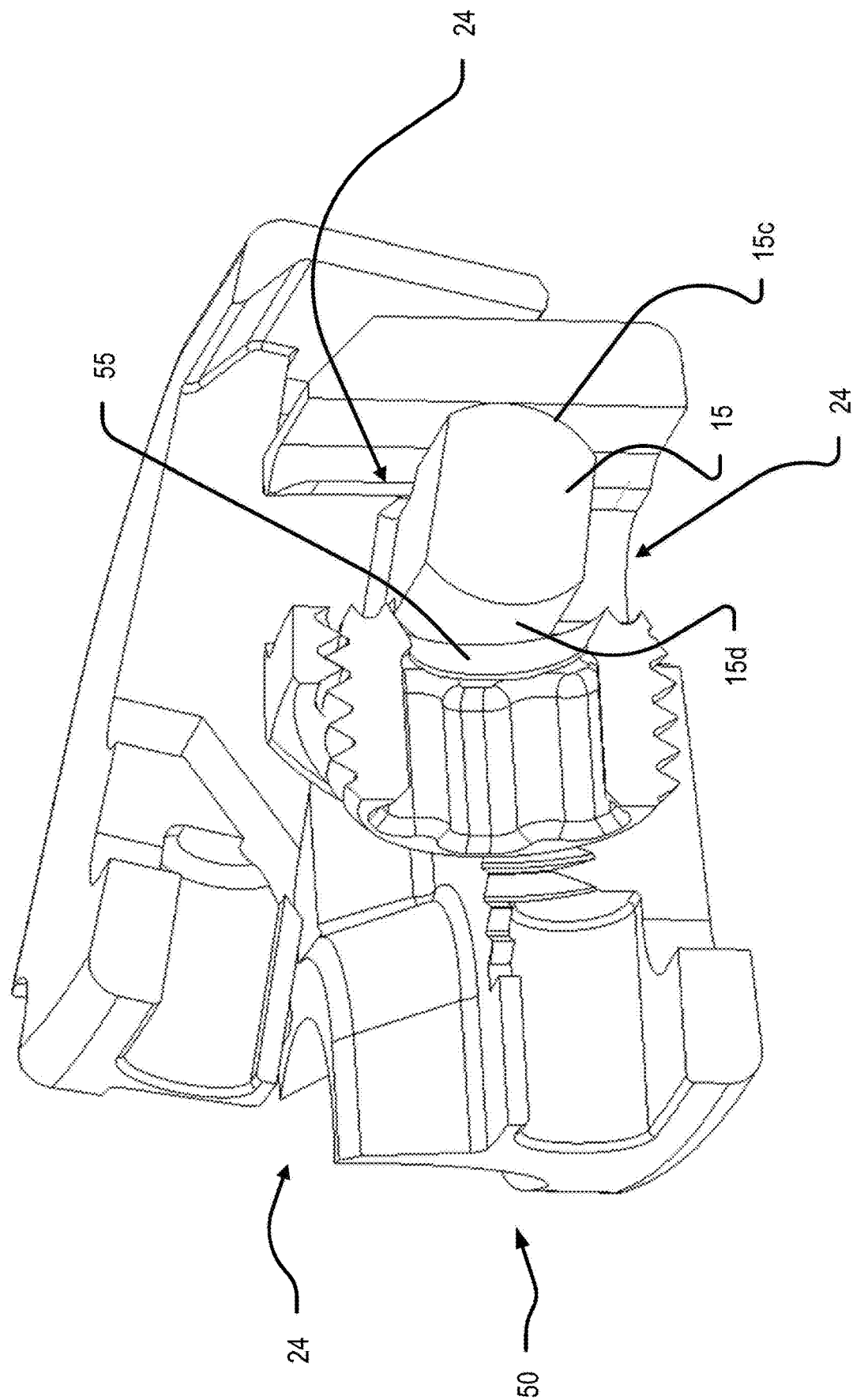
FIG. 23 is a cross section view of an expandable implant including the superior endplate of FIG. 21 and the inferior endplate of FIG. 22.

FIG. 23 is a cross section view of an expandable implant 100 including the alternate superior endplate 10a and the alternate inferior endplate 20a. In the example illustration, and due to the curved surfaces 15c, 15d of crossbar 15 the proximal saddle 40 and distal saddle 60 may be optional and/or not required for locking the alternate superior endplate 10a and alternate inferior endplate 20a together. In this embodiment, the set screw 50 includes a curved portion 55 at a distal end thereof that directly contacts the proximal curved surface 15d of crossbar 15. When the set screw 50 is moved towards a medial position similarly as explained above the set screw 50 may act against and/or compress crossbar 15 against the inside distal surface of the inferior endplate 20a. The compression of crossbar 15 of alternate superior endplate 10a against the inside distal end surface of inferior endplate 20a may lock the superior and inferior endplates 10a, 20a such that they are immovable with respect to one another similarly as explained above. In some embodiments, set screw 50 may include ridges or teeth that bite into and/or compress into the cross bar 15 (not illustrated), for example.

FIGS. 24-28 are various views illustrating a first surgical tool 200 for use with disclosed expandable implants 100. In some embodiments, first surgical tool 200 may be referred to as an inserter and/or an expander and can perform both functions, for example. First surgical tool 200 may extend from a proximal end 200p to a distal end 200d. The first surgical tool 200 may include a superior handle 210 and an inferior handle 220 that are pivotally coupled at a first pivot point 201. First pivot point 201 may be a hinge comprising a pin extending through tabs and/or sidewalls of superior handle 210 and inferior handle 220, for example.

Inferior handle 220 may include a cutout portion 225 to accommodate a corresponding portion of superior handle 210 extending therethrough, for example. In various embodiments, the superior and inferior handles 210, 220 may include substantially planar top and bottom surfaces, respectively. The inferior handle 220 may extend from a proximal end thereof to a distal end thereof. The distal end of inferior handle 220 may include a branch portion 221 that is angled in the widthwise direction (e.g., laterally) with respect to the remaining portion of the inferior handle 220. For example, a longitudinal portion of the inferior handle 220 may extend in a straight direction and the branch portion 221 may be angled out laterally away from the straight direction of the longitudinal portion. The branch portion 221 may define a distal end of the inferior handle 220 and include a pair of gripping rails 223 for mating with the inferior gripping channels 101i of inferior endplate 20, for example. Additionally branch portion 221 may include a cutout 222 that is aligned with the adjustment screw guide aperture 103 when the branch portion 221 is coupled to implant 100.

Figure 28A:
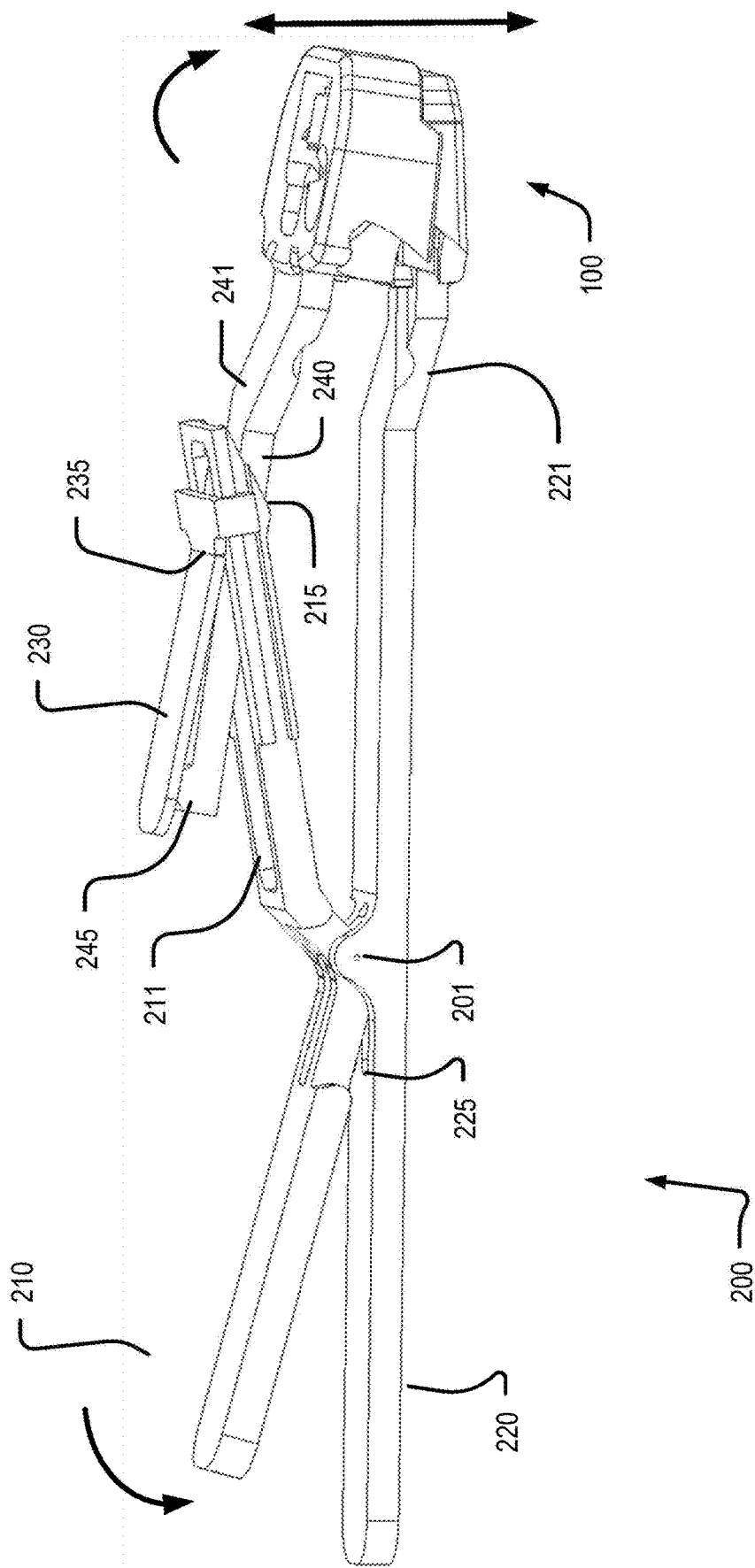
FIG. 28A is a side view of the first surgical tool of FIG. 24 and an expandable implant in a second expanded position.

As seen best in FIG. 28A, superior handle 210 may be hingedly coupled to arm 240. The distal end of arm 240 may include a branch portion 241 that is angled in the widthwise direction (e.g., laterally) with respect to the proximal portion of arm 240. For example, a longitudinal portion of the arm 240 may extend in a straight direction and the branch portion 241 may be angled out laterally away from the straight direction of the longitudinal portion. The branch portion 241 may define a distal end of the arm 240 and include a pair of gripping rails 243 for mating with the superior gripping channels 101s of superior endplate 10, for example. Additionally, branch portion 241 may include a cutout 242 that is aligned with the adjustment screw guide aperture 103 when the branch portion 241 is coupled to implant 100. At least one advantage of branch portions 221, 241 is the increased visibility provided to an end user for see and manipulating implant 100. For example, the branch portions 221, 241 offset the first surgical tool 200 from implant 100 such that visibility of implant 100 is increased relative to a straight head on configuration. In various embodiments, the inferior and superior gripping rails 223, 243 and inferior and superior gripping channels 101i, 101s may comprise a dovetail groove configuration or the like, for example as shown in the example embodiment of FIG. 25. In some embodiments, a securing mechanism may be included between the inserted and the implant. For example, a detent, a retaining screw, a claim, etc. Additionally, and at least due in part to the geometry of the superior and inferior gripping channels 101s, 101i, a connection between the surgical tool 200 and implant 100 may self-lock. For example, due to a dovetail connection the implant 100 may be securely engaged with surgical tool 200 in a collapsed position and in each of the various expanded configurations.

Superior handle 210 may be hingedly coupled to arm 240 at a second pivot point 215. For example, a slot or aperture extending through the side portions of arm 240 and a distal end of superior handle 210 may include a pin inserted therein providing a second pivot point 215. In addition to second pivot point 215, an adjustable spring flex location 235 may be provided. In some embodiments, the combination of spring flex location 235 and second pivot point 215 may cause a pivoting relationship between superior handle 210 and arm 240, as will be explained in more detail in view of the way that spring flex location 235 is adjustable in view of FIGS. 31-33. In various embodiments, the location of adjustable spring flex location 235 may be adjustable along a portion of the length of superior handle 210. For example, a portion of superior handle 210 distally located from hinge 201 may include a slot 211 extending through the top and bottom surfaces of superior handle 210 of which a proximal end of arm 240 may extend through when superior handle 210 and arm 240 are pivoted at second pivot point 215 (see FIG. 27). Additionally, each of the lateral side surfaces of the distal end of superior handle 210 may include a track 216 (see FIG. 24) comprising a pair of rails defining a channel therebetween. Furthermore, a sliding pivot member 237 may include an outdent and/or rail that is slidably coupled to the track 216 such that sliding pivot member 237 may slide forward and backward and the relative location of spring flex location 235 may be adjusted. Sliding pivot member 237 may be coupled to deformable spring 230 and when sliding forward and backward also move the relative location of deformable spring 230, for example. Deformable spring 230 may extend in a lengthwise direction from the sliding block member 237 towards the proximal end 200p of first surgical tool 200, for example. Deformable spring 230 may be a linear member capable of sustaining repeated elastic deformation during use of surgical tool 200, for example. Additionally, deformable spring 230 may have a width in the widthwise direction that is greater than a width of the slot 211 in the widthwise direction. Spring 230 and adjustable spring flex location 235 may facilitate controlling a transition from distraction to lordosis, for example, as will be explained in greater detail below.

Figure 26:
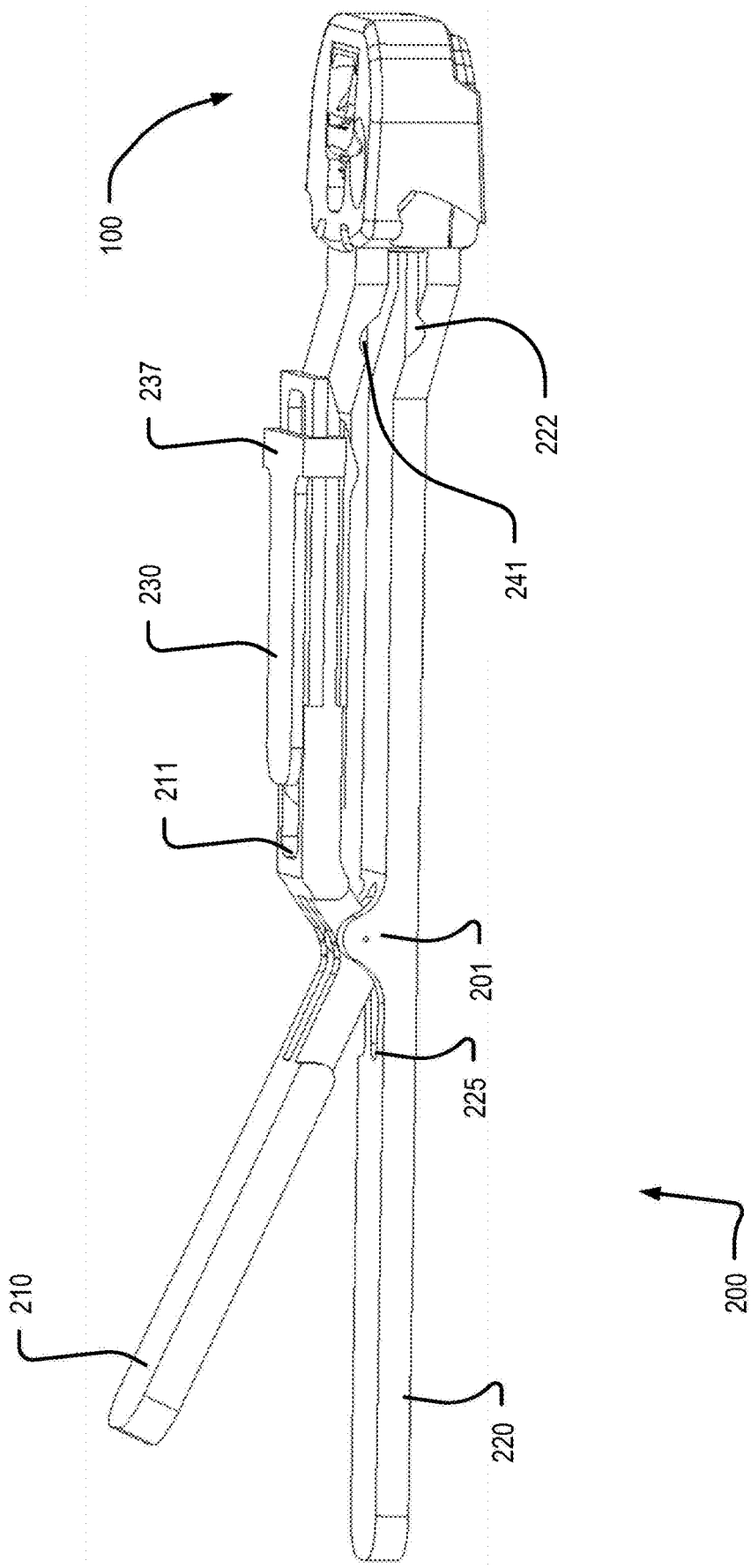
FIG. 26 is a side view of the first surgical tool of FIG. 24 and an expandable implant in a contracted position.
Figure 27:
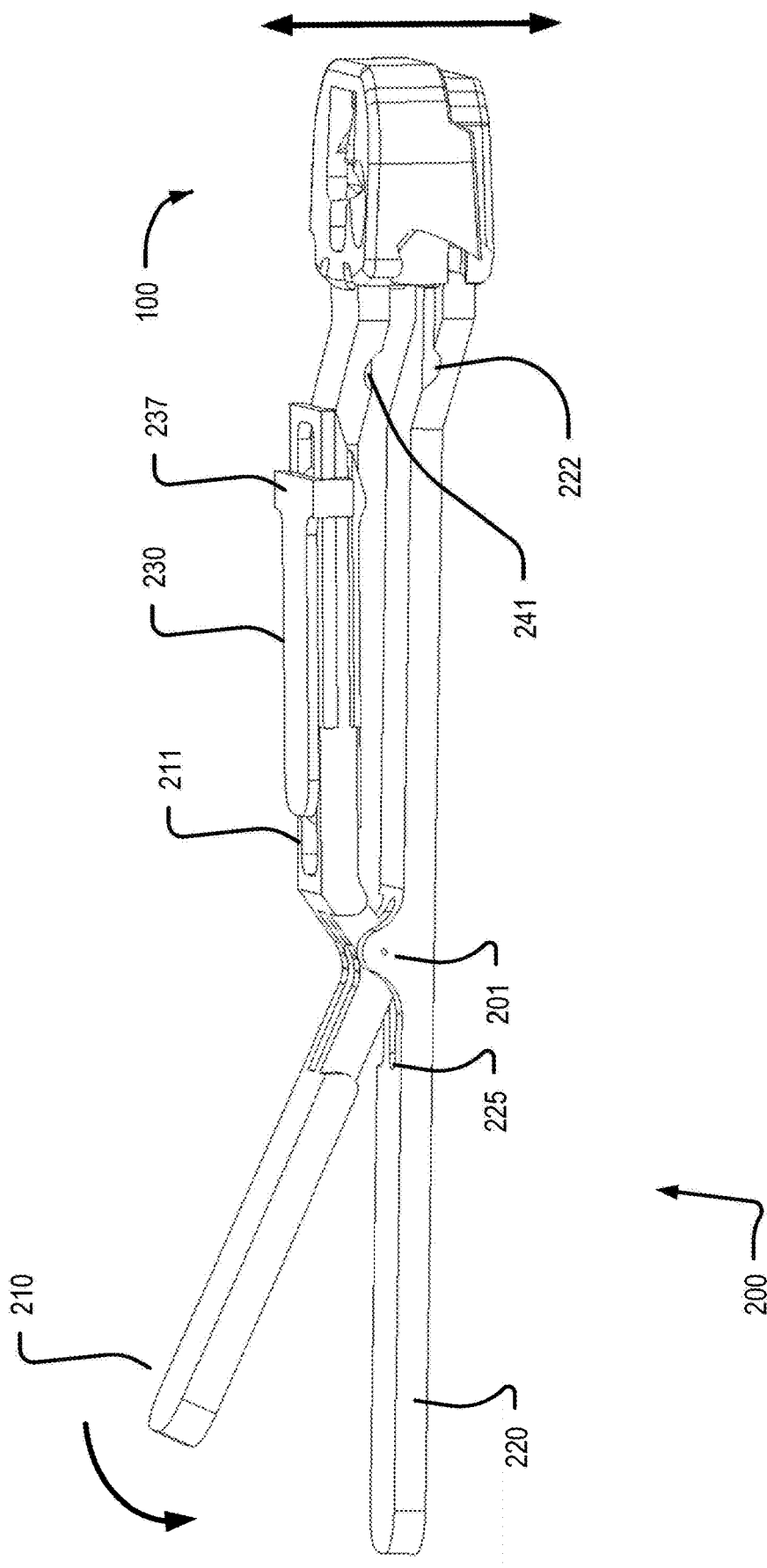
FIG. 27 is a side view of the first surgical tool of FIG. 24 and an expandable implant in a first expanded position.

As shown in FIG. 26, implant 100 is in an unexpanded position and surgical tool 200 is securely coupled to implant 100 via the inferior and superior gripping rails 223, 243 and inferior and superior gripping channels 101i, 101s as explained above. As shown in FIG. 27, an end user such as a surgeon may push down on the superior handle 210 which provides a separating force at implant 100. For example, superior branch portion 241 pushes the superior endplate 10 upward and inferior branch portion 221 pushes the inferior endplate 20 downward. As illustrated, the spring 230 initially remains non-deformed and is strong enough to resist deformation at spring flex location 235 because the applied force at superior handle 210 is insufficient to overcome the biasing force of spring 230, for example Therefore, arm 240 is constrained beneath spring 230 and surgical tool 200 is constrained from pivoting at second pivot point 215. In the example configuration of FIG. 27, the superior and inferior endplates 10, 20 are distracted vertically, e.g., a parallel distraction and/or a substantially parallel distraction. As shown in FIG. 28A, additional force is applied to superior handle 210 that is sufficient to overcome the biasing force of spring 230 such the arm 240 pivots with respect to slot 211 and extends upwards and through slot 211. In some embodiments, a clutch, ratchet or locking mechanism may be provided on surgical instrument 200 to maintain the final expanded configuration while implant 100 is positioned in the disc space (not illustrated). For example, surgical instrument 200 may be locked in a particular configuration so that the surgeon may assess the placement of implant 100 relative to the disc space and tighten set screw 50 to fix superior endplate 10 relative to inferior endplate 20, as explained above. Additionally, spring 230 is deformed at adjustable spring flex location 235 due to the force applied at the proximal end of spring 230 by arm fulcrum 245. Due to the relative change in inclination of arm 240 with respect to superior handle 210 and inferior handle 220, implant 100 is lordosed. For example, in various embodiments, implant 100 is lordosed by an amount (degree) corresponding to the angle formed between arm 240 and the portion of superior handle 210 at slot 211. As will be explained in further detail below, the amount of force required to overcome the spring 230 may be adjustable by sliding spring 230 forward and backward via sliding pivot member 237.

Figure 28B:
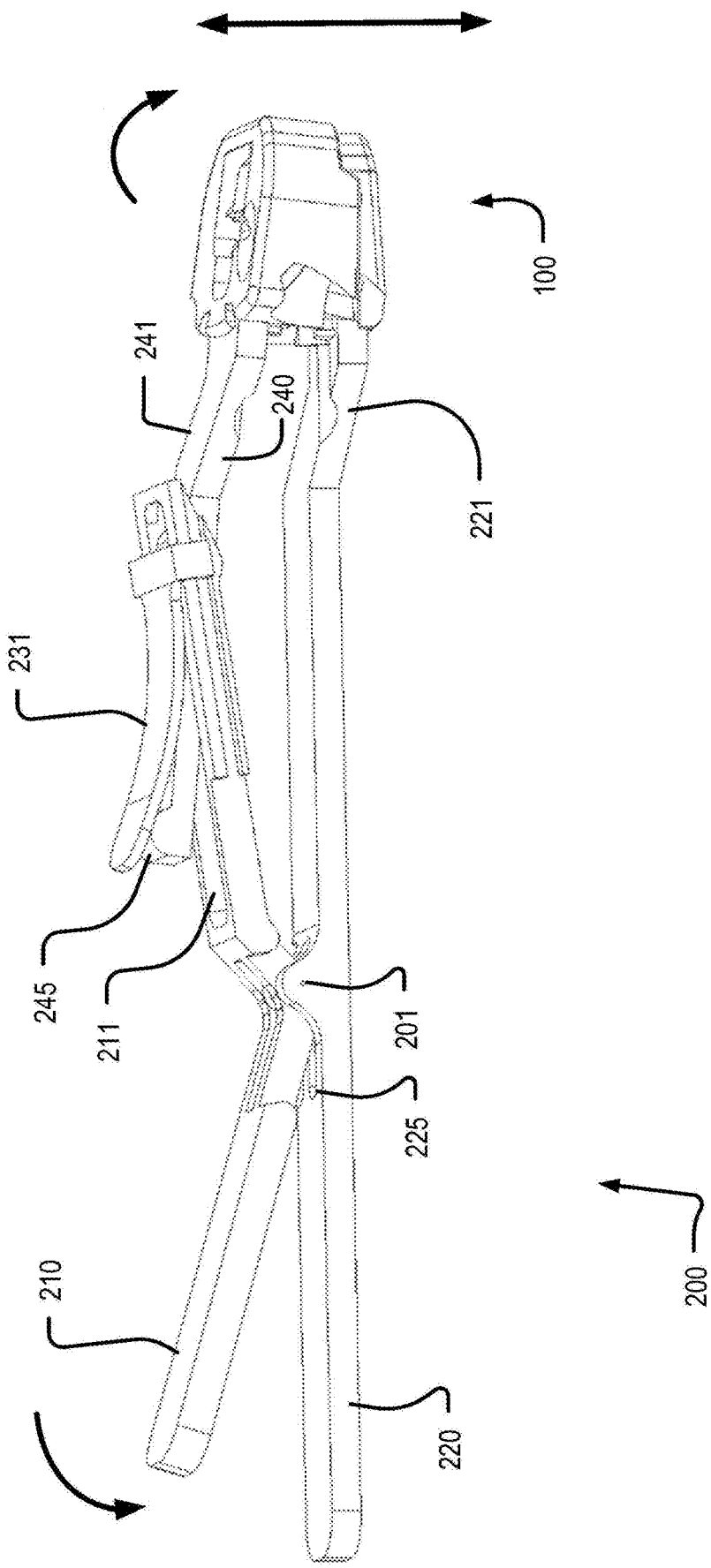
FIG. 28B is a side view of an alternate embodiment of a first surgical tool including a leaf spring.

FIG. 28B shows an alternate embodiment of the first surgical tool 200. The embodiment of FIG. 28B may include the same, substantially the same, and/or similar components and functionality as the embodiment of FIG. 28A. The alternate embodiment of FIG. 28B may include a leaf spring 231, for example, in place of spring 230. Leaf spring 231 may deflect in a curved path as shown in the example illustration of FIG. 28B rather than the spring flex location 235 as shown in FIG. 28A.

Figure 29:
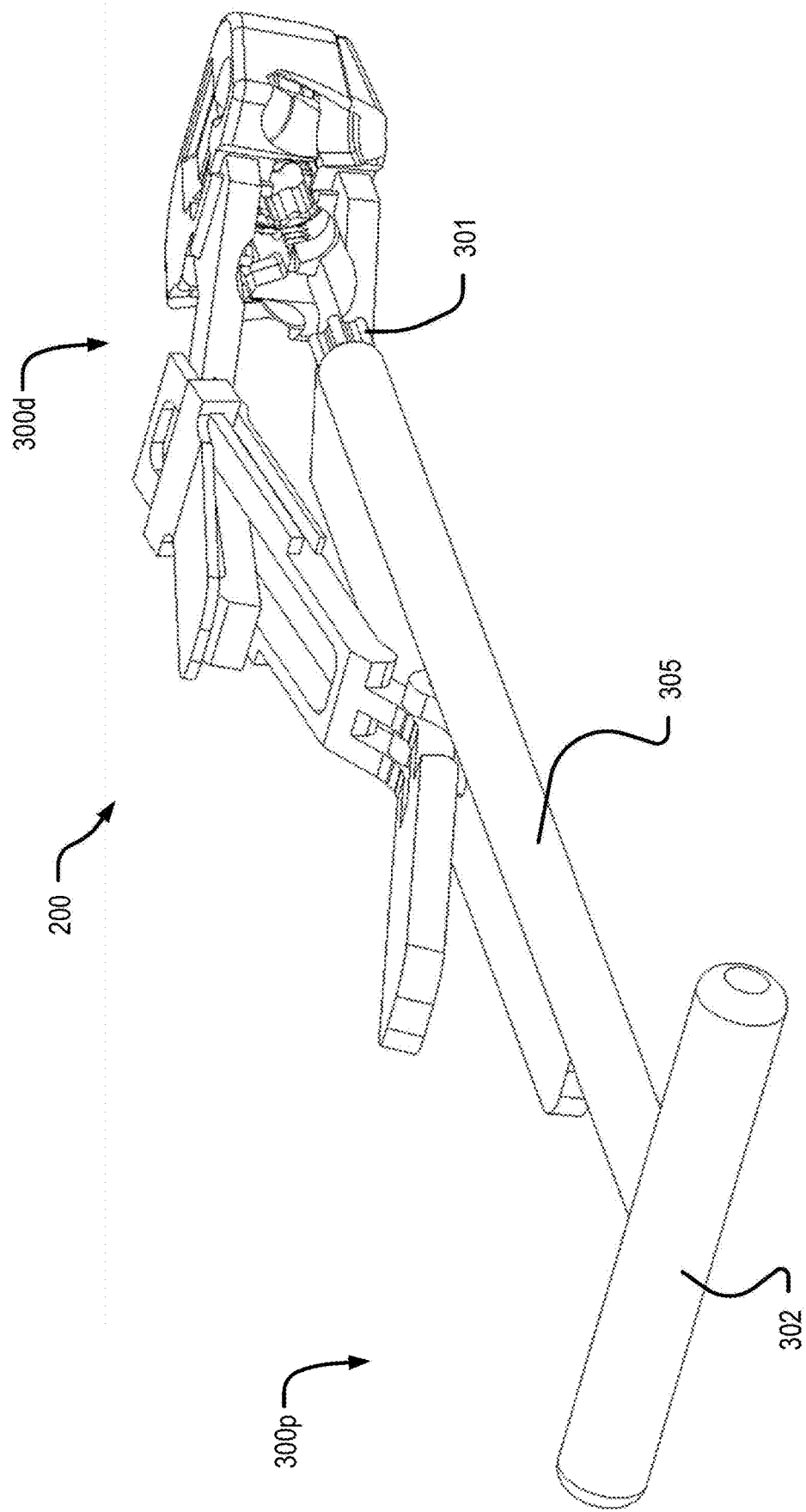
FIG. 29 is a perspective view of the first surgical tool of FIG. 24 and a second surgical tool for engaging a locking mechanism of an expandable implant.
Figure 30:
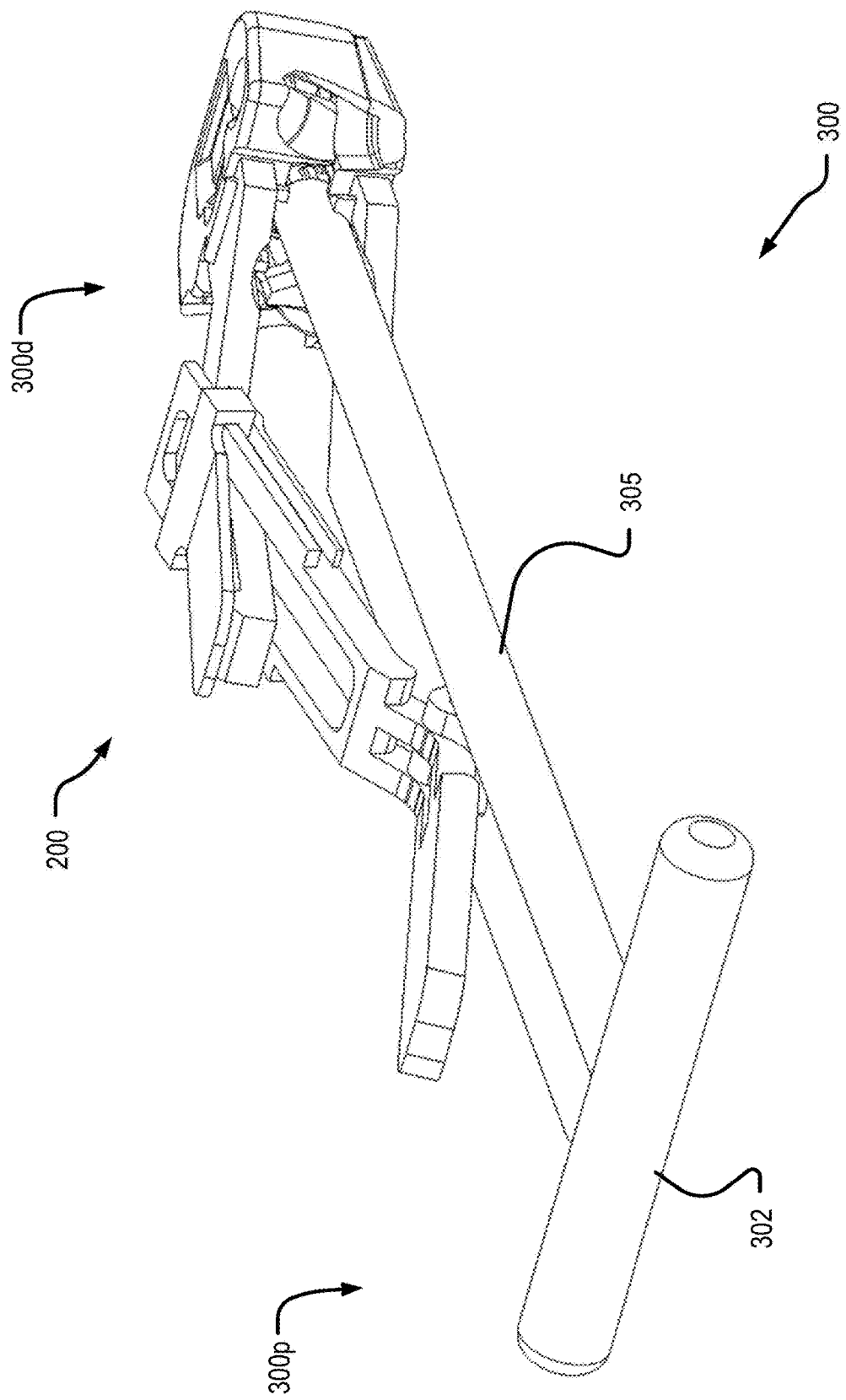
FIG. 30 is a perspective view of the first surgical tool of FIG. 24 and a second surgical tool that is engaged with a locking mechanism of an expandable implant.

FIGS. 29-30 illustrate the first surgical tool 200 engaged with implant 100 in an expanded configuration and a second surgical tool 300 for engaging the various components of the locking mechanism. In FIG. 29, it is shown that a second surgical tool 300 (also referred to as a driver) may include a drive shaft 305, a drive end 301, and a handle 302. Drive end 301 may include any type of circumferential surface for driving set screw 50. In the example embodiment, drive end 301 may include a hexolobular drive end 301 for inserting into the adjustment aperture 53 of set screw 50. In FIG. 30, it is shown that the second surgical tool 300 is inserted within screw guide aperture 103 of implant 100 and is nested within and/or passes over/under cutouts 222, 242, for example. In this embodiment, an end user may first expand implant 100 to a desired configuration and then lock implant 100 in the desired configuration by rotating set screw 50 such that it advances from a proximal end 100p of implant towards the distal end 100d of implant 100 thereby compressing the proximal saddle 40, crossbar 15, and distal saddle 60 against the inside distal surface of the inferior endplate 20, for example. Consistent with the above disclosure, in an alternative embodiment, the set screw 50 may compress only the crossbar 15 against the inside distal surface of the inferior endplate 10. In each embodiment, by sufficiently tightening set screw 50 a relative position of the superior and inferior endplates 10, 20 is fixed and/or locked.

Figure 31:
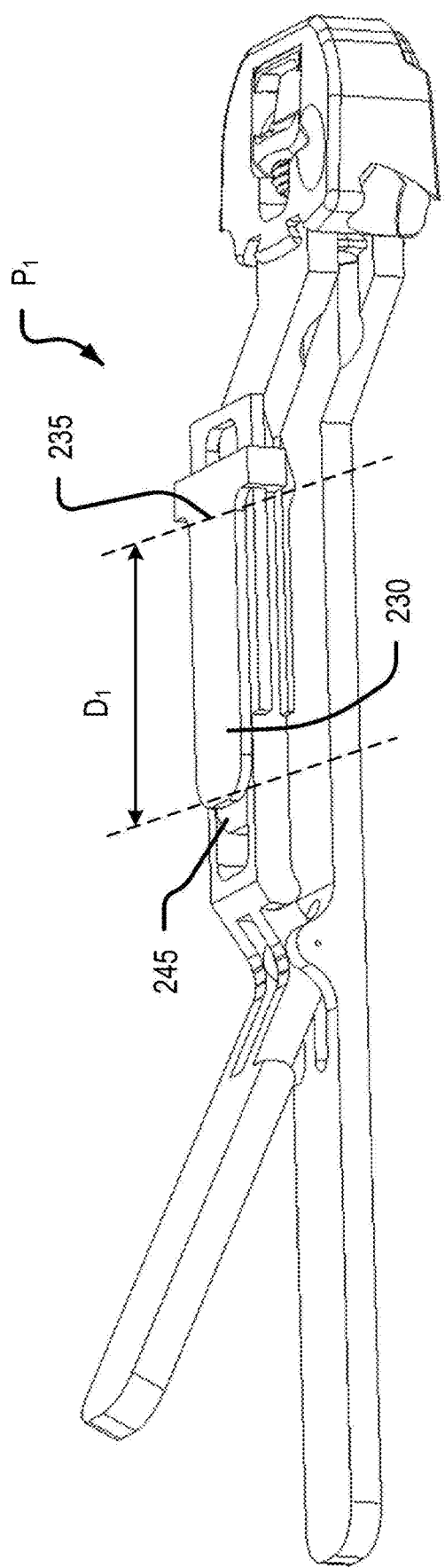
FIG. 31 is a perspective view of the first surgical tool of FIG. 24 including a spring and pivot point in a first position.
Figure 32:
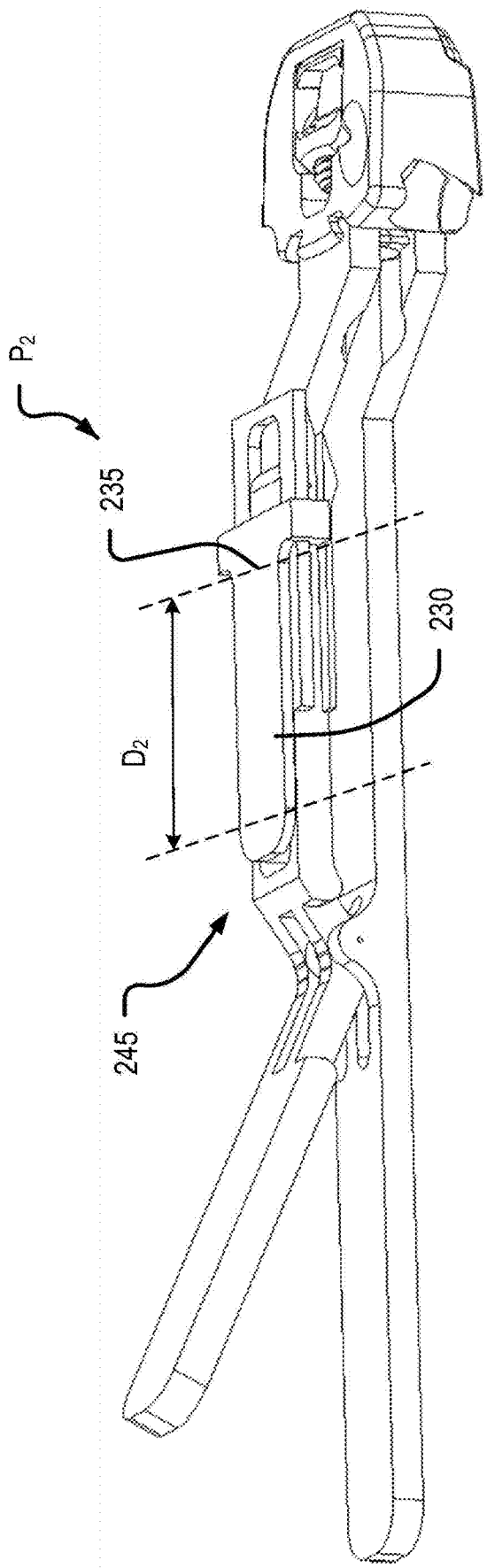
FIG. 32 is a perspective view of the first surgical tool of FIG. 24 including a spring and pivot point in a second position.
Figure 33:
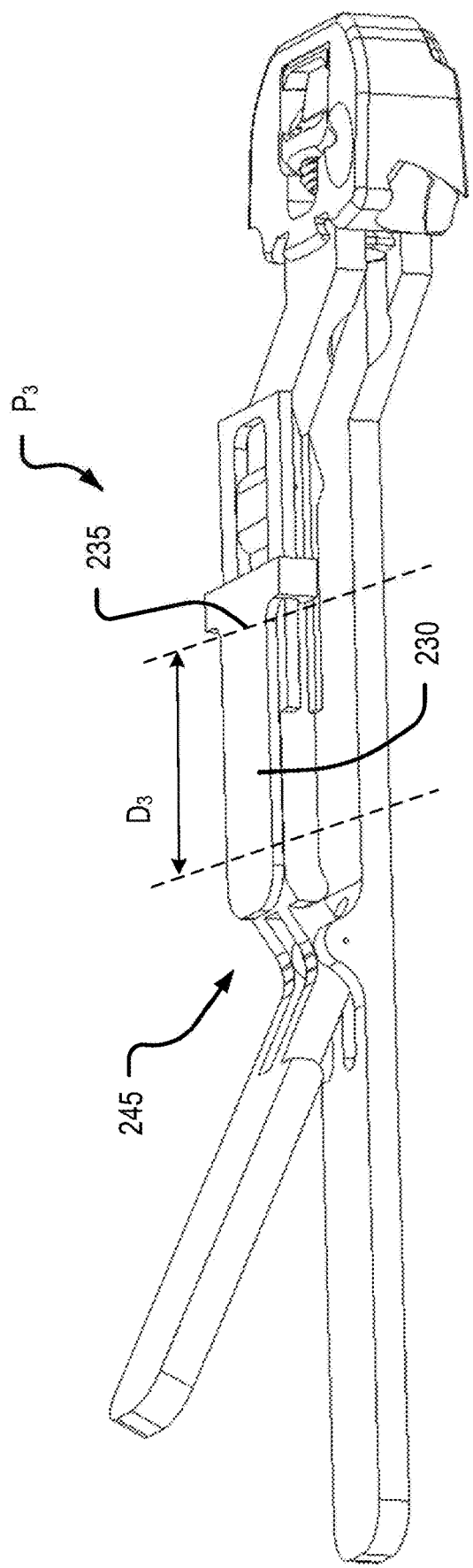
FIG. 33 is a perspective view of the first surgical tool of FIG. 24 including a spring and pivot point in a third position.

FIGS. 31-33 are various perspective views of the first surgical tool 200 with the spring 230 and adjustable spring flex location 235 in a series of different locations. For example, as shown in FIG. 31, adjustable spring flex location 235 is located at a first pivot location $P_1$ due to sliding block 237 being relatively far forward in the distal direction. In the first pivot location $P_1$, a moment arm may be defined by a first distance $D_1$ from adjustable spring flex location 235 to fulcrum 245. As shown in FIG. 31, adjustable spring flex location 235 is located at a second pivot location $P_2$ due to sliding block 237 being moved in the proximal direction relative to the first pivot location $P_1$. In the second pivot location $P_2$, a moment arm may be defined by a second distance $D_1$ from adjustable spring flex location 235 to fulcrum 245. In comparing the first distance $D_1$ and second distance $D_2$, it is apparent that in the second pivot location $P_2$ a relatively greater force must be applied to overcome the biasing force of spring 230 relative to the force required to overcome the biasing force of spring 230 in the first pivot location. For example, the second distance $D_2$ is less than the first distance $D_1$ and provides less of a moment arm. As shown in FIG. 32, adjustable spring flex location 235 is located at a second pivot location $P_3$ due to sliding block 237 being moved in the proximal direction relative to the second pivot location $P_2$. In the third pivot location $P_3$, a moment arm may be defined by a third distance $D_3$ from adjustable spring flex location 235 to fulcrum 245. In comparing the second distance $D_2$ and third distance $D_3$, it is apparent that in the third pivot location $P_3$ a relatively greater force must be applied to overcome the biasing force of spring 230 relative to the force required to overcome the biasing force of spring 230 in the second pivot location $P_2$. For example, the third distance $D_3$ is less than the second distance $D_2$ and provides less of a moment arm.

Figure 34:
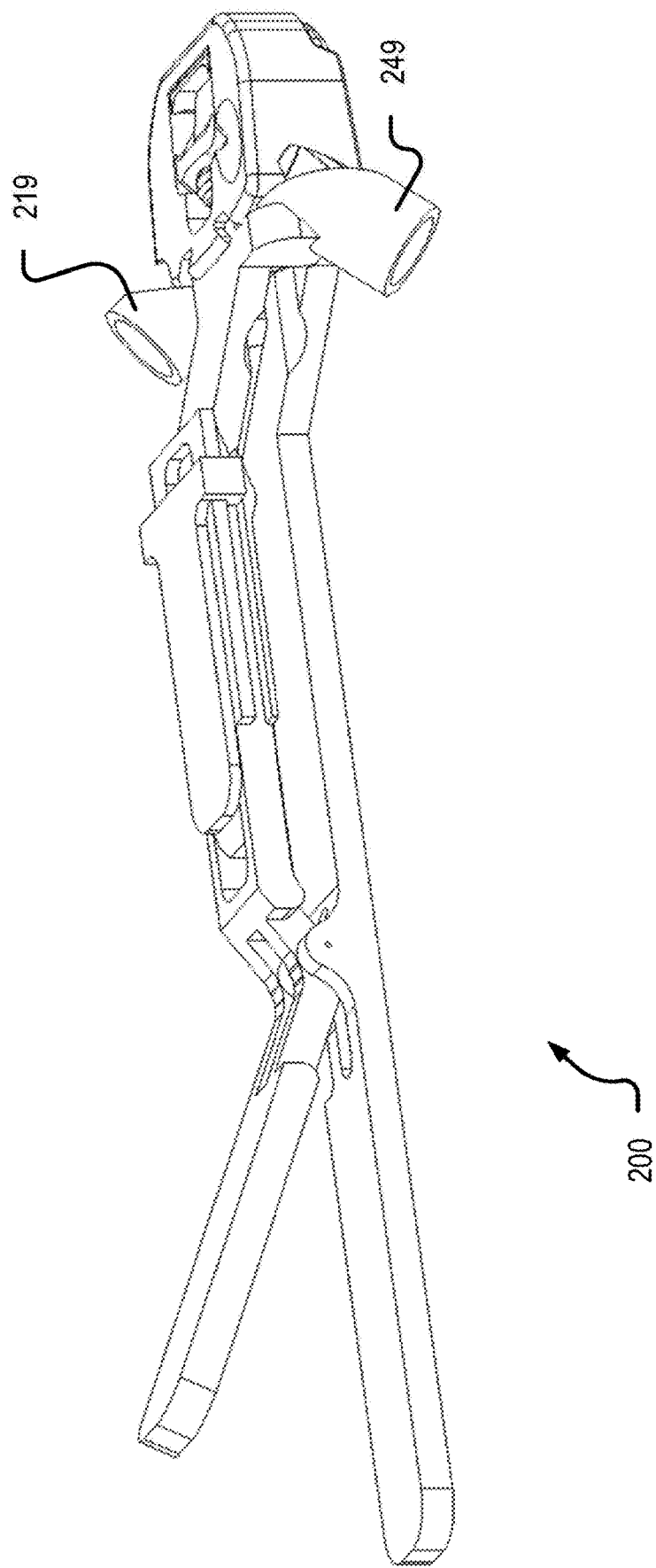
FIG. 34 is a perspective view of a first surgical tool in a collapsed position having a pair of bone screw guides.

FIG. 34 is a perspective view of a first surgical tool 200 in a collapsed position having a pair of bone screw guides 219, 249. In various embodiments, first bone screw guide 219 may be joined to branch portion 241 and second bone screw guide 249 be joined to branch portion 221. As shown in FIG. 35, first surgical tool 200 is in an expanded position where implant 100 is distracted and lordosed. For example, in various embodiments an end user may expand implant 100 to a desired configuration and thereafter may utilize bone screw guides 219, 249 for accurately orienting bone screws 110 in a trajectory that corresponds to the target trajectory of bone screw apertures 13, 21. In some embodiments, an end user may drill a passageway into the patient vertebrae and utilize bone screw guides 219, 249 for aligning a drill bit. Additionally, in some embodiments a plug (not illustrated) may be insert in the passageway of bone screw guides 219, 249 and the plug may include a relatively small diameter passageway coaxially aligned with the center of the passageway of bone screw guides 219, 249. In this way, a relatively small "pilot hole" may be drilled into the boney structure with an appropriate trajectory.

Figure 24:
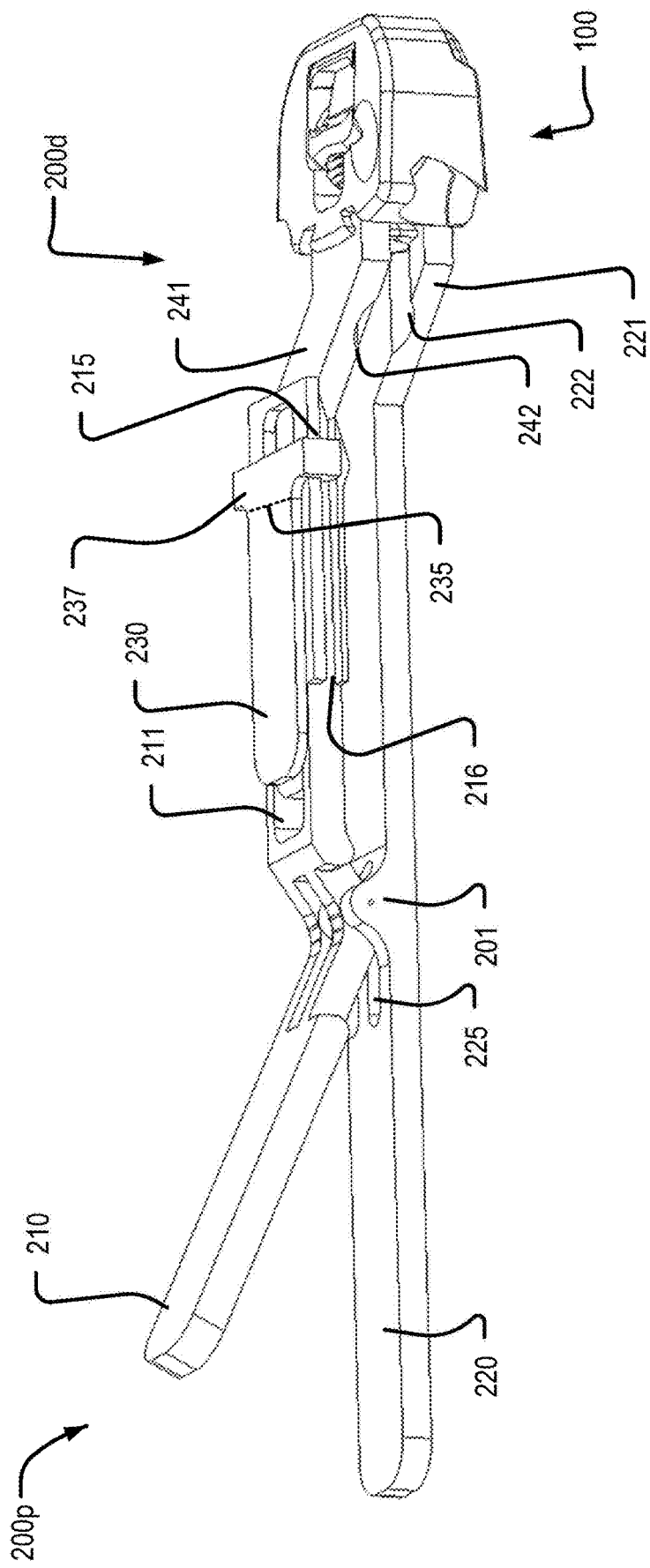
FIG. 24 is a perspective view of a first surgical tool for use with disclosed expandable implants.
Figure 25:
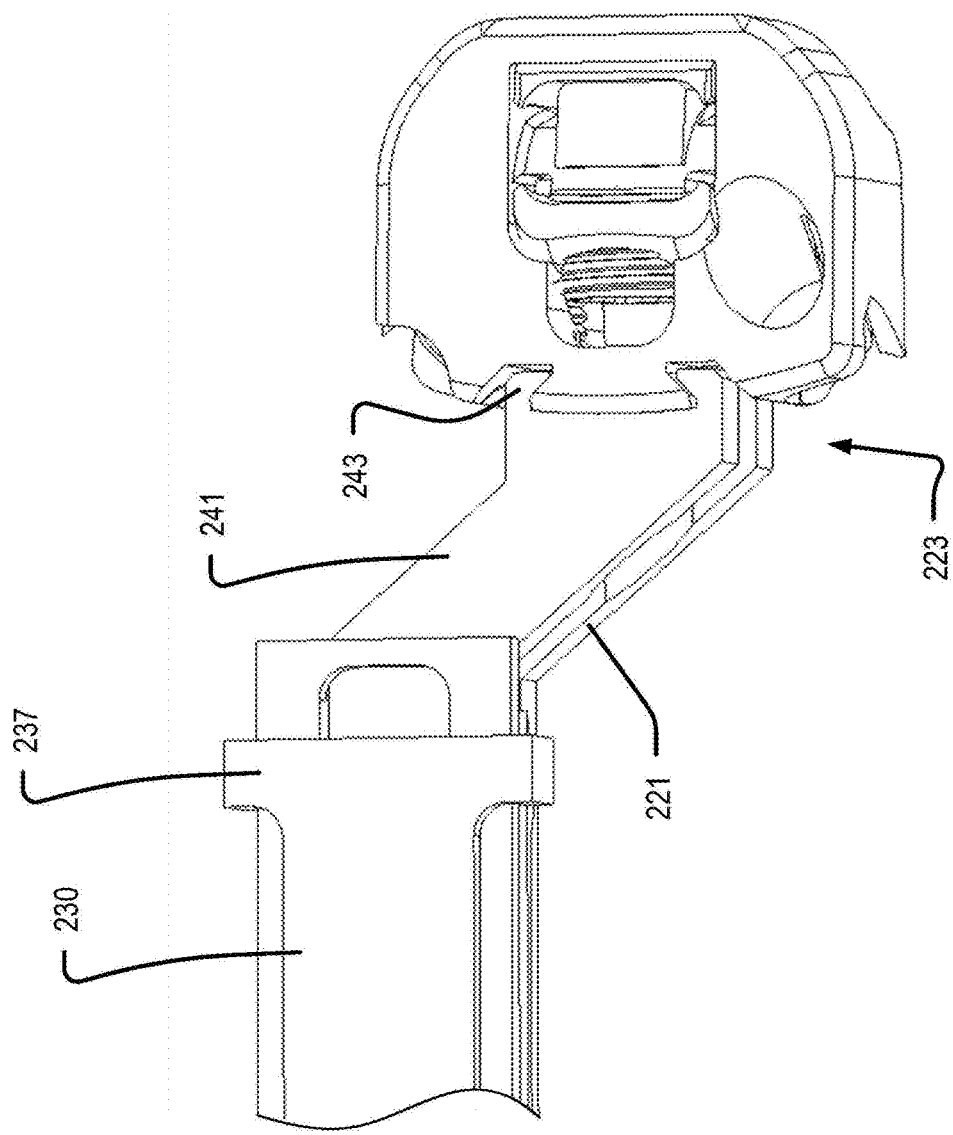
FIG. 25 is a top down view of the distal end of the first surgical tool of FIG. 24.

In at least some surgical procedures, after expansion and fixing the relative location of superior endplate 10 with respect to inferior endplate 20, biological material such as a portion of a patient's bone, a cadaver bone, a synthetic material, a BGM, and various combinations thereof may be introduced into the interior of implant 100 through screw guide aperture 103 and/or a gap 24 between the superior endplate 10 and inferior endplate 20, e.g., the gap 24 as shown in FIGS. 15 and 24. Such biological material may be packed as a solid structure and/or injected as a fluid under pressure or even a combination of both. With reference to FIG. 18A, 18B, in some embodiments, the interior walls may be fitted closely such that material will remain in the interior of implant 100. In some embodiments, set screw 50 may be cannulated and or have a fitting at the proximal end thereof to connect to a cannula for injecting flowable material (not illustrated). Similarly, proximal saddle 40 may have a through hole such that graft material may flow through proximal saddle 40 and surround any gaps 24 above and/or below cross bar. For example, gaps 24 as shown in FIG. 23. Likewise, cross bar 15 and distal saddle 60 may have through holes as well (not illustrated). Such material can be placed and/or injected into implant 100 in any available gap 24, seam, aperture, etc. For example, through any aperture through superior endplate 10, inferior endplate 20, and gaps 24 that are formed during the expansion of implant 100. For example, various conduits, through holes, and passageways may be provided in the interior components such that a flow able graft material may envelop and/or surround the locking mechanism of implant 100. In some embodiments, (not illustrated) integral curtains may be initially formed on the outside surfaces of superior endplate 10 and/or inferior endplate 20 to contain graft material. In other embodiments, (not illustrated) integral curtains may be pinned to implant 100 in-situ after it is expanded in areas where graft material may flow out, e.g., in areas that the adjacent vertebrae may not already be providing a wall. In some embodiments (not illustrated), a stabilization plate may also keep graft material in place and such a stabilization plate may be particularly advantageous when pre-packing solid graft material.

FIG. 36 is a reference drawing showing the human spine of which various disclosed implant embodiments may be installed in. FIG. 37 is a reference drawing showing various planes and reference directions of which the various disclosed implant embodiments may move in or act in with reference to a patient 1.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. An expandable implant movable between a contracted position and an expanded position, comprising:
   an expandable body extending from a proximal end to a distal end in a proximal-to-distal direction, extending from a first lateral side to a second lateral side in a widthwise direction, and extending from a superior end to an inferior end in a vertical direction, the expandable body being defined by a superior endplate and an inferior endplate opposite the superior endplate;
   the superior endplate comprises:
      a first inside surface extending in the proximal-to-distal direction between a first inside proximal wall and a first inside distal wall; and
      a crossbar extending in the widthwise direction proximate the first inside distal wall;
   the inferior endplate comprises:
      a second inside surface extending in the proximal-to-distal direction between a second inside proximal wall and a second inside distal wall;
      a medial support structure;
      a threaded core extending in the proximal-to-distal direction between the second inside proximal wall and the medial support structure; and
      a receiving cavity disposed between the medial support structure and the second inside distal wall, wherein the crossbar of the superior endplate is disposed within the receiving cavity;
   a threaded locking screw disposed in the threaded core and movable in the proximal-to-distal direction between the second inside proximal wall and the medial support structure;
   a proximal saddle disposed in the receiving cavity, the proximal saddle having a proximal end portion facing the threaded locking screw and a distal end portion facing a proximal end of the crossbar; and
   a distal saddle disposed in the receiving cavity, the distal saddle including a proximal surface facing a distal end of the crossbar and a distal surface facing the second inside distal wall,
   wherein, in a locked position, a relative position of the inferior endplate with respect to the superior endplate is fixed.

2. The expandable implant of claim 1, wherein:
   in the locked position, the threaded locking screw directly contacts the proximal saddle, the proximal saddle directly contacts the crossbar, the crossbar directly contacts the distal saddle, and the distal saddle directly contacts the second inside distal wall, and
   in the locked position, the threaded locking screw presses the proximal saddle against the crossbar, causing, in turn, the crossbar to compress the distal saddle against the second inside distal wall.

3. The expandable implant of claim 1, wherein:
the medial support structure includes a first tang and a second tang opposite the first tang, and
the first and second tangs face the receiving cavity.

4. The expandable implant of claim 3, wherein a first horizontal distance between the first tang and the second tang is greater than a second horizontal distance between a first lateral end of the proximal saddle and a second lateral end of the proximal saddle.

5. The expandable implant of claim 1, wherein the proximal end portion of the proximal saddle is defined by a spherical end cap.

6. The expandable implant of claim 5, wherein:
the proximal end of the crossbar includes a channel extending in the vertical direction,
the distal end portion of the proximal saddle includes a post, and
in the locked position, the post is seated within the vertical channel.

7. The expandable implant of claim 1, wherein:
the distal end of the crossbar is defined by a first curved surface, and
the proximal surface of the distal saddle is defined by a second curved surface that corresponds in size and shape to the first curved surface.

8. The expandable implant of claim 7, wherein the distal surface of the distal saddle is substantially planar and a portion of the second inside distal wall directly contacting the distal surface of the distal saddle is substantially planar.

9. The expandable implant of claim 1, wherein outside lateral side surfaces of the inferior endplate are nested within inside lateral side surfaces of the superior endplate.

10. The expandable implant of claim 1, wherein in an unlocked position the superior endplate and inferior endplate are freely movable in the vertical direction with respect to one another.

11. A system for installing, expanding, and locking an expandable implant, comprising:
the expandable implant of claim 1,
wherein:
the proximal end of the implant includes an adjustment aperture providing access to the threaded locking screw, and
a first engagement channel and a second engagement channel are disposed on opposite sides of the adjustment aperture, respectively,
a first surgical tool extending from a proximal end to a distal end, comprising:
a first engagement prong and a second engagement prong disposed at the distal end for coupling to the first engagement channel and second engagement channel, respectively, and
a superior handle coupled to an inferior handle at a pivot point,
a second surgical tool extending longitudinally from a handle to a drive portion, the drive portion having an outside circumferential surface corresponding in size and shape to an inside circumferential surface of the threaded locking screw.

12. The system of claim 11, wherein the first surgical tool further comprises a superior arm portion coupled to the superior handle at an adjustable pivot point.

13. The system of claim 12, wherein:
the superior handle includes a top surface and a bottom surface opposite the top surface, a first lateral side surface and a second lateral side surface opposite the first lateral side surface, the first and second lateral side surfaces extending between the top surface and the bottom surface, respectively,
a longitudinal slot extends through the top surface and the bottom surface of the superior handle,
a first track extends along the first lateral side surface adjacent the longitudinal slot,
a second track extends along the second lateral side surface adjacent the longitudinal slot, and
the superior arm portion extends within the slot.

14. The system of claim 13, wherein:
the adjustable pivot point comprises a sliding block including a first outdent having a size and shape corresponding to a size and shape of the first track and a second outdent having a size and shape corresponding to a size and shape of the second track, and
the first and second outdents being seated within the first and second tracks, respectively.

15. The system of claim 12, wherein:
the superior arm portion includes a first angled branch portion proximate the distal end of the first surgical tool, the first angled branch portion being angled with respect to a longitudinal axis of the superior handle, and
the inferior handle includes a second angled branch portion proximate the distal end of the first surgical tool, the second angled branch portion being angled with respect to a longitudinal axis of the superior handle.

16. The system of claim 15, wherein:
the first angled branch portion includes a first cutout on a bottom surface thereof,
the second angled branch portion includes a second cutout on a top surface thereof, and
the first cutout and second cutout are aligned with the adjustment aperture when the first engagement prong and second engagement prong are coupled to the first engagement channel and second engagement channel, respectively.

17. The system of claim 15, wherein:
the inferior endplate comprises a first bone screw aperture that is angled with respect to the inferior endplate by a first degree and the superior endplate comprises a second bone screw aperture that is angled with respect to the superior endplate by a second degree,
the first angled branch portion comprises a first bone screw guide having an angled passageway that is angled with respect to an upper surface of the distal end of the first surgical tool by an amount corresponding to the second degree, and
the second angled branch portion comprises a second bone screw guide having an angled passageway that is angled with respect to a lower surface of the distal end of the first surgical tool by an amount corresponding to the first degree.

18. An expandable implant, comprising:
an expandable body movable between a first expanded position and a second expanded position, the expandable body extending from a proximal end to a distal end in a proximal-to-distal direction, extending from a first lateral side to a second lateral side in a widthwise direction, and extending from a superior end to an inferior end in a vertical direction, the expandable body being defined by a superior endplate and an inferior endplate opposite the superior endplate;

the superior endplate comprises:
- a first inside surface extending in the proximal-to-distal direction between a first inside proximal wall and a first inside distal wall and extending in the widthwise direction between a first inside lateral wall and a second inside lateral wall; and
- a crossbar extending in the widthwise direction between the first inside lateral wall and the second inside lateral wall proximate the first inside distal wall;

the inferior endplate comprises:
- a second inside surface extending in the proximal-to-distal direction between a second inside proximal wall and a second inside distal wall, and extending in the widthwise direction between a third inside lateral wall and a fourth inside lateral wall; and
- a threaded core defining a rotation axis extending in the proximal-to-distal direction;

a threaded locking screw disposed in the threaded core and rotatable about the rotation axis, the threaded locking screw being movable forward and backward along the rotation axis upon rotation of the threaded locking screw about the rotation axis between an unlocked position and a locked position, wherein:
- in the unlocked position, a relative position of the superior endplate with respect to the inferior endplate is adjustable between the first expanded position and the second expanded position,
- in the first expanded position, a top surface of the superior endplate and a bottom surface of the inferior endplate extend in a substantially parallel direction, respectively, with respect to the rotation axis,
- in the second expanded position, the top surface of the superior endplate is inclined with respect to the bottom surface of the inferior endplate, and
- in the locked position, a relative position of the superior endplate with respect to the inferior endplate is fixed and the threaded locking screw directly contacts the crossbar against the second inside distal wall.

19. The expandable implant of claim 18, wherein:
- the inferior endplate further comprises a distal outside surface, a first outside lateral side surface, and a second outside lateral side surface, and
- the distal outside surface, first lateral outside side surface, and second outside lateral side surface are adjacent to and nested within the first inside distal wall, the first inside lateral wall, and the second inside lateral wall, respectively.

20. The expandable implant of claim 18, wherein the superior endplate and inferior endplate are uncoupled and are only secured relative to one another in the locked position.

* * * * *